(12) United States Patent
Nash et al.

(10) Patent No.: US 8,399,405 B2
(45) Date of Patent: Mar. 19, 2013

(54) PEPTIDOMIMETIC MACROCYCLES

(75) Inventors: Huw M. Nash, Concord, MA (US); David Allen Annis, Cambridge, MA (US); Rosana Kapeller-Libermann, Chestnut Hill, MA (US); Tomi K. Sawyer, Southborough, MA (US); Noriyuki Kawahata, West Roxbury, MA (US)

(73) Assignee: Aileron Therapeutics, Inc., Cambridge, MA (US)

( * ) Notice: Subject to any disclaimer, the term of this patent is extended or adjusted under 35 U.S.C. 154(b) by 0 days.

(21) Appl. No.: 13/366,113

(22) Filed: Feb. 3, 2012

(65) Prior Publication Data

US 2012/0172311 A1 Jul. 5, 2012

Related U.S. Application Data

(63) Continuation of application No. 12/564,910, filed on Sep. 22, 2009.

(60) Provisional application No. 61/099,063, filed on Sep. 22, 2008.

(51) Int. Cl.
*A61K 38/02* (2006.01)
*C07K 2/00* (2006.01)

(52) U.S. Cl. .......................... 514/1.1; 514/21.2; 530/300

(58) Field of Classification Search .................. None
See application file for complete search history.

(56) References Cited

U.S. PATENT DOCUMENTS

| | | | |
|---|---|---|---|
| 7,192,713 | B1 | 3/2007 | Verdine et al. |
| 7,202,332 | B2 | 4/2007 | Arora et al. |
| 7,705,118 | B2 | 4/2010 | Arora et al. |
| 7,723,469 | B2 | 5/2010 | Walensky et al. |
| 7,786,072 | B2 | 8/2010 | Verdine et al. |
| 2005/0250680 | A1 | 11/2005 | Walensky et al. |
| 2008/0242598 | A1 | 10/2008 | Fairlle et al. |
| 2008/0261871 | A1 | 10/2008 | Schwartz |
| 2008/0262200 | A1 | 10/2008 | Nash |
| 2009/0047711 | A1 | 2/2009 | Nash |
| 2009/0088553 | A1 | 4/2009 | Nash |
| 2009/0149630 | A1 | 6/2009 | Walensky et al. |
| 2009/0176964 | A1 | 7/2009 | Walensky et al. |
| 2010/0184628 | A1 | 7/2010 | Nash |
| 2010/0184645 | A1 | 7/2010 | Verdine et al. |
| 2010/0216688 | A1 | 8/2010 | Nash et al. |
| 2010/0234563 | A1 | 9/2010 | Arora et al. |
| 2010/0298201 | A1 | 11/2010 | Nash et al. |
| 2011/0028753 | A1 | 2/2011 | Verdine et al. |

FOREIGN PATENT DOCUMENTS

| | | | |
|---|---|---|---|
| WO | WO 2009/099677 A3 | 12/1990 | |
| WO | WO 2005/044839 A2 | 5/2005 | |
| WO | WO 2005/044839 A3 | 7/2005 | |
| WO | WO 2006/020121 A1 | 2/2006 | |
| WO | WO 2006/103666 A2 | 10/2006 | |
| WO | WO 2006/103666 A3 | 3/2007 | |
| WO | WO 2008/061192 A2 | 5/2008 | |
| WO | WO 2008/076904 A1 | 6/2008 | |
| WO | WO 2008/061192 A3 | 7/2008 | |
| WO | WO 2008/104000 A2 | 8/2008 | |
| WO | WO 2008/104000 A3 | 11/2008 | |
| WO | WO 2009/099677 A2 | 8/2009 | |
| WO | WO 2009/108261 A2 | 9/2009 | |
| WO | WO 2009/108261 A3 | 1/2010 | |

OTHER PUBLICATIONS

U.S. Appl. No. 13/370,057, filed Feb. 9, 2012, Nash et al.
European search report and opinion dated Mar. 22, 2012 for EP Application No. 09828398.9.
Schafmeister et al. An all-hydrocarbon crosslinking system for enhancing the helicity and metabolic stability of peptides. J. Am Chem. Soc. 2000;122:5891-5892.
Taylor. The synthesis and study of side-chain lactam-bridged peptides. Biopolymers. 2002;66(1):49-75.
U.S. Appl. No. 12/905,072, filed Oct. 14, 2010, Nash et al.
U.S. Appl. No. 13/097,930, filed Apr. 29, 2011, Nash.
U.S. Appl. No. 13/250,344, filed Sep. 30, 2011, Arora et al.
U.S. Appl. No. 13/252,751, filed Oct. 4, 2011, Walensky et al.
International search report dated Feb. 19, 2010 for PCT Application No. US2009/057934.
International search report dated Mar. 4, 2010 for PCT Application No. US2009/065824.
Lee, et al. A novel BH3 ligand that selectively targets Mcl-1 reveals that apoptosis can proceed without Mcl-1 degradation. J Cell Biol. Jan. 28, 2008;180(2):341-355.
Rusnak, et al. A simple method for predicting serum protein binding of compounds from IC(50) shift analysis for in vitro assays. Bioorg Med Chem Lett. May 3, 2004;14(9):2309-12.
Sanchez-Garcia, et al. Tumorigenic activity of the BCR-ABL oncogenes is mediated by BCL2. Proc Natl Acad Sci U S A. Jun. 6, 1995;92(12):5287-91.
Trainor, G. The importance of plasma protein binding in drug discovery. Expert Opinion on Drug Discovery. Jan. 2007; 2(1):51-64.
Werle, et al. Strategies to improve plasma half life time of peptide and protein drugs. Amino Acids. 2006; 30:351-367.
Copeland. Determination of serum protein binding affinity of inhibitors from analysis of concentration-response plots in biochemical activity assays. J Pharm Sci. Aug. 2000;89(8):1000-7.
Office action dated Jan. 8, 2013 for U.S. Appl. No. 12/564,910.
Shepherd, et al. Consecutive cyclic pentapeptide modules form short alpha-helices that are very stable to water and denaturants. Angew Chem Int Ed Engl. May 10, 2004;43(20):2687-90.
Shepherd, et al. Single turn peptide alpha helices with exceptional stability in water. J Am Chem Soc. Mar. 9, 2005;127(9):2974-83.

*Primary Examiner* — Julie Ha
(74) *Attorney, Agent, or Firm* — Wilson Sonsini Goodrich & Rosati

(57) ABSTRACT

Biologically active crosslinked polypeptides with improved properties relative to their corresponding precursor polypeptides; and methods of making and identifying such improved polypeptides.

28 Claims, 4 Drawing Sheets

Figure 3

EC$_{50}$ versus Percent Serum (as HSA Concentration in µM) for select peptides

PEPTIDOMIMETIC MACROCYCLES

CROSS REFERENCE

This application is a Continuation Application which claims the benefit of U.S. application Ser. No. 12/564,910, filed Sep. 22, 2009; which claims the benefit of U.S. Provisional Application No. 61/099,063, filed Sep. 22, 2008, which is incorporated herein in its entirety by reference.

The instant application contains a Sequence Listing which has been submitted in ASCII format via EFS-Web and is hereby incorporated by reference in its entirety. Said ASCII copy, created on Feb. 21, 2012, is named 35224202.txt and is 63,708 bytes in size.

BACKGROUND OF THE INVENTION

Recombinant or synthetically produced peptides have important applications as pharmaceuticals. Peptides, however, often suffer from poor metabolic stability, poor cell penetrability, and promiscuous binding due to conformational flexibility. One approach to stabilizing these peptides is to use intramolecular crosslinkers to maintain the peptide in the desired configuration, for example using disulfide bonds, amide bonds, or carbon-carbon bonds to link amino acid side chains. See, e.g., Jackson et al. (1991), *J. Am. Chem. Soc.* 113:9391-9392; Phelan et al. (1997), *J. Am. Chem. Soc.* 119: 455-460; Taylor (2002), *Biopolymers* 66: 49-75; Brunel et al. (2005), *Chem. Commun.* (20):2552-2554; Hiroshige et al. (1995), *J. Am. Chem. Soc.* 117: 11590-11591; Blackwell et al. (1998), *Angew. Chem. Int. Ed.* 37:3281-3284; Schafmeister et al. (2000), *J. Am. Chem. Soc.* 122:5891-5892; Walensky et al. (2004), *Science* 305:1466-1470; Bernal et al. (2007), *J. Am. Chem Soc.* 129:2456-2457; U.S. Pat. No. 7,192,713 B1 (Verdine et al) (describing cross-linked stabilized-helical peptides comprising natural and non-natural amino acids, wherein the peptide comprises at least two reactive moieties capable of undergoing a C—C bond-forming reaction); and U.S. Pat. No. 5,811,515 (Grubbs et al) (describing the synthesis of conformationally-restricted/cyclic-stabilized peptides and peptidomimetics from precursors containing two or more unsaturated C—C bonds); the contents of which patents and publications are incorporated herein by reference. Such polypeptides which are conformationally stabilized by means of intramolecular cross-linkers are sometimes referred to as "stapled" polypeptides.

A major advantage of these crosslinked polypeptides is that they have an enhanced ability to penetrate cell membranes relative to their non-stapled counterparts. This cellular uptake is believed to be mediated by an active transport mechanism utilizing endocytosis.

Some of the physical characteristics which facilitate the entry of the peptides into the cells also tend to increase the affinity of crosslinked peptides to serum proteins, such as albumin. Consequently, many highly promising leads exhibit a marked "serum shift", having greatly diminished activity in vivo or in assays having serum based media, compared to activity in assays using serum-free media, rendering the peptides less than optimal for therapeutic or diagnostic applications. Crosslinked polypeptides having low levels of serum binding, however, tend to have poor cell penetration, as well as poor pharmacokinetics, e.g., rapid renal or first pass clearance. This invention addresses this and other problems.

SUMMARY OF THE INVENTION

The invention discloses methods for the identification and optimization of crosslinked polypeptides that possess reduced affinity to serum proteins to permit good activity in the presence of serum, while still retaining sufficient affinity to the cell membranes to be readily transported into the cell, retaining sufficient affinity to serum proteins to have acceptable pharmacokinetics, and retaining high affinity binding to target receptor(s) within the cell. The inventors have discovered that there is an optimal range of serum protein binding for crosslinked polypeptides for achieving these objectives. The invention further provides optimal compounds with superior cell penetration and biological activities in the presence of serum, and structure-activity relationships to permit optimization of crosslinked polypeptides having improved therapeutic efficacies or diagnostic activities.

In one embodiment, the present invention provides a method of identifying cross-linked polypeptides with improved efficacies in human whole blood, comprising the steps of synthesizing analogs of the parent cross-linked polypeptide and performing cellular assays in the absence of human serum proteins and also in the presence of one or more concentrations of human serum, so as to determine the apparent affinity of each cross-linked polypeptide for human serum proteins.

In another embodiment, the present invention provides a method of preparing a polypeptide with optimized cellular efficacy in human whole blood, the method comprising: a) providing a parent polypeptide comprising a cross-linker connecting a first amino acid and a second amino acid of said polypeptide, and wherein the parent polypeptide penetrates cell membranes by an energy-dependent process and binds to an intracellular target; b) identifying one or more dipeptide motifs in said parent polypeptide consisting of an acidic side chain adjacent to a large hydrophobic side chain, wherein the acidic side chain is not essential to binding the target; c) replacing the acidic side chain in said motif with a neutral side chain to prepare a modified parent polypeptide; d) measuring the in vitro efficacies of the modified parent polypeptide polypeptides in a whole cell assay wherein activity is mediated by binding to the intracellular target, in the presence and absence of human serum; e) calculating the apparent affinity ($K_d^*$) of the modified polypeptide to human serum proteins and its $EC_{50}$; and f) selecting the modified parent polypeptide as an optimized polypeptide if said modified parent polypeptide has a higher $K_d^*$ and an equal or lower $EC_{50}$ than the parent polypeptide. In some embodiments, $K_d^*$ is defined by the equation $$EC'_{50} = EC_{50} + P\left(\frac{n}{1 + \frac{K_d^*}{EC_{50}}}\right)$$

where n is 1, $EC_{50}$ is an in vitro efficacy measured in a whole cell assay in the absence of any human serum, and $EC'_{50}$ is an in vitro efficacy measured in a whole cell assay in N % human serum wherein P equals (N/100)×(700) micromolar.

In some embodiments of the method, both the acidic and large hydrophobic side chains in said dipeptide motif are not essential to binding the target and are replaced with neutral and less hydrophobic side chains, respectively.

For example, the invention provides a method of screening a polypeptide comprising a cross-linker connecting a first amino acid and a second amino acid of said polypeptide, wherein the polypeptide penetrates cell membranes by an energy-dependent process and binds to an intracellular target, the method comprising measuring the in vitro efficacy of the polypeptide in a whole cell assay in the presence and absence of human serum; calculating the apparent affinity ($k_d^*$) of the polypeptide to human serum proteins, wherein $K_d^*$ is defined by the equation $$EC'_{50} = EC_{50} + P\left(\frac{n}{1 + \frac{K_d^*}{EC_{50}}}\right)$$

where n is 1, $EC_{50}$ is an in vitro efficacy measured in a whole cell assay in the absence of any human serum, $EC'_{50}$ is an in vitro efficacy measured in a whole cell assay in N % human serum wherein P equals (N/100)×(700) micromolar; and selecting compounds having a $K_d^*$ of from 1 to 700 micromolar, e.g., 1-70 micromolar, for example 10-70 micromolar. For example, the selected compound may possess an estimated free fraction in human blood of 0.1-50%, e.g. 0.5-10% wherein the estimated free fraction is defined by the equation $$FreeFraction = \frac{K_d^*}{K_d^* + [HSA]_{total}}$$

and $[HSA]_{total}$ is 700 micromolar.

In some embodiments of the method, the biological activity (EC50) is measured as the percentage of the number of cells killed in an in vitro assay in which cultured cells are exposed to an effective concentration of said polypeptide.

In some embodiments, the polypeptide is selected such that the apparent serum binding affinity (Kd*) of the crosslinked polypeptide is 1, 3, 10, 70 micromolar or greater. In other embodiments, the Kd* of the crosslinked polypeptide is 1 to 10, 70, or 700 micromolar. In other embodiments, the crosslinked polypeptides is selected such that it possesses an estimated free fraction in human blood of between 0.1 and 50%, or between 0.15 and 10%.

The invention further provides polypeptides selected using the methods of the invention, or otherwise meeting the criteria of the invention. For example, in some embodiments, the improved cross-linked polypeptide possesses an apparent affinity to human serum proteins of 1 micromolar or weaker. In another embodiment, the improved cross-linked polypeptide possesses an apparent affinity to human serum proteins of 3 micromolar or weaker. In another embodiment, the improved cross-linked polypeptide possesses an apparent affinity to human serum proteins of 10 micromolar or weaker. In another embodiment, the improved cross-linked polypeptide possesses an apparent affinity to human serum proteins of 70 micromolar or weaker. In another embodiment, the improved cross-linked polypeptide possesses an apparent affinity to human serum proteins of between 1-70 micromolar. In another embodiment, the improved cross-linked polypeptide possesses an apparent affinity to human serum proteins of between 1-700 micromolar. In some embodiments, the improved cross-linked polypeptide possesses an estimated free fraction in whole blood of between 0.1-50%. In another embodiment, the improved cross-linked polypeptide possesses an estimated free fraction in whole blood of between 0.5-10%.

In some embodiments of the method, said polypeptide contains one crosslink. In other embodiments of the method, said polypeptide contains two cross-links.

In some embodiments of the method, one crosslink connects two α-carbon atoms. In other embodiments of the method, one α-carbon atom to which one crosslink is attached is substituted with a substituent of formula R—. In another embodiment of the method, two α-carbon atoms to which one crosslink is attached are substituted with independent substituents of formula R—.

In one embodiment of the methods of the invention, R— is alkyl. For example, R— is methyl. Alternatively, R— and any portion of one crosslink taken together can form a cyclic structure. In another embodiment of the method, one crosslink is formed of consecutive carbon-carbon bonds. For example, one crosslink may comprise at least 8, 9, 10, 11, or 12 consecutive bonds. In other embodiments, one crosslink may comprise at least 7, 8, 9, 10, or 11 carbon atoms.

In some embodiments of the method, the crosslinked polypeptide penetrates cell membranes by an energy-dependent process and binds to an intracellular target.

In another embodiment, the improved crosslinked polypeptide comprises an α-helical domain of a BCL-2 family member. For example, the crosslinked polypeptide comprises a BH3 domain. In other embodiments, the crosslinked polypeptide have a sequence identity of at least 60%, 70%, 80%, 85%, 90% or 95% to any of the sequences in Tables 1, 2, 3 and 4, e.g., as measured in a BLAST algorithm.

The invention further provides methods of using the improved crosslinked polypeptides of the invention in prophylactic and therapeutic methods of treating a subject at risk of (or susceptible to) a disorder or having a disorder associated with aberrant (e.g., insufficient or excessive) BCL-2 family member expression or activity (e.g., extrinsic or intrinsic apoptotic pathway abnormalities); and for treating or preventing hyperproliferative disease by interfering with the interaction or binding between p53 and MDM2 in hyperproliferative cells, e.g. tumor cells.

Further aspects of the invention will be apparent from the detailed description, the examples, the drawings and the claims below.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 shows a plot of cellular $EC_{50}$ vs human serum concentrations for peptidomimetic macrocycle analogs with improved properties.

DETAILED DESCRIPTION OF THE INVENTION

Figure 1:
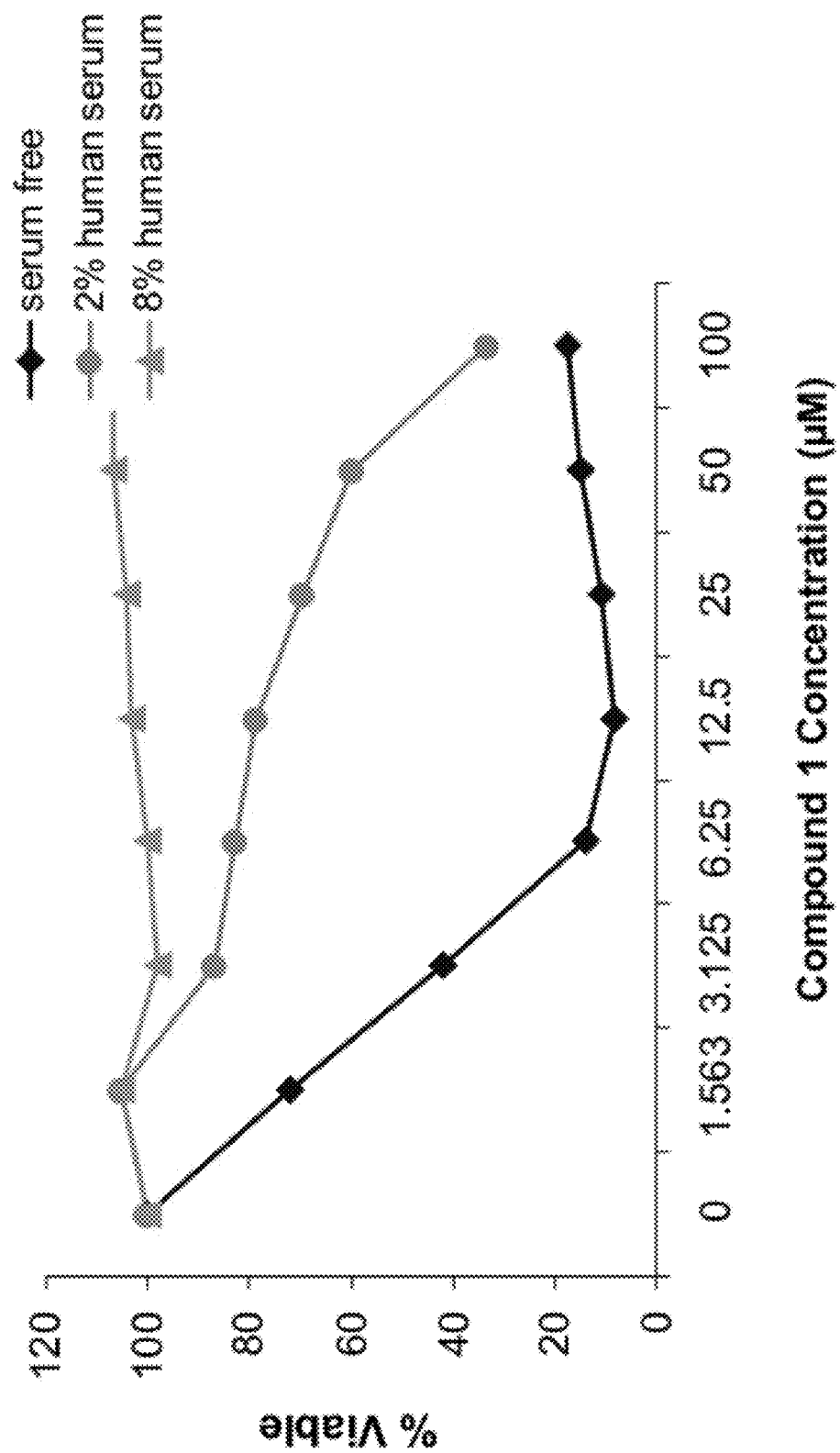
FIG. 1 shows peptidomimetic macrocycle (compound 1) dose response curves in the presence of varying concentrations of human serum.

As used herein, the term "macrocycle" refers to a molecule having a chemical structure including a ring or cycle formed by at least 9 covalently bonded atoms.

As used herein, the term "stapled polypeptide" or "crosslinked polypeptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Crosslinked polypeptide include embodiments where the macrocycle-forming linker connects the α carbon of the first amino acid residue (or analog) to the a carbon of the second amino acid residue (or analog). The crosslinked polypeptides optionally include one or more non-peptide bonds between one or more amino acid residues and/or amino acid analog residues, and optionally include one or more non-naturally-occurring amino acid residues or amino acid analog residues in addition to any which form the macrocycle.

As used herein, the term "stability" refers to the maintenance of a defined secondary structure in solution by a crosslinked polypeptide of the invention as measured by circular dichroism, NMR or another biophysical measure, or resistance to proteolytic degradation in vitro or in vivo. Non-limiting examples of secondary structures contemplated in this invention are α-helices, β-turns, and β-pleated sheets.

As used herein, the term "helical stability" refers to the maintenance of α helical structure by a crosslinked polypeptide of the invention as measured by circular dichroism or NMR. For example, in some embodiments, the crosslinked polypeptides of the invention exhibit at least a 1.25, 1.5, 1.75 or 2-fold increase in α-helicity as determined by circular dichroism compared to a corresponding macrocycle lacking the R— substituent.

The term "α-amino acid" or simply "amino acid" refers to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The term "amino acid analog" or "non-natural amino acid" refers to a molecule which is structurally similar to an amino acid and which can be substituted for an amino acid in the formation of a crosslinked polypeptide. Amino acid analogs include, without limitation, compounds which are structurally identical to an amino acid, as defined herein, except for the inclusion of one or more additional methylene groups between the amino and carboxyl group (e.g., α-amino β-carboxy acids), or for the substitution of the amino or carboxy group by a similarly reactive group (e.g., substitution of the primary amine with a secondary or tertiary amine, or substitution or the carboxy group with an ester).

A "non-essential" amino acid residue is a residue that can be altered from the wild-type sequence of a polypeptide (e.g., a BH3 domain or the p53 MDM2 binding domain) without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a BH3 polypeptide, for example, is preferably replaced with another amino acid residue from the same side chain family. Other examples of acceptable substitutions are substitutions based on isosteric considerations (e.g. norleucine for methionine) or other properties (e.g. 2-thienylalanine for phenylalanine)

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-dimethyl cyclodecane are all considered ten-membered macrocycles as the hydrogen or fluoro substituents or methyl side chains do not participate in forming the macrocycle.

The symbol " ⫽ " when used as part of a molecular structure refers to a single bond or a trans or cis double bond.

The term "amino acid side chain" refers to a moiety attached to the α-carbon in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an α,α di-substituted amino acid).

The term "α,α di-substituted amino" acid refers to a molecule or moiety containing both an amino group and a carboxyl group bound to a carbon (the α-carbon) that is attached to two natural or non-natural amino acid side chains.

The term "polypeptide" encompasses two or more naturally or non-naturally-occurring amino acids joined by a covalent bond (e.g., an amide bond). Polypeptides as described herein include full length proteins (e.g., fully processed proteins) as well as shorter amino acid sequences (e.g., fragments of naturally-occurring proteins or synthetic polypeptide fragments).

The term "macrocyclization reagent" or "macrocycle-forming reagent" as used herein refers to any reagent which may be used to prepare a crosslinked polypeptide of the invention by mediating the reaction between two reactive groups. Reactive groups may be, for example, an azide and alkyne, in which case macrocyclization reagents include, without limitation, Cu reagents such as reagents which provide a reactive Cu(I) species, such as CuBr, CuI or CuOTf, as well as Cu(II) salts such as Cu(CO$_2$CH$_3$)$_2$, CuSO$_4$, and CuCl$_2$ that can be converted in situ to an active Cu(I) reagent by the addition of a reducing agent such as ascorbic acid or sodium ascorbate. Macrocyclization reagents may additionally include, for example, Ru reagents known in the art such as Cp*RuCl(PPh$_3$)$_2$, [Cp*RuCl]$_4$ or other Ru reagents which may provide a reactive Ru(II) species. In other cases, the reactive groups are terminal olefins. In such embodiments, the macrocyclization reagents or macrocycle-forming reagents are metathesis catalysts including, but not limited to, stabilized, late transition metal carbene complex catalysts such as Group VIII transition metal carbene catalysts. For example, such catalysts are Ru and Os metal centers having a +2 oxidation state, an electron count of 16 and pentacoordinated. Additional catalysts are disclosed in Grubbs et al., "Ring Closing Metathesis and Related Processes in Organic Synthesis" Acc. Chem. Res. 1995, 28, 446-452, and U.S. Pat. No. 5,811,515. In yet other cases, the reactive groups are thiol groups. In such embodiments, the macrocyclization reagent is, for example, a linker functionalized with two thiol-reactive groups such as halogen groups.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Arylalkyl" refers to an aryl group, as defined above, wherein one of the aryl group's hydrogen atoms has been replaced with a $C_1$-$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH2-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl, "Alkylheterocycle" refers to a $C_1$-$C_5$ alkyl group, as defined above, wherein one of the $C_1$-$C_5$ alkyl group's hydrogen atoms has been replaced with a heterocycle. Representative examples of an alkylheterocycle group include, but are not limited to, —CH$_2$CH$_2$-morpholine, —CH$_2$CH$_2$-piperidine, —CH$_2$CH$_2$CH$_2$-morpholine, and —CH$_2$CH$_2$CH$_2$-imidazole.

"Alkylamido" refers to a $C_1$-$C_5$ alkyl group, as defined above, wherein one of the $C_1$-$C_5$ alkyl group's hydrogen atoms has been replaced with a —C(O)NH$_2$ group. Representative examples of an alkylamido group include, but are not limited to, —CH$_2$—C(O)NH$_2$, —CH$_2$CH$_2$—C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)CH$_2$CH$_3$, —C(CH$_3$)$_2$CH$_2$C(O)NH$_2$, —CH$_2$—CH$_2$—NH—C(O)—CH$_3$, —CH$_2$—CH$_2$—NH—C(O)—CH$_3$—CH$_3$, and —CH$_2$—CH$_2$—NH—C(O)—CH=CH$_2$.

"Alkanol" refers to a $C_1$-$C_5$ alkyl group, as defined above, wherein one of the $C_1$-$C_5$ alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$ CH$_2$CH$_2$OH, —CH$_2$CH(OH)CH$_3$, —CH$_2$CH(OH)CH$_2$CH$_3$, —CH(OH)CH$_3$ and —C(CH$_3$)$_2$CH$_2$OH.

"Alkylcarboxy" refers to a $C_1$-$C_5$ alkyl group, as defined above, wherein one of the $C_1$-$C_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent.

Examples of heterocyclyl groups include piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included in the present invention unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included in the present invention unless expressly provided otherwise. All crystal forms of the compounds described herein are included in the present invention unless expressly provided otherwise.

As used herein, the terms "increase" and "decrease" mean, respectively, to cause a statistically significantly (i.e., p<0.1) increase or decrease of at least 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

The term "on average" represents the mean value derived from performing at least three independent replicates for each data point.

The term "biological activity" encompasses structural and functional properties of a macrocycle of the invention. Biological activity is, for example, structural stability, alpha-helicity, affinity for a target, resistance to proteolytic degradation, cell penetrability, intracellular stability, in vivo stability, or any combination thereof.

The details of one or more particular embodiments of the invention are set forth in the accompanying drawings and the description below. Other features, objects, and advantages of the invention will be apparent from the description and drawings, and from the claims.

Biological Properties of the Crosslinked Polypeptides of the Invention

In one embodiment, the present invention provides a method of identifying cross-linked polypeptides with improved efficacies in human whole blood, comprising the steps of synthesizing analogs of the parent cross-linked polypeptide and performing cellular assays in the absence of human serum proteins and also in the presence of two or more concentrations of human serum, so as to determine the apparent affinity of each cross-linked polypeptide for human serum proteins and to calculate an EC50 in whole blood by mathematical extrapolation.

In some embodiments, the polypeptide is selected such that the apparent serum binding affinity (Kd*) of the crosslinked polypeptide is 1, 3, 10, 70 micromolar or greater. In other embodiments, the Kd* of the crosslinked polypeptide is 1 to 10, 70, or 700 micromolar. In other embodiments, the crosslinked polypeptides are selected such that it possesses an estimated free fraction in human blood of between 0.1 and 50%, or between 0.15 and 10%.

In some embodiments, the apparent Kd values for serum protein by EC50 shift analysis is used to provide a simple and rapid means of quantifying the propensity of experimental compounds to bind HSA and other serum proteins. A linear relationship exists between the apparent $EC_{50}$ in the presence of serum protein ($EC'_{50}$) and the amount of serum protein added to an in vitro assay. This relationship is defined by the binding affinity of the compound for serum proteins, expressed as $K_d^*$. This term is an experimentally determined, apparent dissociation constant that may result from the cumulative effects of multiple, experimentally indistinguishable, binding events. The form of this relationship is presented here in Eq. 0.1, and its derivation can be found in Copeland et al, Biorg. Med Chem Lett. 2004, 14:2309-2312, the contents of which are incorporated herein by reference.

$$EC'_{50} = EC_{50} + P\left(\frac{n}{1 + \frac{K_d^*}{EC_{50}}}\right) \quad (0.1)$$

A significant proportion of serum protein binding can be ascribed to drug interactions with HSA, due to the very high concentration of this protein in serum (35-50 g/L or 530-758 μM). To calculate the $K_d$ value for these compounds we have assumed that the shift in $EC_{50}$ upon protein addition can be ascribed fully to the HSA present in the added serum, where P is 700 μM for 100% serum, P is 70 μM for 10% serum, etc. We further make the simplifying assumption that all of the compounds bind HSA with a 1:1 stoichiometry, so that the term n in Eq. (0.1) is fixed at unity. With these parameters in place we calculate the $K_d^*$ value for each stapled peptide from the changes in $EC_{50}$ values with increasing serum (and serum protein) concentrations by nonlinear regression analysis of Eq. 1.1 using Mathematica 4.1 (Wolfram Research, Inc., www.wolfram.com). The free fraction in blood is estimated per the following equation, where $[HSA]_{total}$ is set at 700 μM, as derived by Trainor, Expert Opin. Drug Disc., 2007, 2(1):51-64, the contents of which are incorporated herein by reference.

$$FreeFraction = \frac{K_d^*}{K_d^* + [HSA]_{total}} \quad (0.2)$$

In one embodiment, the improved biological activity is measured as increased cell penetrability or an increased ability to induce apoptosis. In yet other embodiments, the biological activity is measured as the percentage of the number of cells killed in an in vitro assay in which cultured cells are exposed to an effective concentration of said polypeptide.

In some embodiments, the improved cross-linked polypeptide possesses an apparent affinity to human serum proteins of 1 micromolar or weaker. In another embodiment, the improved cross-linked polypeptide possesses an apparent affinity to human serum proteins of 3 micromolar or weaker. In another embodiment, the improved cross-linked polypeptide possesses an apparent affinity to human serum proteins of 10 micromolar or weaker. In another embodiment, the improved cross-linked polypeptide possesses an apparent affinity to human serum proteins of 70 micromolar or weaker. In another embodiment, the improved cross-linked polypeptide possesses an apparent affinity to human serum proteins of between 1-70 micromolar. In another embodiment, the improved cross-linked polypeptide possesses an apparent affinity to human serum proteins of between 1-700 micromolar.

In some embodiments, the improved cross-linked polypeptide possesses an estimated free fraction in whole blood of between 0.1-50%. In another embodiment, the improved cross-linked polypeptide possesses an estimated free fraction in whole blood of between 0.5-10%.

Crosslinked Polypeptides of the Invention

Any protein or polypeptide with a known primary amino acid sequence which contains a secondary structure believed to impart biological activity by interaction with an intracellular protein, protein domain or nucleic acid target(s) is the subject of the present invention. For example, the sequence of the polypeptide can be analyzed and amino acid analogs containing groups reactive with macrocyclization reagents can be substituted at the appropriate positions. The appropriate positions are determined by ascertaining which molecular surface(s) of the secondary structure is (are) required for biological activity and, therefore, across which other surface(s) the macrocycle forming linkers of the invention can form a macrocycle without sterically blocking the surface(s) required for biological activity. Such determinations are made using methods such as X-ray crystallography of complexes between the secondary structure and a natural binding partner to visualize residues (and surfaces) critical for activity; by sequential mutagenesis of residues in the secondary structure to functionally identify residues (and surfaces) critical for activity; or by other methods. By such determinations, the appropriate amino acids are substituted with the amino acids analogs and macrocycle-forming linkers of the invention. For example, for an α-helical secondary structure, one surface of the helix (e.g., a molecular surface extending longitudinally along the axis of the helix and radially 45-135° about the axis of the helix) may be required to make contact with another biomolecule in vivo or in vitro for biological activity. In such a case, a macrocycle-forming linker is designed to link two α-carbons of the helix while extending longitudinally along the surface of the helix in the portion of that surface not directly required for activity.

In some embodiments of the invention, the peptide sequence is derived from the BCL-2 family of proteins. The BCL-2 family is defined by the presence of up to four conserved BCL-2 homology (BH) domains designated BH1, BH2, BH3, and BH4, all of which include α-helical segments (Chittenden et al. (1995), EMBO 14:5589; Wang et al. (1996), Genes Dev. 10:2859). Anti-apoptotic proteins, such as BCL-2 and BCL-$X_L$, display sequence conservation in all BH domains. Pro-apoptotic proteins are divided into "multidomain" family members (e.g., BAK, BAX), which possess homology in the BH1, BH2, and BH3 domains, and "BH3-domain only" family members (e.g., BID, BAD, BIM, BIK, NOXA, PUMA), that contain sequence homology exclusively in the BH3 amphipathic α-helical segment. BCL-2 family members have the capacity to form homo- and heterodimers, suggesting that competitive binding and the ratio between pro- and anti-apoptotic protein levels dictates susceptibility to death stimuli. Anti-apoptotic proteins function to protect cells from pro-apoptotic excess, i.e., excessive programmed cell death. Additional "security" measures include regulating transcription of pro-apoptotic proteins and maintaining them as inactive conformers, requiring either proteolytic activation, dephosphorylation, or ligand-induced conformational change to activate pro-death functions. In certain cell types, death signals received at the plasma membrane trigger apoptosis via a mitochondrial pathway. The mitochondria can serve as a gatekeeper of cell death by sequestering cytochrome c, a critical component of a cytosolic complex which activates caspase 9, leading to fatal downstream proteolytic events. Multidomain proteins such as BCL-2/BCL-$X_L$ and BAK/BAX play dueling roles of guardian and executioner at the mitochondrial membrane, with their activities further regulated by upstream BH3-only members of the BCL-2 family. For example, BID is a member of the BH3-domain only family of pro-apoptotic proteins, and transmits death signals received at the plasma membrane to effector pro-apoptotic proteins at the mitochondrial membrane. BID has the capability of interacting with both pro- and anti-apoptotic proteins, and upon activation by caspase 8, triggers cytochrome c release and mitochondrial apoptosis. Deletion and mutagenesis studies determined that the amphipathic α-helical BH3 segment of pro-apoptotic family members may function as a death domain and thus may represent a critical structural motif for interacting with multidomain apoptotic proteins. Structural studies have shown that the BH3 helix can interact with anti-apoptotic proteins by inserting into a hydrophobic groove formed by the interface of BH1, 2 and 3 domains. Activated BID can be bound and sequestered by anti-apoptotic proteins (e.g., BCL-2 and BCL-$X_L$) and can trigger activation of the pro-apoptotic proteins BAX and BAK, leading to cytochrome c release and a mitochondrial apoptosis program. BAD is also a BH3-domain only pro-apoptotic family member whose expression triggers the activation of BAX/BAK. In contrast to BID, however, BAD displays preferential binding to anti-apoptotic family members, BCL-2 and BCL-$X_L$. Whereas the BAD BH3 domain exhibits high affinity binding to BCL-2, BAD BH3 peptide is unable to activate cytochrome c release from mitochondria in vitro, suggesting that BAD is not a direct activator of BAX/BAK. Mitochondria that over-express BCL-2 are resistant to BID-induced cytochrome c release, but co-treatment with BAD can restore BID sensitivity. Induction of mitochondrial apoptosis by BAD appears to result from either: (1) displacement of BAX/BAK activators, such as BID and BID-like proteins, from the BCL-2/BCL-XL binding pocket, or (2) selective occupation of the BCL-2/BCL-XL binding pocket by BAD to prevent sequestration of BID-like proteins by anti-apoptotic proteins. Thus, two classes of BH3-domain only proteins have emerged, BID-like proteins that directly activate mitochondrial apoptosis, and BAD-like proteins, that have the capacity to sensitize mitochondria to BID-like pro-apoptotics by occupying the binding pockets of multidomain anti-apoptotic proteins. Various α-helical domains of BCL-2 family member proteins amendable to the methodology disclosed herein have been disclosed (Walensky et al. (2004), Science 305:1466; and Walensky et al., U.S. Patent Publication No. 2005/0250680, the entire disclosures of which are incorporated herein by reference).

In other embodiments, the peptide sequence is derived from the tumor suppressor p53 protein which binds to the oncogene protein MDM2. The MDM2 binding site is localized within a region of the p53 tumor suppressor that forms an a helix. In U.S. Pat. No. 7,083,983, the entire contents of which are incorporated herein by reference, Lane et al. disclose that the region of p53 responsible for binding to MDM2 is represented approximately by amino acids 13-31 (PLSQETFSDLWKLLPENNV (SEQ ID NO: 1)) of mature human P53 protein. Other modified sequences disclosed by Lane are also contemplated in the instant invention. Furthermore, the interaction of p53 and MDM2 has been discussed by Shair et al. (1997), *Chem. & Biol.* 4:791, the entire contents of which are incorporated herein by reference, and mutations in the p53 gene have been identified in virtually half of all reported cancer cases. As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic α-helix of 2.5 turns that inserts into the MDM2 crevice. Thus, in some embodiments, novel α-helix structures generated by the method of the present invention are engineered to generate structures that bind tightly to the helix acceptor and disrupt native protein-protein interactions. These structures are then screened using high throughput techniques to identify optimal small molecule peptides. The novel structures that disrupt the MDM2 interaction are useful for many applications, including, but not limited to, control of soft tissue sarcomas (which overexpresses MDM2 in the presence of wild type p53). These cancers are then, in some embodiments, held in check with small molecules that intercept MDM2, thereby preventing suppression of p53. Additionally, in some embodiments, small molecules disrupters of MDM2-p53 interactions are used as adjuvant therapy to help control and modulate the extent of the p53 dependent apoptosis response in conventional chemotherapy.

A non-limiting exemplary list of suitable peptide sequences for use as a starting point for optimization in accordance with the present invention is given below:

TABLE 1

| Name | Sequence (bold = critical residues) | SEQ ID NO: | Cross-linked Sequence (X = x-link residue) | SEQ ID NO: |
|---|---|---|---|---|
| BH3 peptides | | | | |
| BID-BH3 | QEDIIRNIARHLAQVGDSMDRSIPP | 2 | QEDIIRNIARHLAXVGDXMDRSIPP | 25 |
| BIM-BH3 | DNRPEIWIAQELRRIGDEFNAYYAR | 3 | DNRPEIWIAQELRXIGDXFNAYYAR | 26 |
| BAD-BH3 | NLWAAQRYGRELRRMSDEFVDSFKK | 4 | NLWAAQRYGRELRXMSDXFVDSFKK | 27 |
| PUMA-BH3 | EEQWAREIGAQLRRMADDLNAQYER | 5 | EEQWAREIGAQLRXMADXLNAQYER | 28 |
| Hrk-BH3 | RSSAAQLTAARLKALGDELHQRTM | 6 | RSSAAQLTAARLKXLGDXLHQRTM | 29 |
| NOXAA-BH3 | AELPPEFAAQLRKIGDKVYCTW | 7 | AELPPEFAAQLRXIGDXVYCTW | 30 |
| NOXAB-BH3 | VPADLKDECAQLRRIGDKVNLRQKL | 8 | VPADLKDECAQLRXIGDXVNLRQKL | 31 |
| BMF-BH3 | QHRAEVQIARKLQCIADQFHRLHT | 9 | QHRAEVQIARKLQXIADXFHRLHT | 32 |
| BLK-BH3 | SSAAQLTAARLKALGDELHQRT | 10 | SSAAQLTAARLKXLGDXLHQRT | 33 |
| BIK-BH3 | CMEGSDALALRLACIGDEMDVSLRA | 11 | CMEGSDALALRLAXIGDXMDVSLRA | 34 |
| Bnip3 | DIERRKEVESILKKNSDWIWDWSS | 12 | DIERRKEVESILKXNSDXIWDWSS | 35 |
| BOK-BH3 | GRLAEVCAVLLRLGDELEMIRP | 13 | GRLAEVCAVLLXLGDXLEMIRP | 36 |
| BAX-BH3 | PQDASTKKSECLKRIGDELDSNMEL | 14 | PQDASTKKSECLKXIGDXLDSNMEL | 37 |
| BAK-BH3 | PSSTMGQVGRQLAIIGDDINRR | 15 | PSSTMGQVGRQLAXIGDXINRR | 38 |
| BCL2L1-BH3 | KQALREAGDEFELR | 16 | KQALRXAGDXFELR | 39 |
| BCL2-BH3 | LSPPVVHLALALRQAGDDFSRR | 17 | LSPPVVHLALALRXAGDXFSRR | 40 |
| BCL-XL-BH3 | EVIPMAAVKQALREAGDEFELRY | 18 | EVIPMAAVKQALRXAGDXFELRY | 41 |
| BCL-W-BH3 | PADPLHQAMRAAGDEFETRF | 19 | PADPLHQAMRXAGDXFETRF | 42 |
| MCL1-BH3 | ATSRKLETLRRVGDGVQRNHETA | 20 | ATSRKLETLRXVGDXVQRNHETA | 43 |
| MTD-BH3 | LAEVCTVLLRLGDELEQIR | 21 | LAEVCTVLLXLGDXLEQIR | 44 |
| MAP-1-BH3 | MTVGELSRALGHENGSLDP | 22 | MTVGELSRALGXENGXLDP | 45 |
| NIX-BH3 | WEGEKEVEALKKSADWVSDWS | 23 | WEGEKEVEALKXSADXVSDWS | 46 |
| 4ICD(ERBB4)-BH3 | SMARDPQRYLVIQGDDRMKL | 24 | SMARDPQRYLVXQGDXRMKL | 47 |

Table 1 lists human sequences which target the BH3 binding site and are implicated in cancers, autoimmune disorders, metabolic diseases and other human disease conditions.

TABLE 2

| Name | Sequence (bold = critical residues) | SEQ ID NO: | Cross-linked Sequence (X = x-link residue) | SEQ ID NO: |
|---|---|---|---|---|
| BH3 peptides | | | | |
| BID-BH3 | QEDIIRNIARHLAQVGDSMDRSIPP | 2 | QEDIIRNIXRHLXQVGDSMDRSIPP | 48 |
| BIM-BH3 | DNRPEIWIAQELRRIGDEFNAYYAR | 3 | DNRPEIWIXQELXRIGDEFNAYYAR | 49 |
| BAD-BH3 | NLWAAQRYGRELRRMSDEFVDSFKK | 4 | NLWAAQRYXRELXRMSDEFVDSFKK | 50 |
| PUMA-BH3 | EEQWAREIGAQLRRMADDLNAQYER | 5 | EEQWAREIXAQLXRMADDLNAQYER | 51 |
| Hrk-BH3 | RSSAAQLTAARLKALGDELHQRTM | 6 | RSSAAQLTXARLXALGDELHQRTM | 52 |
| NOXAA-BH3 | AELPPEFAAQLRKIGDKVYCTW | 7 | AELPPEFXAQLXKIGDKVYCTW | 53 |
| NOXAB-BH3 | VPADLKDECAQLRRIGDKVNLRQKL | 8 | VPADLKDEXAQLXRIGDKVNLRQKL | 54 |
| BMF-BH3 | QHRAEVQIARKLQCIADQFHRLHT | 9 | QHRAEVQIXRKLXCIADQFHRLHT | 55 |
| BLK-BH3 | SSAAQLTAARLKALGDELHQRT | 10 | SSAAQLTXARLXALGDELHQRT | 56 |
| BIK-BH3 | CMEGSDALALRLACIGDEMDVSLRA | 11 | CMEGSDALXLRLXCIGDEMDVSLRA | 57 |
| Bnip3 | DIERRKEVESILKKNSDWIWDWSS | 12 | DIERRKEVXSILXKNSDWIWDWSS | 58 |
| BOK-BH3 | GRLAEVCAVLLRLGDELEMIRP | 13 | GRLAEVXAVLXRLGDELEMIRP | 59 |
| BAX-BH3 | PQDASTKKSECLKRIGDELDSNMEL | 14 | PQDASTKKXECLXRIGDELDSNMEL | 60 |
| BAK-BH3 | PSSTMGQVGRQLAIIGDDINRR | 15 | PSSTMGQVXRQLXIIGDDINRR | 61 |
| BCL2L1-BH3 | KQALREAGDEFELR | 16 | XQALXEAGDEFELR | 62 |
| BCL2-BH3 | LSPPWHLALALRQAGDDFSRR | 17 | LSPPWHLXLALXQAGDDFSRR | 63 |
| BCL-XL-BH3 | EVIPMAAVKQALREAGDEFELRY | 18 | EVIPMAAVXQALXEAGDEFELRY | 64 |
| BCL-W-BH3 | PADPLHQAMRAAGDEFETRF | 19 | PADPLXQAMXAAGDEFETRF | 65 |
| MCL1-BH3 | ATSRKLETLRRVGDGVQRNHETA | 20 | ATSRKXETLXRVGDGVQRNHETA | 66 |
| MTD-BH3 | LAEVCTVLLRLGDELEQIR | 21 | LAEVXTVLXRLGDELEQIR | 67 |
| MAP-1-BH3 | MTVGELSRALGHENGSLDP | 22 | MTVGELXRALXHENGSLDP | 68 |
| NIX-BH3 | WEGEKEVEALKKSADWVSDWS | 23 | WEGEKEXEALXKSADWVSDWS | 69 |
| 4ICD(ERBB4)-BH3 | SMARDPQRYLVIQGDDRMKL | 24 | SMARDPXRYLXIQGDDRMKL | 70 |

Table 2 lists human sequences which target the BH3 binding site and are implicated in cancers, autoimmune disorders, metabolic diseases and other human disease conditions.

TABLE 3

| Name | Sequence (bold = critical residues) | SEQ ID NO: | Cross-linked Sequence (X = x-link residue) | SEQ ID NO: |
|---|---|---|---|---|
| P53 peptides | | | | |
| hp53 peptide 1 | LSQETFSDLWKLLPEN | 71 | LSQETFSDXWKLLPEX | 72 |
| hp53 peptide 2 | LSQETFSDLWKLLPEN | 71 | LSQEXFSDLWKXLPEN | 73 |
| hp53 peptide 3 | LSQETFSDLWKLLPEN | 71 | LSQXTFSDLWXLLPEN | 74 |
| hp53 peptide 4 | LSQETFSDLWKLLPEN | 71 | LSQETFXDLWKLLXEN | 75 |
| hp53 peptide 5 | LSQETFSDLWKLLPEN | 71 | QSQQTFXNLWRLLXQN | 76 |

Table 3 lists human sequences which target the p53 binding site of MDM2/X and are implicated in cancers.

TABLE 4

| Name | Sequence (bold = critical residues) | SEQ ID NO: | Cross-linked Sequence (X = x-link residue) | SEQ ID NO: |
|---|---|---|---|---|
| GPCR peptide ligands | | | | |
| Angiotensin II | DRVYIHPF | 77 | DRXYXHPF | 83 |
| Bombesin | EQRLGNQWAVGHLM | 78 | EQRLGNXWAVGHLX | 84 |
| Bradykinin | RPPGFSPFR | 79 | RPPXFSPFRX | 85 |
| C5a | ISHKDMQLGR | 80 | ISHKDMXLGRX | 86 |
| C3a | ARASHLGLAR | 81 | ARASHLXLARX | 87 |
| α-melanocyte stimulating hormone | SYSMEHFRWGKPV | 82 | SYSMXHFRWXKPV | 88 |

Table 4 lists sequences which target human G protein-coupled receptors and are implicated in numerous human disease conditions (Tyndall et al. (2005), *Chem. Rev.* 105: 793-826).

Crosslinked Polypeptides of the Invention

In some embodiments of the method, a polypeptide of the invention contains one crosslink. In other embodiments of the method, said polypeptide contains two cross-links. In some embodiments of the method, one crosslink connects two α-carbon atoms. In other embodiments of the method, one α-carbon atom to which one crosslink is attached is substituted with a substituent of formula R—. In another embodiment of the method, two α-carbon atoms to which one crosslink is attached are substituted with independent substituents of formula R—. In one embodiment of the methods of the invention, R— is alkyl. For example, R— is methyl. Alternatively, R— and any portion of one crosslink taken together can form a cyclic structure. In another embodiment of the method, one crosslink is formed of consecutive carbon-carbon bonds. For example, one crosslink may comprise at least 8, 9, 10, 11, or 12 consecutive bonds. In other embodiments, one crosslink may comprise at least 7, 8, 9, 10, or 11 carbon atoms.

In another embodiment of the method, the crosslinked polypeptide comprises an α-helical domain of a BCL-2 family member. For example, the crosslinked polypeptide comprises a BH3 domain. In other embodiments, the crosslinked polypeptide comprises at least 60%, 70%, 80%, 85%, 90% or 95% of any of the sequences in Tables 1, 2, 3 and 4. In some embodiments of the method, the crosslinked polypeptide penetrates cell membranes by an energy-dependent process and binds to an intracellular target.

In some embodiments, said helical polypeptide contains one crosslink. In other embodiments, said helical polypeptide contains two cross-links.

In some embodiments, one crosslink connects two α-carbon atoms. In other embodiments, one α-carbon atom to which one crosslink is attached is substituted with a substituent of formula R—. In another embodiment, two α-carbon atoms to which one crosslink is attached are substituted with independent substituents of formula R—. In one embodiment of the invention, R— is alkyl. For example, R— is methyl. Alternatively, R— and any portion of one crosslink taken together can form a cyclic structure. In another embodiment, one crosslink is formed of consecutive carbon-carbon bonds. For example, one crosslink may comprise at least 8, 9, 10, 11, or 12 consecutive bonds. In other embodiments, one crosslink may comprise at least 7, 8, 9, 10, or 11 carbon atoms.

In another embodiment, the crosslinked polypeptide comprises an α-helical domain of a BCL-2 family member. For example, the crosslinked polypeptide comprises a BH3 domain. In other embodiments, the crosslinked polypeptide comprises at least 60%, 70%, 80%, 85%, 90% or 95% of any of the sequences in Tables 1, 2, 3 and 4. In some embodiments, the crosslinked polypeptide penetrates cell membranes by an energy-dependent process and binds to an intracellular target.

In some embodiments, the crosslinked polypeptides of the invention have the Formula (I):

Formula I

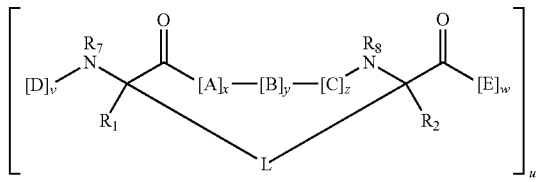

Formula (I)

wherein:

each A, C, D, and E is independently a natural or non-natural amino acid;

B is a natural or non-natural amino acid, amino acid analog,

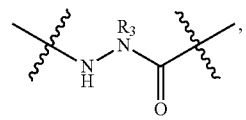

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

L is a macrocycle-forming linker of the formula -$L_1$-$L_2$-;

$L_1$ and $L_2$ are independently alkylene, alkenylene, alkynylene, heteroalkylene, cycloalkylene, heterocycloalkylene, cycloarylene, heteroarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

u is an integer from 0-10;
v is an integer from 1-1000;
w is an integer from 1-1000;
x is an integer from 0-10;
y is an integer from 0-10;
z is an integer from 0-10; and
n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments of the invention, x+y+z is at least 3. In other embodiments of the invention, x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula $[A]_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the crosslinked polypeptide of the invention comprises a secondary structure which is an α-helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

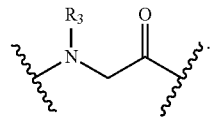

In other embodiments, the length of the macrocycle-forming linker L as measured from a first Cα to a second Cα is selected to stabilize a desired secondary peptide structure, such as an α-helix formed by residues of the crosslinked polypeptide including, but not necessarily limited to, those between the first Cα to a second Cα.

In one embodiment, the crosslinked polypeptide of Formula (I) is:

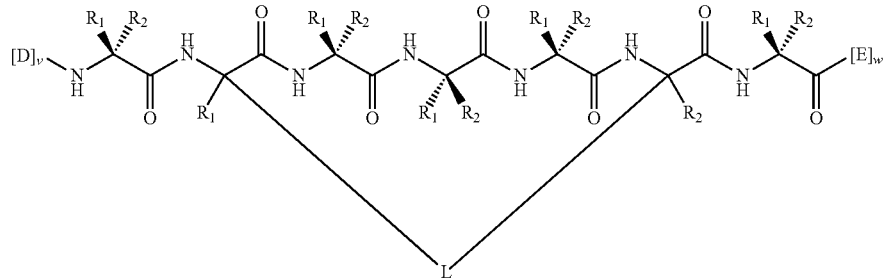

wherein each $R_1$ and $R_2$ is independently independently —H, alkyl, alkenyl, alkynyl, arylalkyl, cycloalkyl, cycloalkylalkyl, heteroalkyl, or heterocycloalkyl, unsubstituted or substituted with halo-.

In related embodiments, the crosslinked polypeptide of Formula (I) is:

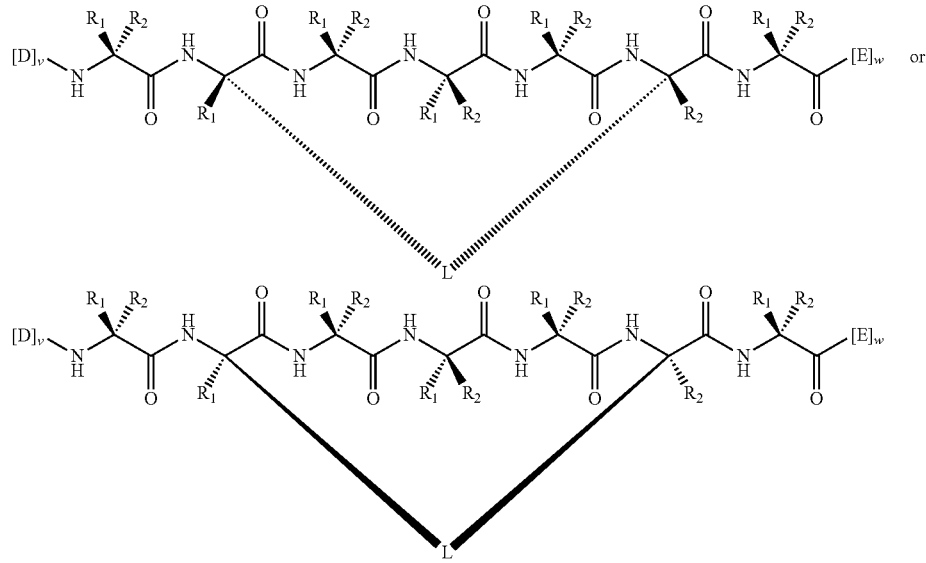

In other embodiments, the peptidomimetic macrocycle of Formula (I) is a compound of any of the formulas shown below:
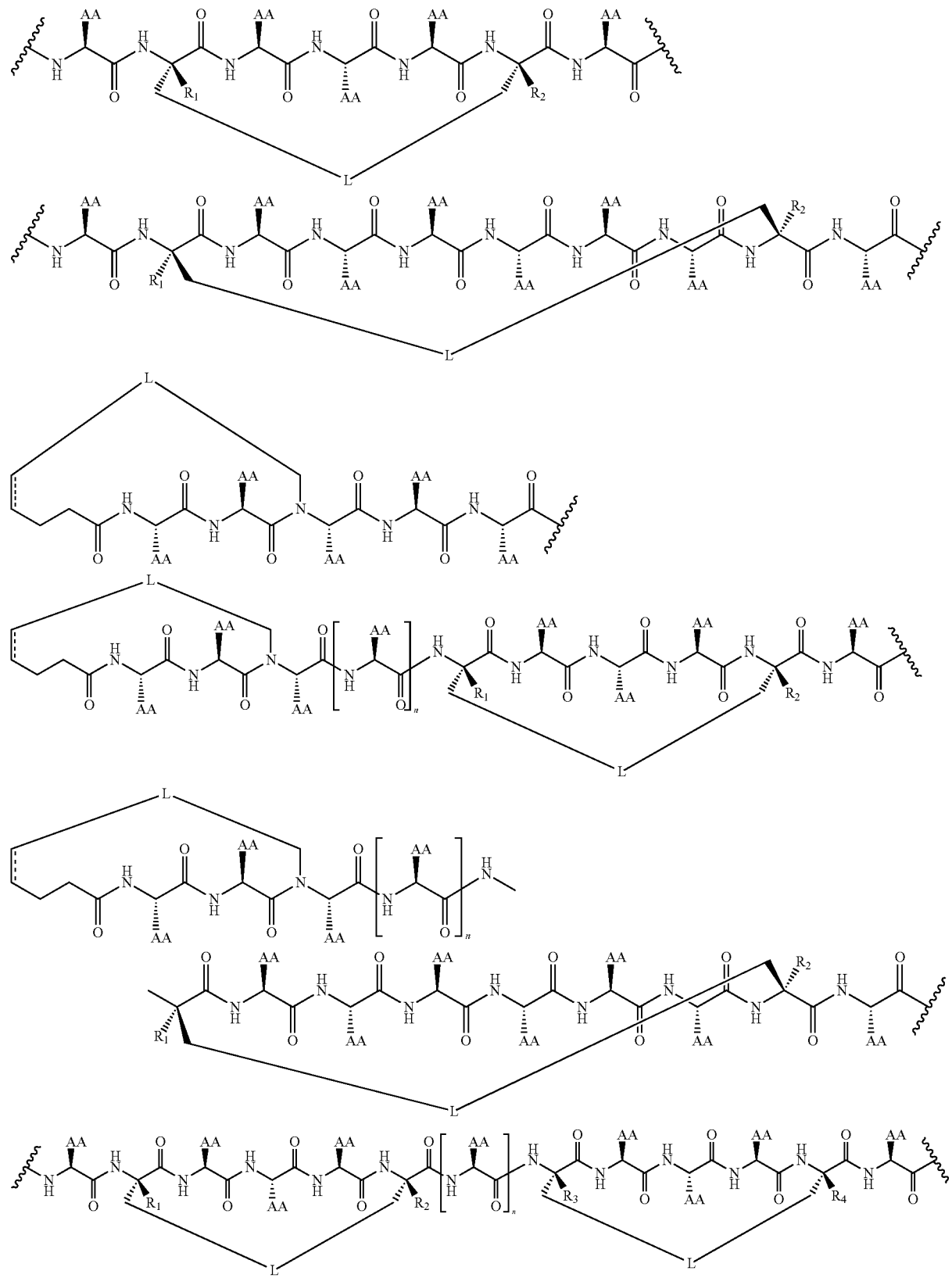

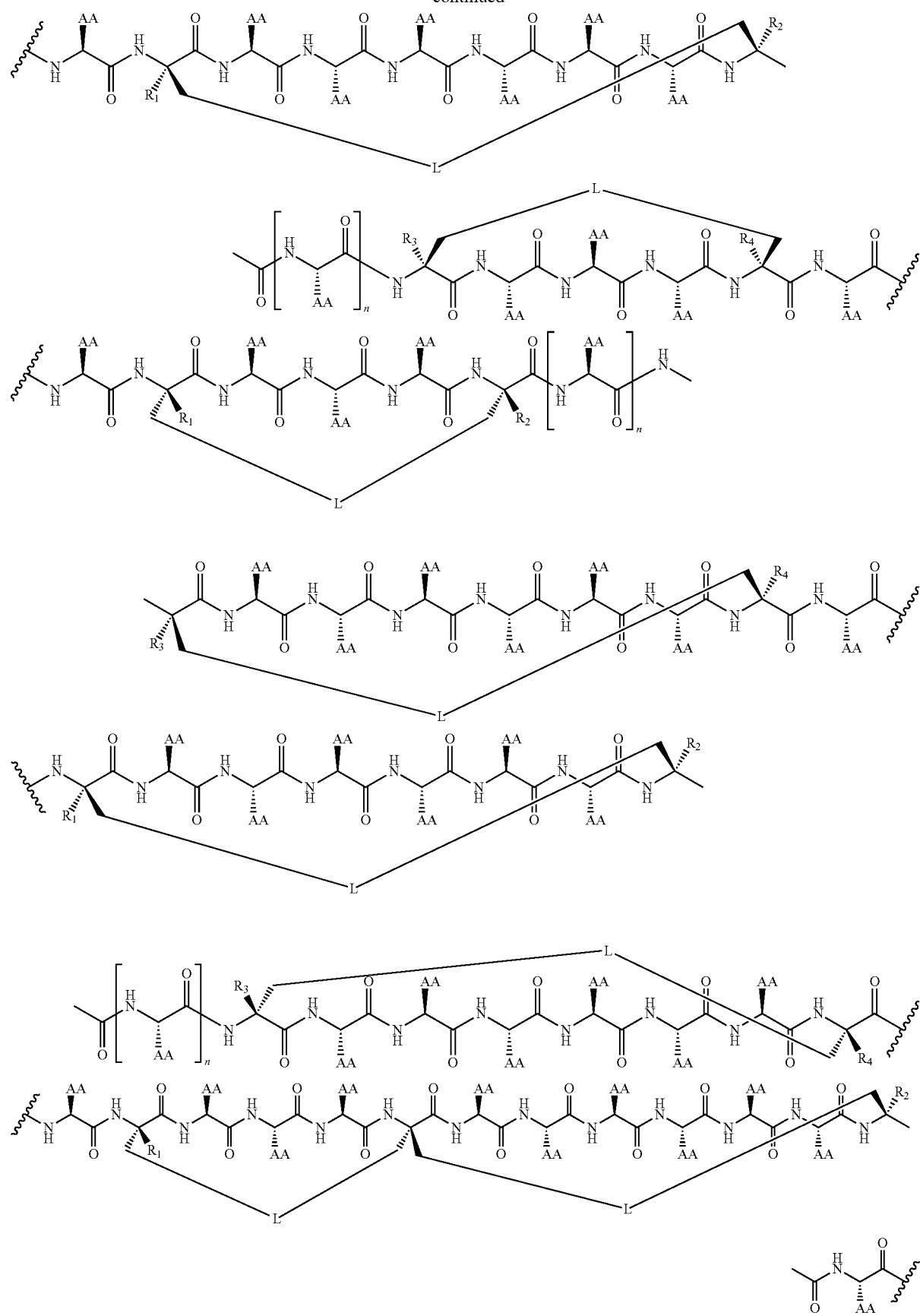

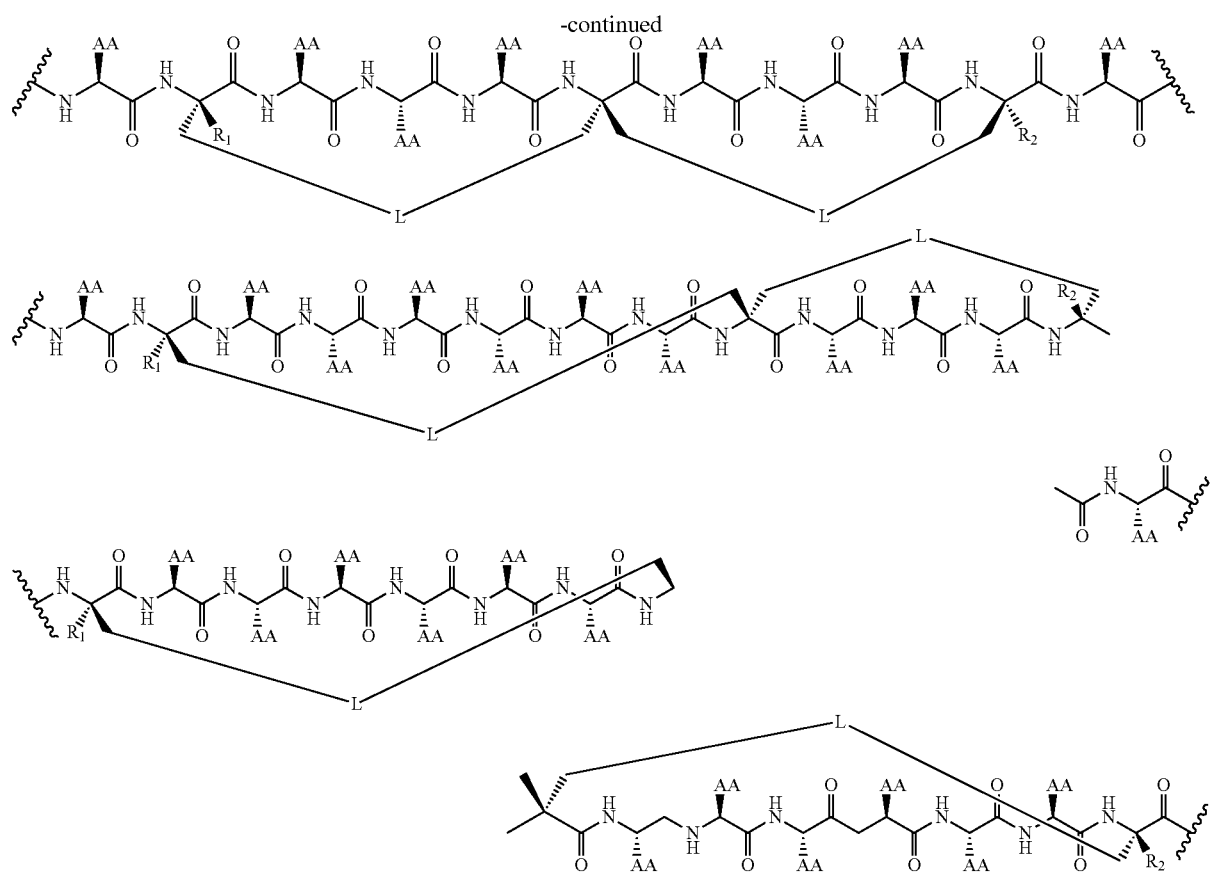

wherein "AA" represents any natural or non-natural amino acid side chain and "⚡" is $[D]_v$, $[E]_w$ as defined above, and n is an integer between 0 and 20, 50, 100, 200, 300, 400 or 500. In some embodiments, n is 0. In other embodiments, n is less than 50.

Exemplary embodiments of the macrocycle-forming linker L are shown below.

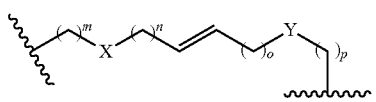

where X, Y = —CH$_2$—, O, S, or NH
m, n, o, p = 0-10

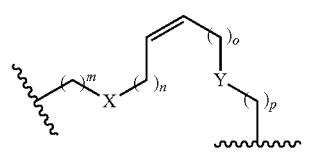

where X, Y = —CH$_2$—, O, S, or NH
m, n, o, p = 0-10

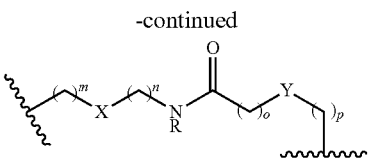

where X, Y = —CH$_2$—, O, S, or NH
m, n, o, p = 0-10
R = H, alkyl, other substituent

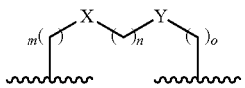

where X, Y = —CH$_2$—, O, S, or NH
m, n, o = 0-10

In some embodiments, the crosslinked polypeptides of the invention have the Formula (II):

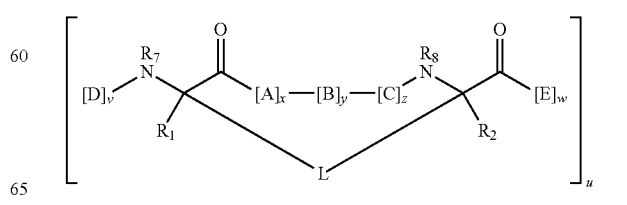

Formula (II)

wherein:
each A, C, D, and E is independently a natural or non-natural amino acid;
B is a natural or non-natural amino acid, amino acid analog,

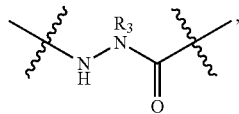

[—NH-L$_3$-CO—], [—NH-L$_3$-SO$_2$—], or [—NH-L$_3$-];
R$_1$ and R$_2$ are independently —H, alkyl, alkenyl, alkynyl, arylalkyl, cycloalkyl, cycloalkylalkyl, heteroalkyl, or heterocycloalkyl, unsubstituted or substituted with halo-;
R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;
L is a macrocycle-forming linker of the formula

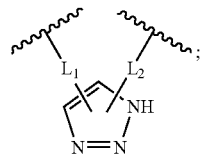

L$_1$, L$_2$ and L$_3$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;
each R$_4$ is alkylene, alkenylene, alkynylene, heteroalkylene, cycloalkylene, heterocycloalkylene, arylene, or heteroarylene;
each K is O, S, SO, SO$_2$, CO, CO$_2$, or CONR$_3$;
each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;
each R$_6$ is independently —H, alkyl, alkenyl, alkynyl, arylalkyl, cycloalkylalkyl, heterocycloalkyl, a fluorescent moiety, a radioisotope or a therapeutic agent;
R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with a D residue;
R$_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with an E residue;
u is an integer from 0-10;
v is an integer from 1-1000;
w is an integer from 1-1000;
x is an integer from 0-10;
y is an integer from 0-10;
z is an integer from 0-10; and
n is an integer from 1-5.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments of the invention, x+y+z is at least 3. In other embodiments of the invention, x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the crosslinked polypeptide of the invention comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

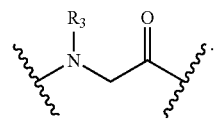

In other embodiments, the length of the macrocycle-forming linker L as measured from a first Cα to a second Cα is selected to stabilize a desired secondary peptide structure, such as an α-helix formed by residues of the crosslinked polypeptide including, but not necessarily limited to, those between the first Cα to a second Cα.

Exemplary embodiments of the macrocycle-forming linker L are shown below.

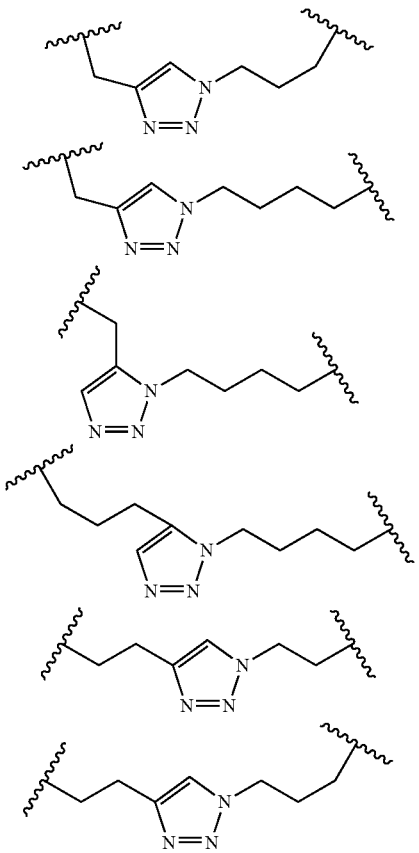

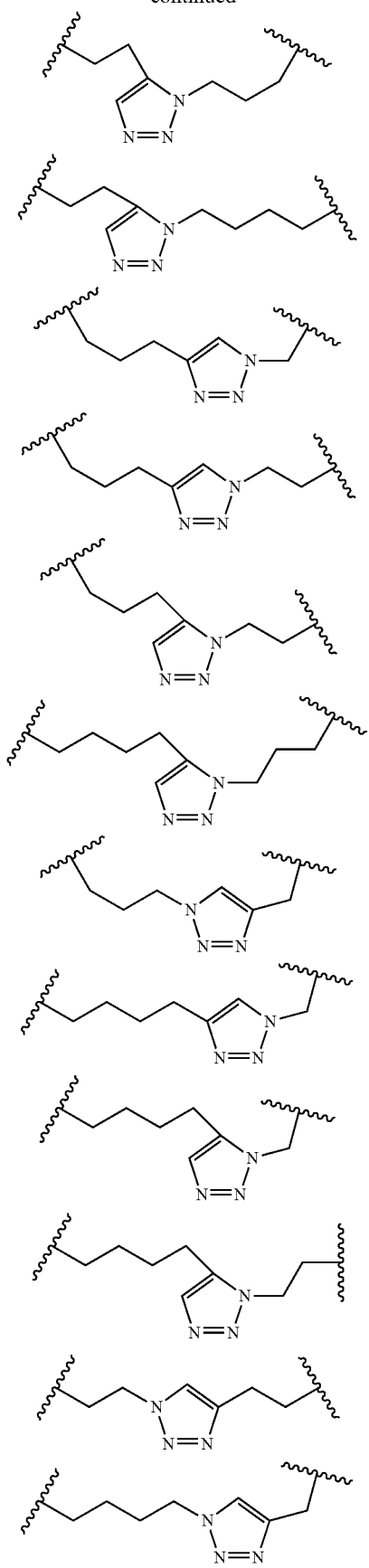
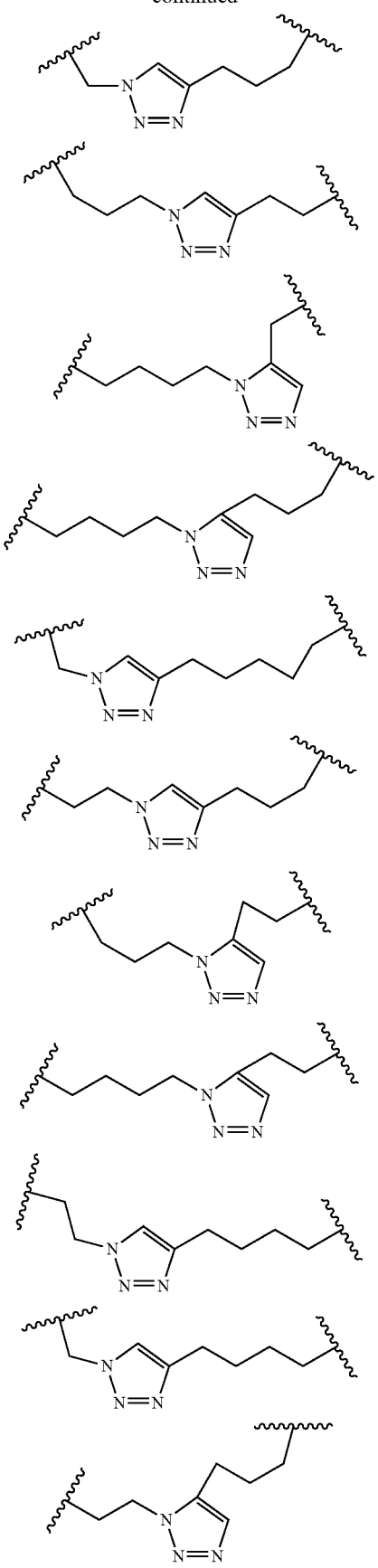

31
-continued
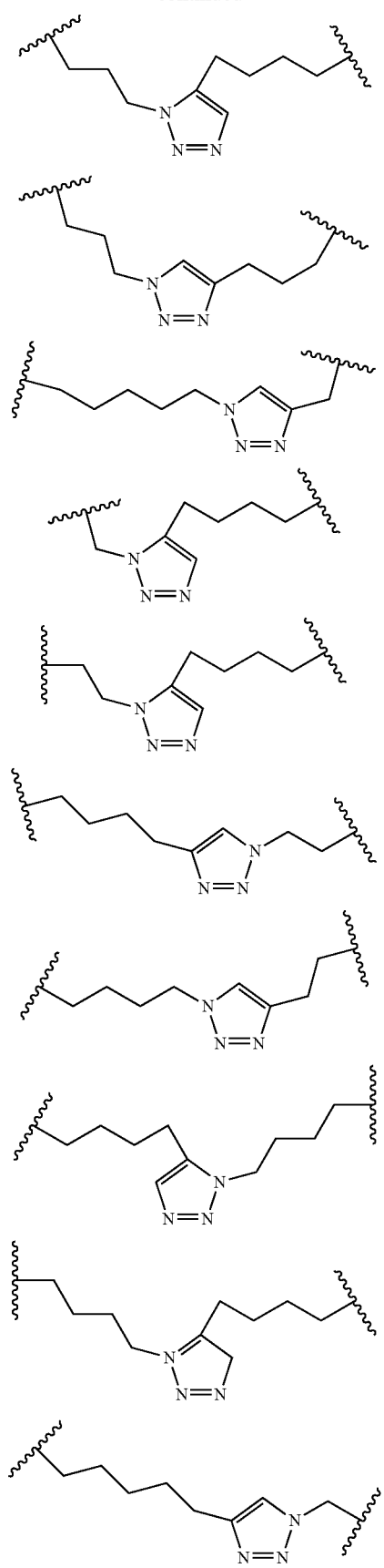
32
-continued
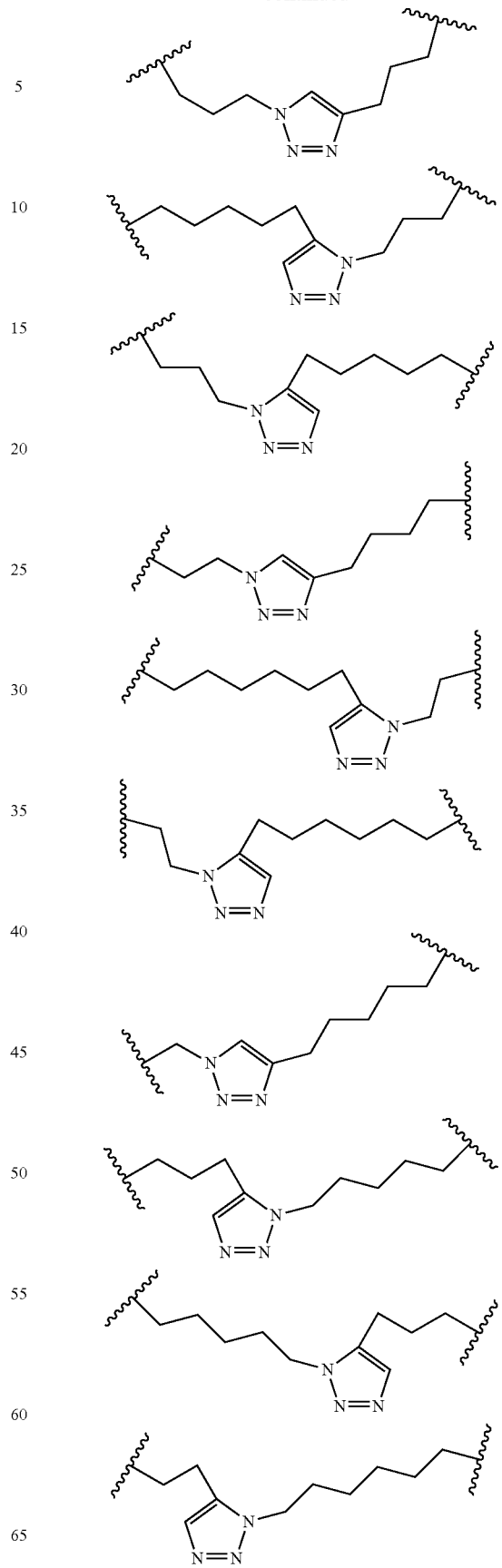

33
-continued
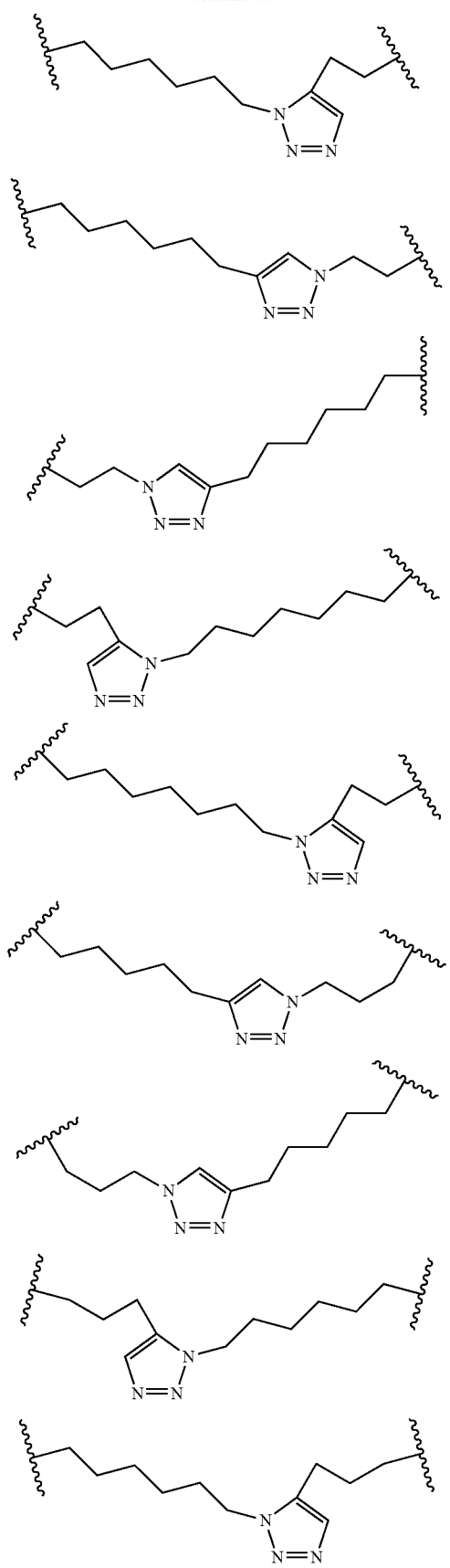
34
-continued
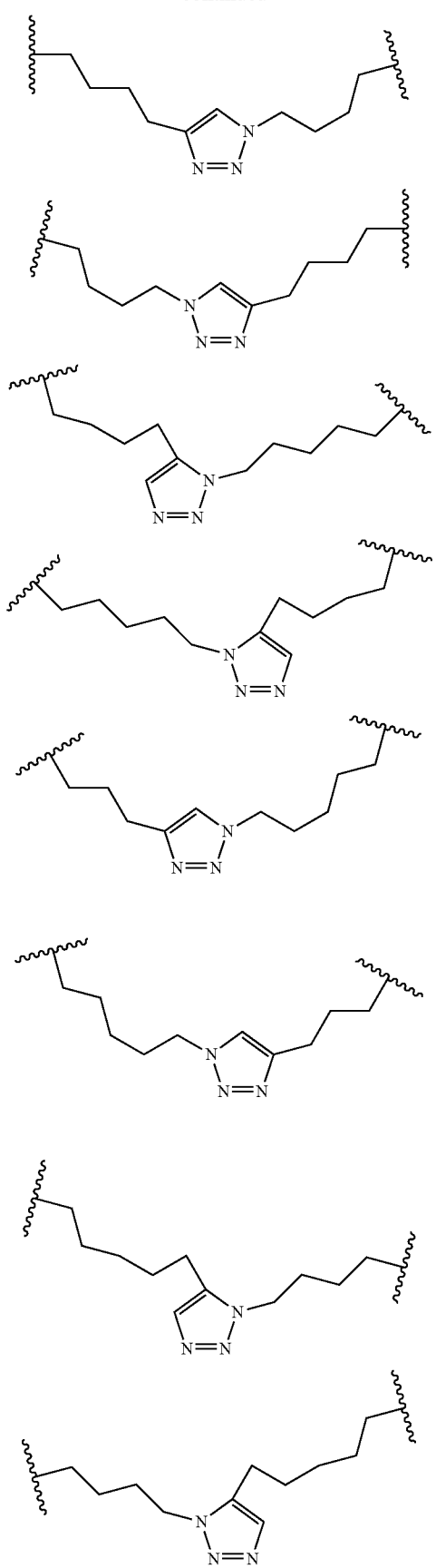

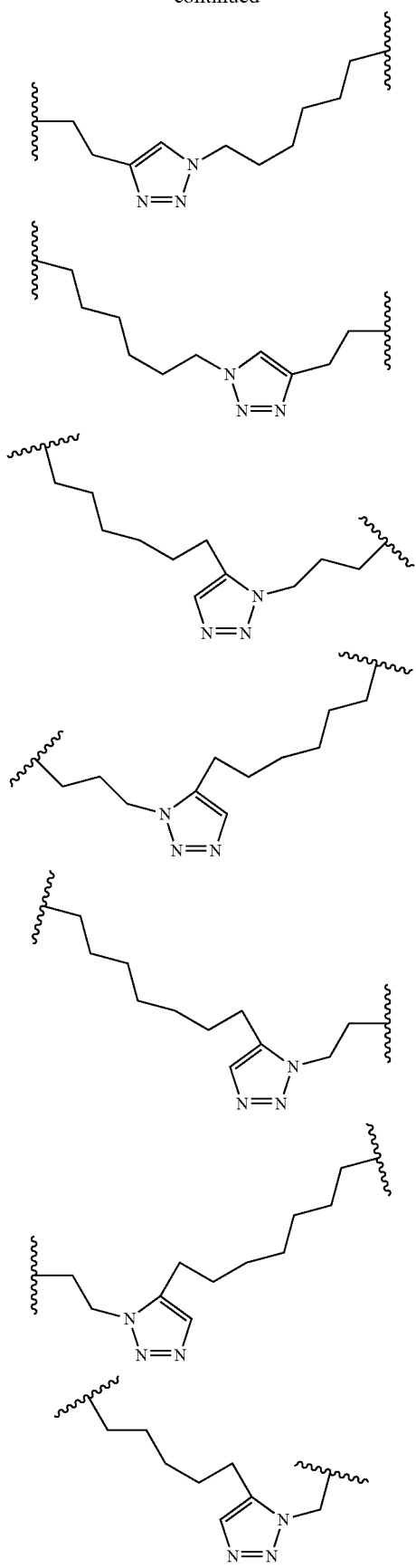
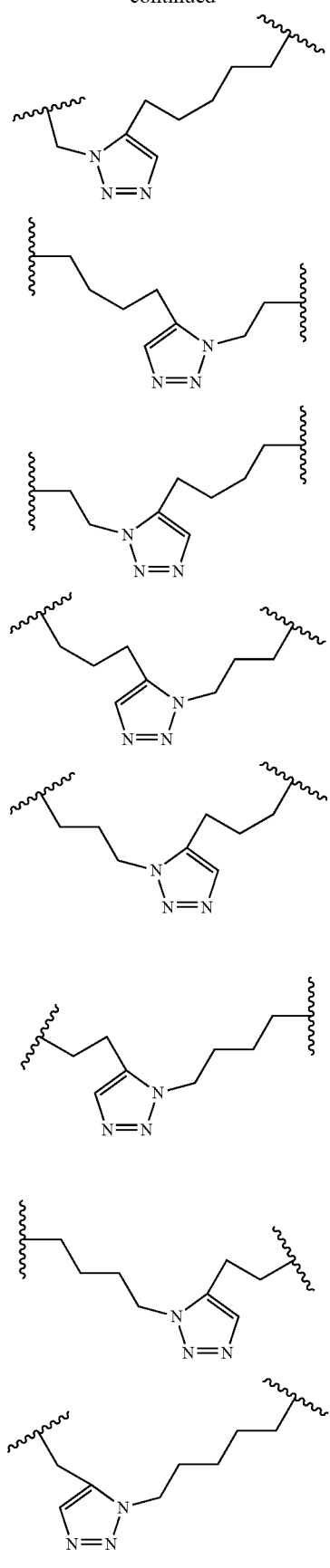

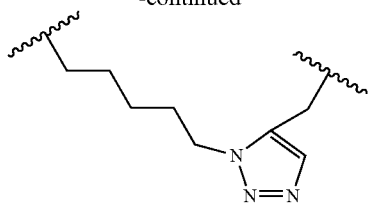

In other embodiments, the invention provides crosslinked polypeptides of Formula (III):

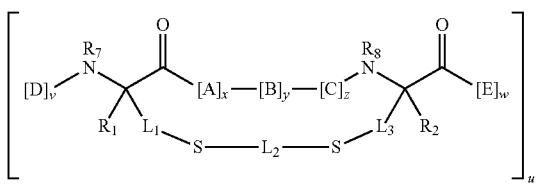

wherein:
each A, C, D, and E is independently a natural or non-natural amino acid;
B is a natural or non-natural amino acid, amino acid analog,

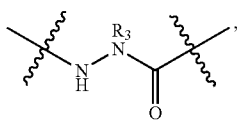

[—NH-$L_4$-CO—], [—NH-$L_4$-$SO_2$—], or [—NH-$L_4$-];
$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;
$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, unsubstituted or substituted with $R_5$;
$L_1$, $L_2$, $L_3$ and $L_4$ are independently alkylene, alkenylene, alkynylene, heteroalkylene, cycloalkylene, heterocycloalkylene, cycloarylene, heterocycloarylene or [—$R_4$—K—$R_4$-]n, each being unsubstituted or substituted with $R_5$;
K is O, S, SO, $SO_2$, CO, $CO_2$, or $CONR_3$;
each $R_4$ is alkylene, alkenylene, alkynylene, heteroalkylene, cycloalkylene, heterocycloalkylene, arylene, or heteroarylene;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;
each $R_6$ is independently —H, alkyl, alkenyl, alkynyl, arylalkyl, cycloalkylalkyl, heterocycloalkyl, a fluorescent moiety, a radioisotope or a therapeutic agent;
$R_7$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with a D residue;
$R_8$ is —H, alkyl, alkenyl, alkynyl, arylalkyl, cycloalkyl, heteroalkyl, cycloalkylalkyl, heterocycloalkyl, cycloaryl, or heterocycloaryl, unsubstituted or substituted with $R_5$, or part of a cyclic structure with an E residue;
u is an integer from 0-10;
v is an integer from 1-1000;
w is an integer from 1-1000;
x is an integer from 0-10;
y is an integer from 0-10;
z is an integer from 0-10; and
n is an integer from 1-5.

In one example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl.

In some embodiments of the invention, x+y+z is at least 3. In other embodiments of the invention, x+y+z is 3, 4, 5, 6, 7, 8, 9 or 10. Each occurrence of A, B, C, D or E in a macrocycle or macrocycle precursor of the invention is independently selected. For example, a sequence represented by the formula $[A]_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the crosslinked polypeptide of the invention comprises a secondary structure which is an α-helix and $R_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

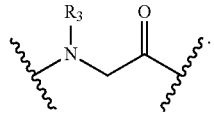

In other embodiments, the length of the macrocycle-forming linker [-$L_1$-S-$L_2$-S-$L_3$-] as measured from a first Cα to a second Cα is selected to stabilize a desired secondary peptide structure, such as an α-helix formed by residues of the crosslinked polypeptide including, but not necessarily limited to, those between the first Cα to a second Cα.

Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in *Chemistry and Biochemistry of the Amino Acids*, edited by G. C. Barrett, Chapman and Hall, 1985. In some embodiments, the thiol moieties are the side chains of the amino acid residues L-cysteine, D-cysteine, α-methyl-L cysteine, α-methyl-D-cysteine, L-homocysteine, D-homocysteine, α-methyl-L-homocysteine or α-methyl-D-homocysteine. A bis-alkylating reagent is of the general formula X-$L_2$-Y wherein $L_2$ is a linker moiety and X and Y are leaving groups that are displaced by —SH moieties to form bonds with $L_2$. In some embodiments, X and Y are halogens such as I, Br, or Cl.

In other embodiments, D and/or E in the compound of Formula I, II or III are further modified in order to facilitate cellular uptake. In some embodiments, lipidating or PEGylating a crosslinked polypeptide facilitates cellular uptake, increases bioavailability, increases blood circulation, alters pharmacokinetics, decreases immunogenicity and/or decreases the needed frequency of administration.

In other embodiments, at least one of [D] and [E] in the compound of Formula I, II or III represents a moiety comprising an additional macrocycle-forming linker such that the crosslinked polypeptide comprises at least two macrocycle-forming linkers. In a specific embodiment, a crosslinked polypeptide comprises two macrocycle-forming linkers.

In the crosslinked polypeptides of the invention, any of the macrocycle-forming linkers described herein may be used in any combination with any of the sequences shown in Tables 1-4 and also with any of the R— substituents indicated herein.

In some embodiments, the crosslinked polypeptide comprises at least one α-helix motif. For example, A, B and/or C in the compound of Formula I, II or III include one or more α-helices. As a general matter, α-helices include between 3 and 4 amino acid residues per turn. In some embodiments, the α-helix of the crosslinked polypeptide includes 1 to 5 turns and, therefore, 3 to 20 amino acid residues. In specific embodiments, the α-helix includes 1 turn, 2 turns, 3 turns, 4 turns, or 5 turns. In some embodiments, the macrocycle-forming linker stabilizes an α-helix motif included within the crosslinked polypeptide. Thus, in some embodiments, the length of the macrocycle-forming linker L from a first Cα to a second Cα is selected to increase the stability of an α-helix. In some embodiments, the macrocycle-forming linker spans from 1 turn to 5 turns of the α-helix. In some embodiments, the macrocycle-forming linker spans approximately 1 turn, 2 turns, 3 turns, 4 turns, or 5 turns of the α-helix. In some embodiments, the length of the macrocycle-forming linker is approximately 5 Å to 9 Å per turn of the α-helix, or approximately 6 Å to 8 Å per turn of the α-helix. Where the macrocycle-forming linker spans approximately 1 turn of an α-helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of an α-helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of an α-helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of an α-helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of an α-helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of an α-helix, the linkage contains approximately 4 atoms to 12 atoms, approximately 6 atoms to 10 atoms, or approximately 8 atoms. Where the macrocycle-forming linker spans approximately 2 turns of the α-helix, the linkage contains approximately 7 atoms to 15 atoms, approximately 9 atoms to 13 atoms, or approximately 11 atoms. Where the macrocycle-forming linker spans approximately 3 turns of the α-helix, the linkage contains approximately 13 atoms to 21 atoms, approximately 15 atoms to 19 atoms, or approximately 17 atoms. Where the macrocycle-forming linker spans approximately 4 turns of the α-helix, the linkage contains approximately 19 atoms to 27 atoms, approximately 21 atoms to 25 atoms, or approximately 23 atoms. Where the macrocycle-forming linker spans approximately 5 turns of the α-helix, the linkage contains approximately 25 atoms to 33 atoms, approximately 27 atoms to 31 atoms, or approximately 29 atoms. Where the macrocycle-forming linker spans approximately 1 turn of the α-helix, the resulting macrocycle forms a ring containing approximately 17 members to 25 members, approximately 19 members to 23 members, or approximately 21 members. Where the macrocycle-forming linker spans approximately 2 turns of the α-helix, the resulting macrocycle forms a ring containing approximately 29 members to 37 members, approximately 31 members to 35 members, or approximately 33 members. Where the macrocycle-forming linker spans approximately 3 turns of the α-helix, the resulting macrocycle forms a ring containing approximately 44 members to 52 members, approximately 46 members to 50 members, or approximately 48 members. Where the macrocycle-forming linker spans approximately 4 turns of the α-helix, the resulting macrocycle forms a ring containing approximately 59 members to 67 members, approximately 61 members to 65 members, or approximately 63 members. Where the macrocycle-forming linker spans approximately 5 turns of the α-helix, the resulting macrocycle forms a ring containing approximately 74 members to 82 members, approximately 76 members to 80 members, or approximately 78 members.

In other embodiments, the invention provides crosslinked polypeptides of Formula (IV) or (IVa):

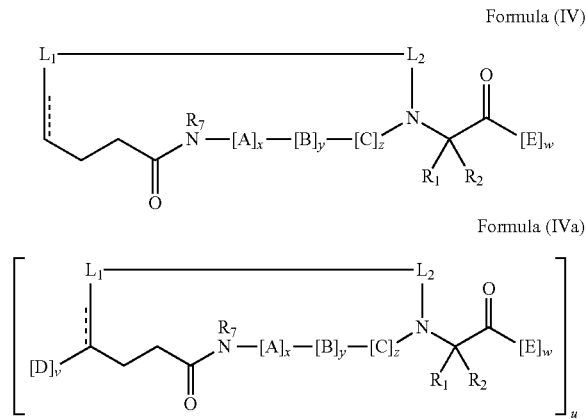

wherein:
each A, C, D, and E is independently a natural or non-natural amino acid;
B is a natural or non-natural amino acid, amino acid analog,

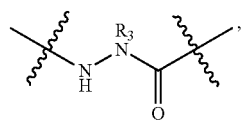

[—NH-$L_3$-CO—], [—NH-$L_3$-$SO_2$—], or [—NH-$L_3$-];
$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;
$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;
L is a macrocycle-forming linker of the formula -$L_1$-$L_2$-;
$L_1$ and $L_2$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

each R$_4$ is alkylene, alkenylene, alkynylene, heteroalkylene, cycloalkylene, heterocycloalkylene, arylene, or heteroarylene;

each K is O, S, SO, SO$_2$, CO, CO$_2$, or CONR$_3$;

each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;

each R$_6$ is independently —H, alkyl, alkenyl, alkynyl, arylalkyl, cycloalkylalkyl, heterocycloalkyl, a fluorescent moiety, a radioisotope or a therapeutic agent;

R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$;

u is an integer from 0-10;

v is an integer from 1-1000;

w is an integer from 1-1000;

x is an integer from 0-10;

y is an integer from 0-10;

z is an integer from 0-10; and n is an integer from 1-5.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments of the invention, x+y+z is at least 1. In some embodiments of the invention, x+y+z is at least 2. In other embodiments of the invention, x+y+z is 3, 4, 5, 6, 7, 8, 9 or 10. Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the crosslinked polypeptide of the invention comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

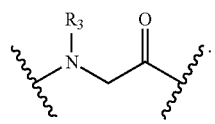

In other embodiments, the length of the macrocycle-forming linker L as measured from a first Cα to a second Cα is selected to stabilize a desired secondary peptide structure, such as an α-helix formed by residues of the crosslinked polypeptide including, but not necessarily limited to, those between the first Cα to a second Cα.

Exemplary embodiments of the macrocycle-forming linker L are shown below.

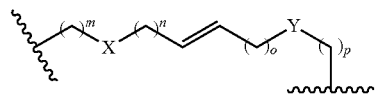

where X, Y = —CH$_2$—, O, S, or NH
m, n, o, p = 0-10

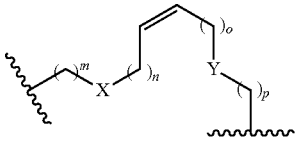

where X, Y = —CH$_2$—, O, S, or NH
m, n, o, p = 0-10

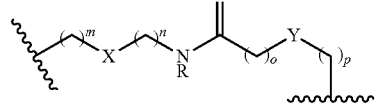

where X, Y = —CH$_2$—, O, S, or NH
m, n, o, p = 0-10
R = H, alkyl, other substituent

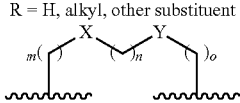

where X, Y = —CH$_2$—, O, S, or NH
m, n, o = 0-10

Preparation of Crosslinked Polypeptides

Crosslinked polypeptides of the invention may be prepared by any of a variety of methods known in the art. For example, any of the residues indicated by "X" in Tables 1, 2, 3 or 4 may be substituted with a residue of forming a crosslinker with a second residue in the same molecule or a precursor of such a residue.

Various methods to effect formation of crosslinked polypeptides are known in the art. For example, the preparation of crosslinked polypeptides of Formula I is described in Schafmeister et al., J. Am. Chem. Soc. 122:5891-5892 (2000); Schafmeister & Verdine, J. Am. Chem. Soc. 122:5891 (2005); Walensky et al., Science 305:1466-1470 (2004); U.S. Pat. No. 7,192,713; and PCT application WO 2008/121767. The α,α-disubstituted amino acids and amino acid precursors disclosed in the cited references may be employed in synthesis of the crosslinked polypeptide precursor polypeptides. Following incorporation of such amino acids into precursor polypeptides, the terminal olefins are reacted with a metathesis catalyst, leading to the formation of the crosslinked polypeptide.

In other embodiments, the peptidomimetic macrocycles of the invention are of Formula IV or IVa. Methods for the preparation of such macrocycles are described, for example, in U.S. Pat. No. 7,202,332.

In some embodiments, the synthesis of these crosslinked polypeptides involves a multi-step process that features the synthesis of a peptidomimetic precursor containing an azide moiety and an alkyne moiety; followed by contacting the peptidomimetic precursor with a macrocyclization reagent to generate a triazole-linked crosslinked polypeptide. Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in *Chemistry and Biochemistry of the Amino Acids*, edited by G. C. Barrett, Chapman and Hall, 1985.

In some embodiments, an azide is linked to the α-carbon of a residue and an alkyne is attached to the α-carbon of another residue. In some embodiments, the azide moieties are azido-analogs of amino acids L-lysine, D-lysine, alpha-methyl-L-lysine, alpha-methyl-D-lysine, L-ornithine, D-ornithine, alpha-methyl-L-ornithine or alpha-methyl-D-ornithine. In another embodiment, the alkyne moiety is L-propargylglycine. In yet other embodiments, the alkyne moiety is an amino acid selected from the group consisting of L-propargylglycine, D-propargylglycine, (S)-2-amino-2-methyl-4-pentynoic acid, (R)-2-amino-2-methyl-4-pentynoic acid, (S)-2-amino-2-methyl-5-hexynoic acid, (R)-2-amino-2-methyl-5-hexynoic acid, (S)-2-amino-2-methyl-6-heptynoic acid, (R)-2-amino-2-methyl-6-heptynoic acid, (S)-2-amino-2-methyl-7-octynoic acid, (R)-2-amino-2-methyl-7-octynoic acid, (S)-2-amino-2-methyl-8-nonynoic acid and (R)-2-amino-2-methyl-8-nonynoic acid.

In some embodiments, the invention provides a method for synthesizing a crosslinked polypeptide, the method comprising the steps of contacting a peptidomimetic precursor of Formula V or Formula VI:

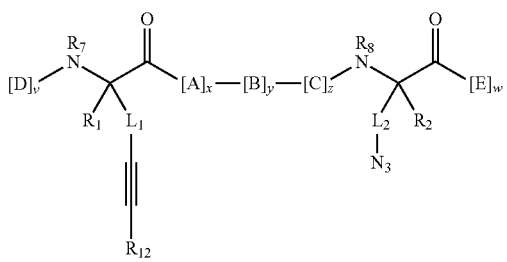

Formula (V)

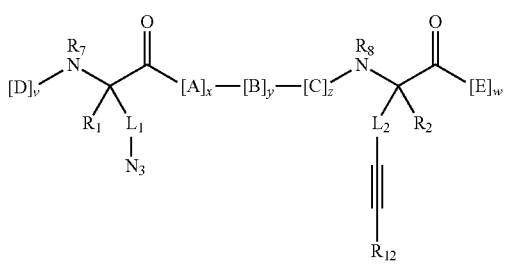

Formula (VI)

with a macrocyclization reagent;
wherein v, w, x, y, z, A, B, C, D, E, $R_1$, $R_2$, $R_7$, $R_8$, $L_1$ and $L_2$ are as defined for Formula (II); $R_{12}$ is —H when the macrocyclization reagent is a Cu reagent and $R_{12}$ is —H or alkyl when the macrocyclization reagent is a Ru reagent; and further wherein said contacting step results in a covalent linkage being formed between the alkyne and azide moiety in Formula III or Formula IV. For example, $R_{12}$ may be methyl when the macrocyclization reagent is a Ru reagent.

In the crosslinked polypeptides of the invention, at least one of $R_1$ and $R_2$ is alkyl, alkenyl, alkynyl, arylalkyl, cycloalkyl, cycloalkylalkyl, heteroalkyl, or heterocycloalkyl, unsubstituted or substituted with halo-. In some embodiments, both $R_1$ and $R_2$ are independently alkyl, alkenyl, alkynyl, arylalkyl, cycloalkyl, cycloalkylalkyl, heteroalkyl, or heterocycloalkyl, unsubstituted or substituted with halo-. In some embodiments, at least one of A, B, C, D or E is an α,α-disubstituted amino acid. In one example, B is an α,α-disubstituted amino acid. For instance, at least one of A, B, C, D or E is 2-aminoisobutyric acid.

For example, at least one of $R_1$ and $R_2$ is alkyl, unsubstituted or substituted with halo-. In another example, both $R_1$ and $R_2$ are independently alkyl, unsubstituted or substituted with halo-. In some embodiments, at least one of $R_1$ and $R_2$ is methyl. In other embodiments, $R_1$ and $R_2$ are methyl. The macrocyclization reagent may be a Cu reagent or a Ru reagent.

In some embodiments, the peptidomimetic precursor is purified prior to the contacting step. In other embodiments, the crosslinked polypeptide is purified after the contacting step. In still other embodiments, the crosslinked polypeptide is refolded after the contacting step. The method may be performed in solution, or, alternatively, the method may be performed on a solid support.

Also envisioned herein is performing the method of the invention in the presence of a target macromolecule that binds to the peptidomimetic precursor or crosslinked polypeptide under conditions that favor said binding. In some embodiments, the method is performed in the presence of a target macromolecule that binds preferentially to the peptidomimetic precursor or crosslinked polypeptide under conditions that favor said binding. The method may also be applied to synthesize a library of crosslinked polypeptides.

In some embodiments, the alkyne moiety of the peptidomimetic precursor of Formula V or Formula VI is a sidechain of an amino acid selected from the group consisting of L-propargylglycine, D-propargylglycine, (S)-2-amino-2-methyl-4-pentynoic acid, (R)-2-amino-2-methyl-4-pentynoic acid, (S)-2-amino-2-methyl-5-hexynoic acid, (R)-2-amino-2-methyl-5-hexynoic acid, (S)-2-amino-2-methyl-6-heptynoic acid, (R)-2-amino-2-methyl-6-heptynoic acid, (S)-2-amino-2-methyl-7-octynoic acid, (R)-2-amino-2-methyl-7-octynoic acid, (S)-2-amino-2-methyl-8-nonynoic acid, and (R)-2-amino-2-methyl-8-nonynoic acid. In other embodiments, the azide moiety of the peptidomimetic precursor of Formula V or Formula VI is a sidechain of an amino acid selected from the group consisting of e-azido-L-lysine, e-azido-D-lysine, e-azido-α-methyl-L-lysine, e-azido-α-methyl-D-lysine, d-azido-α-methyl-L-ornithine, and d-azido-α-methyl-D-ornithine.

In some embodiments, x+y+z is 3, and and A, B and C are independently natural or non-natural amino acids. In other embodiments, x+y+z is 6, and and A, B and C are independently natural or non-natural amino acids.

In some embodiments of peptidomimetic macrocycles of the invention, $[D]_v$ and/or $[E]_w$ comprise additional peptidomimetic macrocycles or macrocyclic structures. For example, $[D]_v$ may have the formula:

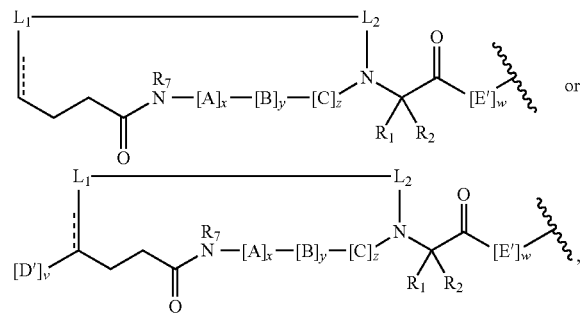

wherein each A, C, D', and E' is independently a natural or non-natural amino acid;

B is a natural or non-natural amino acid, amino acid analog,

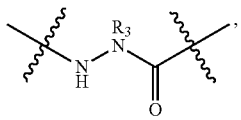

[—NH-L$_3$-CO—], [—NH-L$_3$-SO$_2$—], or [—NH-L$_3$-];

R$_1$ and R$_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;

R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with R$_5$;

L$_1$ and L$_2$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

each R$_4$ is alkylene, alkenylene, alkynylene, heteroalkylene, cycloalkylene, heterocycloalkylene, arylene, or heteroarylene;

each K is O, S, SO, SO$_2$, CO, CO$_2$, or CONR$_3$;

each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;

each R$_6$ is independently —H, alkyl, alkenyl, alkynyl, arylalkyl, cycloalkylalkyl, heterocycloalkyl, a fluorescent moiety, a radioisotope or a therapeutic agent;

R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$;

v is an integer from 1-1000;

w is an integer from 1-1000; and x is an integer from 0-10.

In another embodiment, [E]$_w$ has the formula:

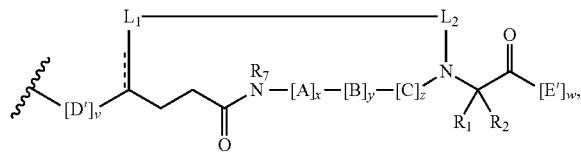

wherein the substituents are as defined in the preceding paragraph.

In some embodiments, the contacting step is performed in a solvent selected from the group consisting of protic solvent, aqueous solvent, organic solvent, and mixtures thereof. For example, the solvent may be chosen from the group consisting of H$_2$O, THF, THF/H$_2$O, tBuOH/H$_2$O, DMF, DIPEA, CH$_3$CN or CH$_2$Cl$_2$, ClCH$_2$CH$_2$Cl or a mixture thereof. The solvent may be a solvent which favors helix formation.

Alternative but equivalent protecting groups, leaving groups or reagents are substituted, and certain of the synthetic steps are performed in alternative sequences or orders to produce the desired compounds. Synthetic chemistry transformations and protecting group methodologies (protection and deprotection) useful in synthesizing the compounds described herein include, for example, those such as described in Larock, *Comprehensive Organic Transformations*, VCH Publishers (1989); Greene and Wuts, *Protective Groups in Organic Synthesis,* 2d. Ed., John Wiley and Sons (1991); Fieser and Fieser, *Fieser and Fieser's Reagents for Organic Synthesis*, John Wiley and Sons (1994); and Paquette, ed., *Encyclopedia of Reagents for Organic Synthesis*, John Wiley and Sons (1995), and subsequent editions thereof.

The crosslinked polypeptides of the invention are made, for example, by chemical synthesis methods, such as described in Fields et al., Chapter 3 in *Synthetic Peptides: A User's Guide*, ed. Grant, W. H. Freeman & Co., New York, N.Y., 1992, p. 77. Hence, for example, peptides are synthesized using the automated Merrifield techniques of solid phase synthesis with the amine protected by either tBoc or Fmoc chemistry using side chain protected amino acids on, for example, an automated peptide synthesizer (e.g., Applied Biosystems (Foster City, Calif.), Model 430A, 431, or 433).

One manner of producing the peptidomimetic precursors and crosslinked polypeptides described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups.

Longer peptidomimetic precursors are produced, for example, by conjoining individual synthetic peptides using native chemical ligation. Alternatively, the longer synthetic peptides are biosynthesized by well known recombinant DNA and protein expression techniques. Such techniques are provided in well-known standard manuals with detailed protocols. To construct a gene encoding a peptidomimetic precursor of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptidomimetic precursors are made, for example, in a high-throughput, combinatorial fashion using, for example, a high-throughput polychannel combinatorial synthesizer (e.g., Thuramed TETRAS multichannel peptide synthesizer from CreoSalus, Louisville, Ky. or Model Apex 396 multichannel peptide synthesizer from AAPPTEC, Inc., Louisville, Ky.).

The following synthetic schemes are provided solely to illustrate the present invention and are not intended to limit the scope of the invention, as described herein. To simplify the drawings, the illustrative schemes depict azido amino acid analogs e-azido-α-methyl-L-lysine and e-azido-α-methyl-D-lysine, and alkyne amino acid analogs L-propargylglycine, (S)-2-amino-2-methyl-4-pentynoic acid, and (S)-2-amino-2-methyl-6-heptynoic acid. Thus, in the following synthetic schemes, each R$_1$, R$_2$, R$_7$ and R$_8$ is —H; each L$_1$ is —(CH$_2$)$_4$—; and each L$_2$ is —(CH$_2$)—. However, as noted throughout the detailed description above, many other amino acid analogs can be employed in which $R_1$, $R_2$, $R_7$, $R_8$, $L_1$ and $L_2$ can be independently selected from the various structures disclosed herein.
Synthetic Scheme 1:
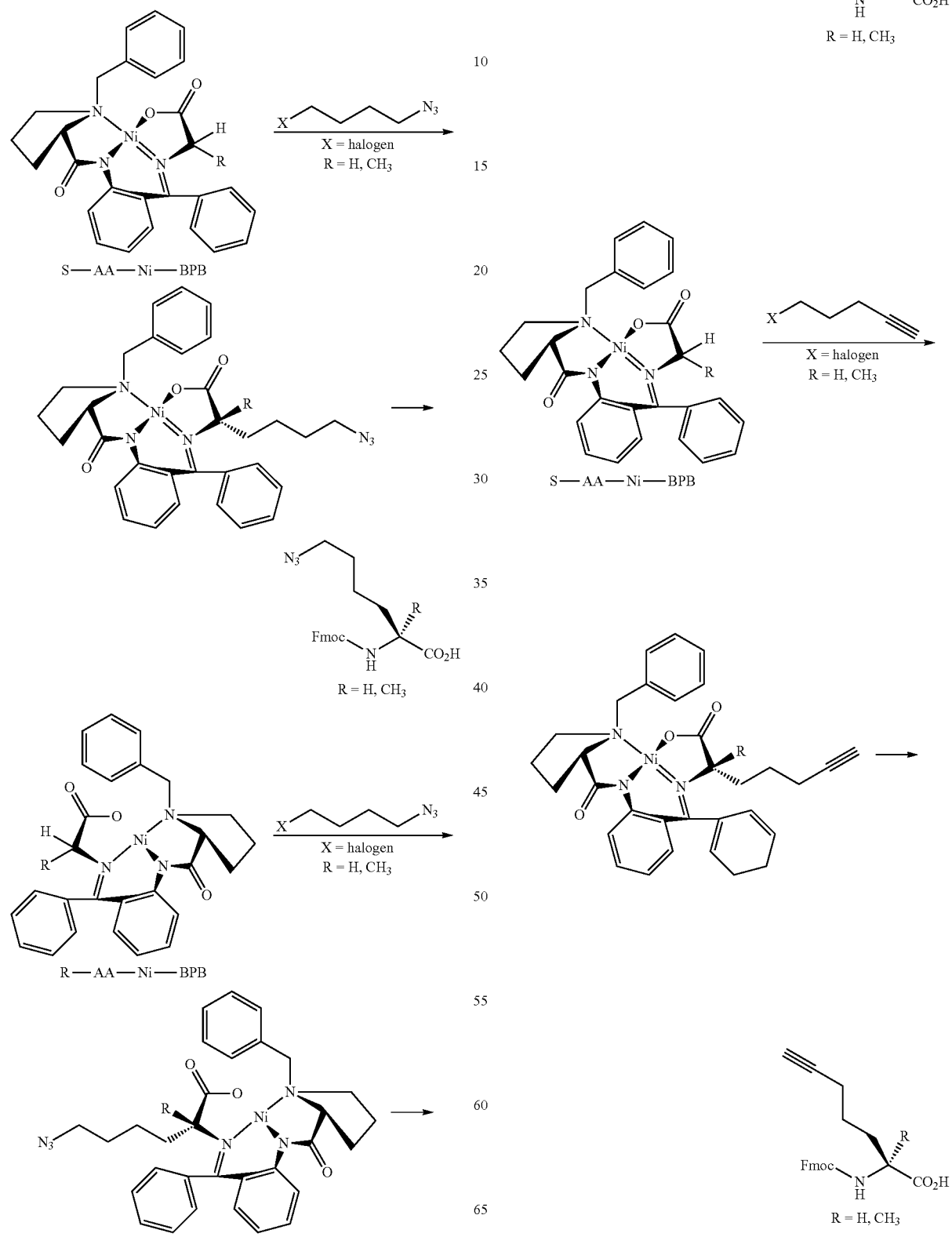

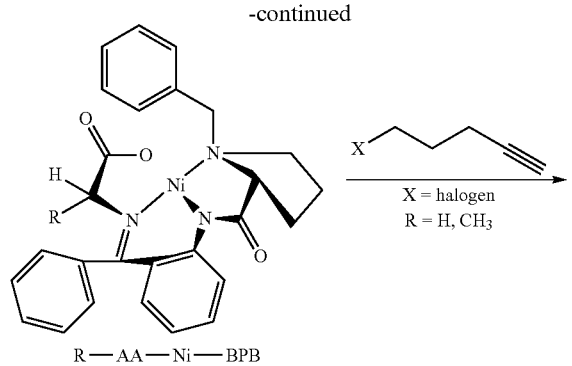

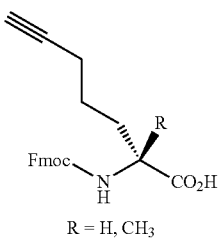

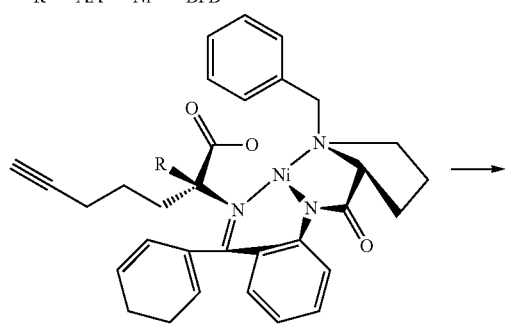

Synthetic Scheme 1 describes the preparation of several compounds of the invention. Ni(II) complexes of Schiff bases derived from the chiral auxiliary (S)-2-[N-(N'-benzylprolyl)amino]benzophenone (BPB) and amino acids such as glycine or alanine are prepared as described in Belokon et al. (1998), *Tetrahedron Asymm.* 9:4249-4252. The resulting complexes are subsequently reacted with alkylating reagents comprising an azido or alkynyl moiety to yield enantiomerically enriched compounds of the invention. If desired, the resulting compounds can be protected for use in peptide synthesis.

Synthetic Scheme 2:

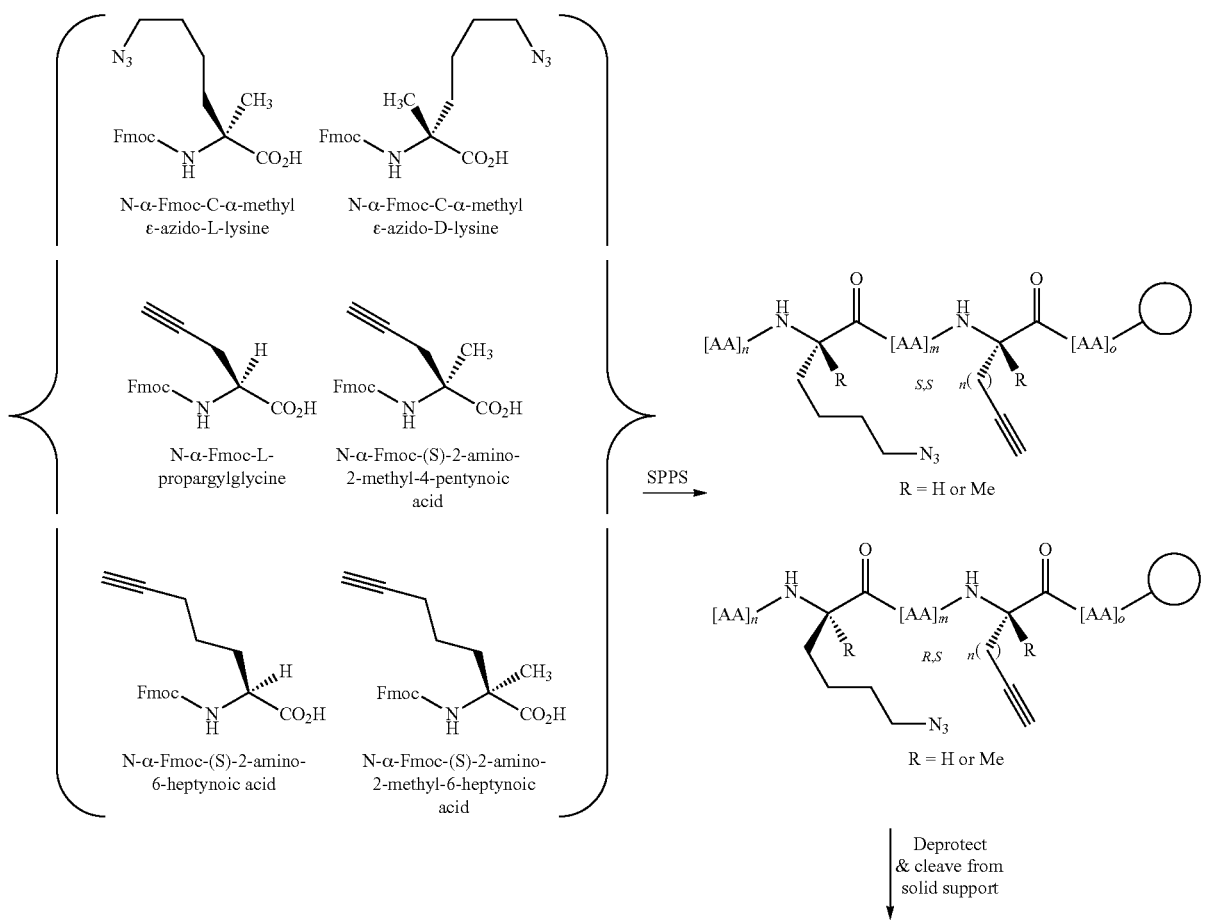

51                                                                52

-continued

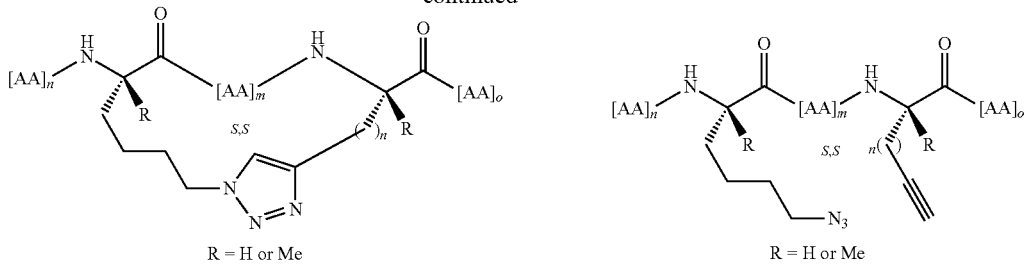

R = H or Me                                                       R = H or Me

Cu (I)

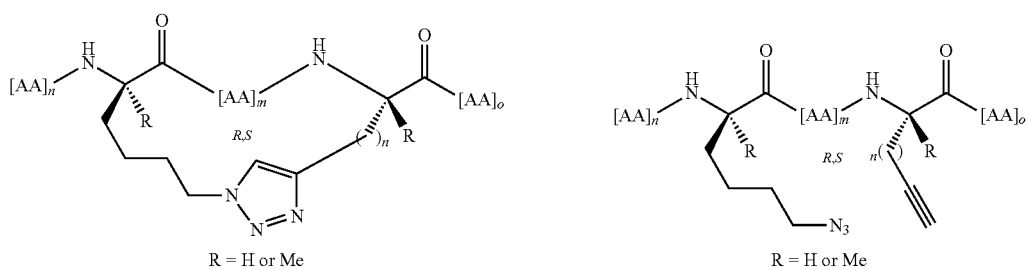

R = H or Me                                                       R = H or Me

In the general method for the synthesis of crosslinked polypeptides shown in Synthetic Scheme 2, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-e-azido-L-lysine, and N-methyl-e-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization reagent such as a Cu(I) in organic or aqueous solutions (Rostovtsev et al. (2002), Angew. Chem. Int. Ed. 41:2596-2599; Tornoe et al. (2002), J. Org. Chem. 67:3057-3064; Deiters et al. (2003), J. Am. Chem. Soc. 125:11782-11783; Punna et al. (2005), Angew. Chem. Int. Ed. 44:2215-2220). In one embodiment, the triazole forming reaction is performed under conditions that favor α-helix formation. In one embodiment, the macrocyclization step is performed in a solvent chosen from the group consisting of H$_2$O, THF, CH$_3$CN, DMF, DIPEA, tBuOH or a mixture thereof. In another embodiment, the macrocyclization step is performed in DMF. In some embodiments, the macrocyclization step is performed in a buffered aqueous or partially aqueous solvent.

Synthetic Scheme 3:

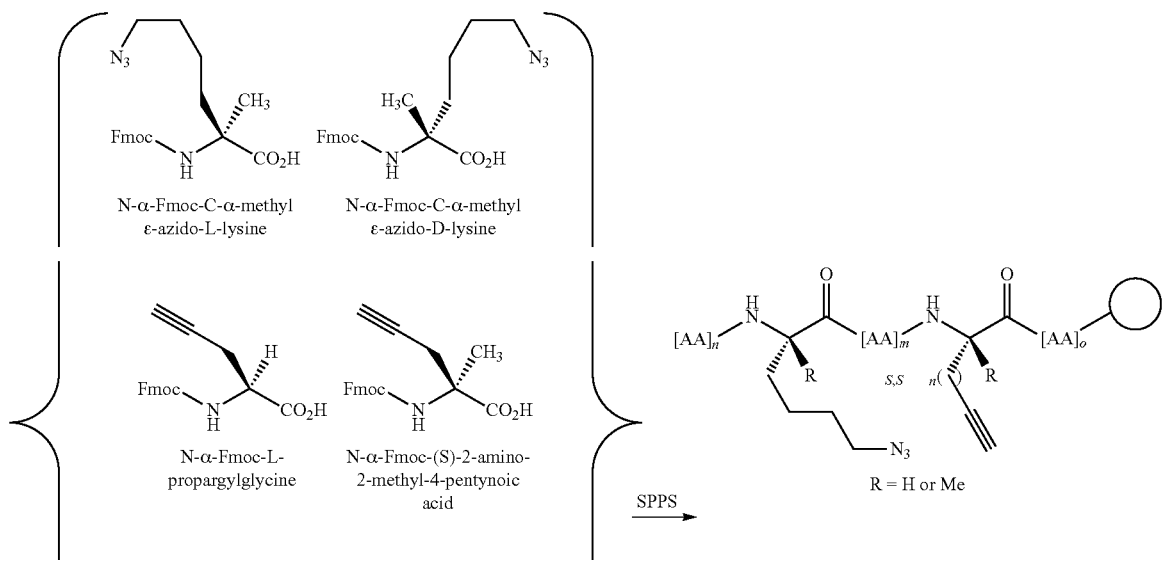

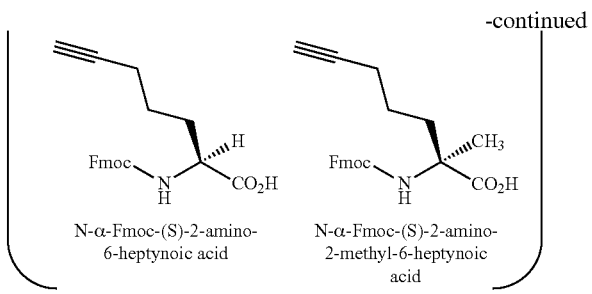

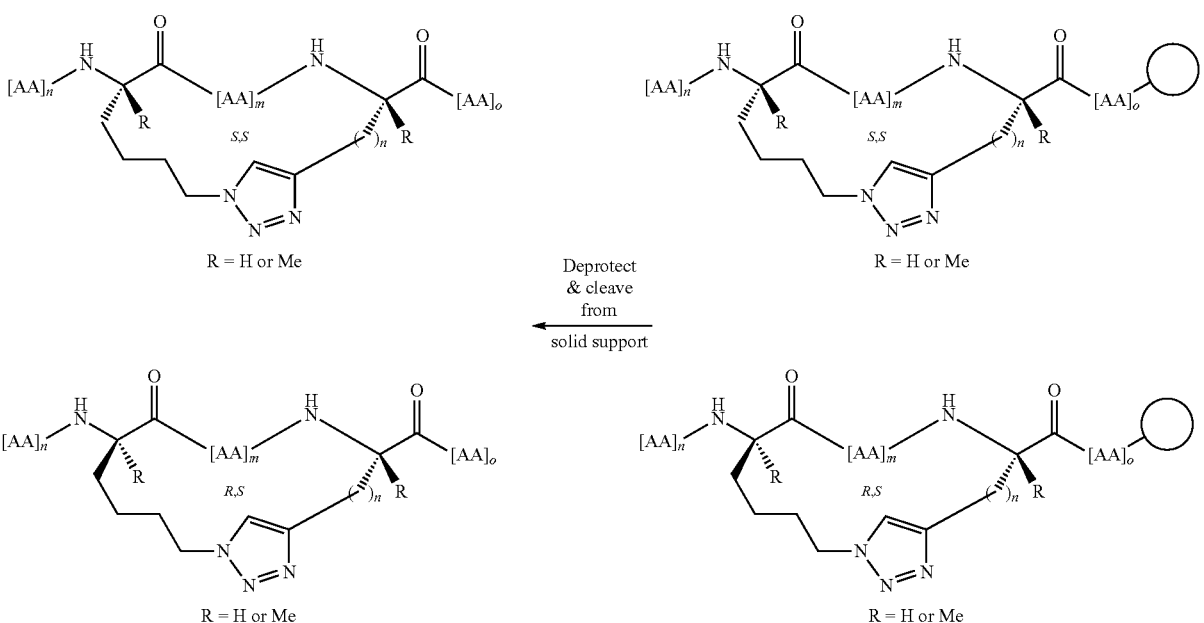

In the general method for the synthesis of crosslinked polypeptides shown in Synthetic Scheme 3, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization reagent such as a Cu(I) reagent on the resin as a crude mixture (Rostovtsev et al. (2002), Angew. Chem. Int. Ed. 41:2596-2599; Tornoe et al. (2002), J. Org. Chem. 67:3057-3064; Deiters et al. (2003), J. Am. Chem. Soc. 125:11782-11783; Punna et al. (2005), Angew. Chem. Int. Ed. 44:2215-2220). The resultant triazole-containing crosslinked polypeptide is then deprotected and cleaved from the solid-phase resin by standard conditions (e.g., strong acid such as 95% TFA). In some embodiments, the macrocyclization step is performed in a solvent chosen from the group consisting of $CH_2Cl_2$, $ClCH_2CH_2Cl$, DMF, THF, NMP, DIPEA, 2,6-lutidine, pyridine, DMSO, $H_2O$ or a mixture thereof. In some embodiments, the macrocyclization step is performed in a buffered aqueous or partially aqueous solvent.

Synthetic Scheme 4:
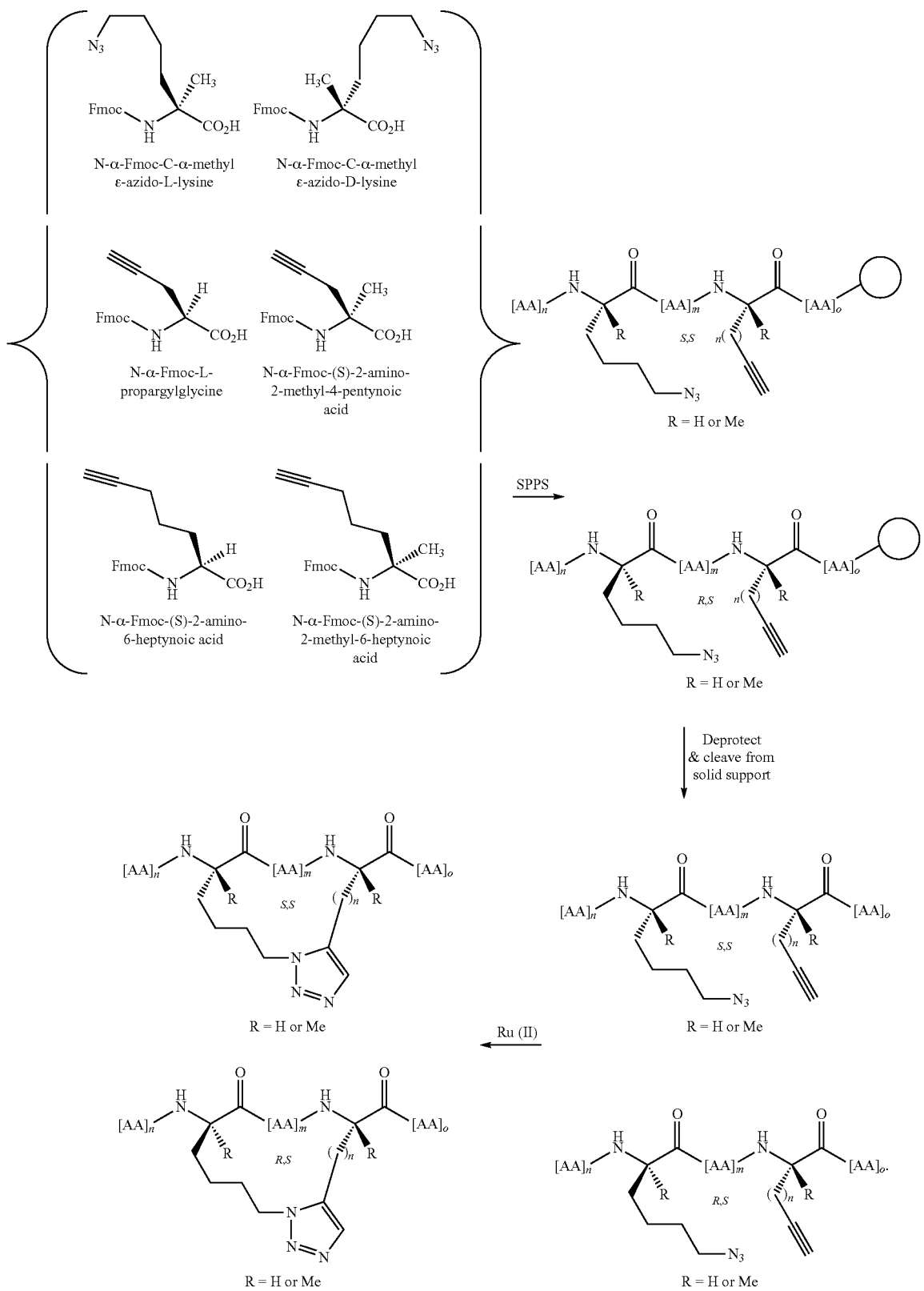

In the general method for the synthesis of crosslinked polypeptides shown in Synthetic Scheme 4, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-e-azido-L-lysine, and N-methyl-e-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization reagent such as a Ru(II) reagents, for example Cp*RuCl(PPh$_3$)$_2$ or [Cp*RuCl]$_4$ (Rasmussen et al. (2007), *Org. Lett.* 9:5337-5339; Zhang et al. (2005), *J. Am. Chem. Soc.* 127:15998-15999). In some embodiments, the macrocyclization step is performed in a solvent chosen from the group consisting of DMF, CH$_3$CN and THF.

Synthetic Scheme 5:

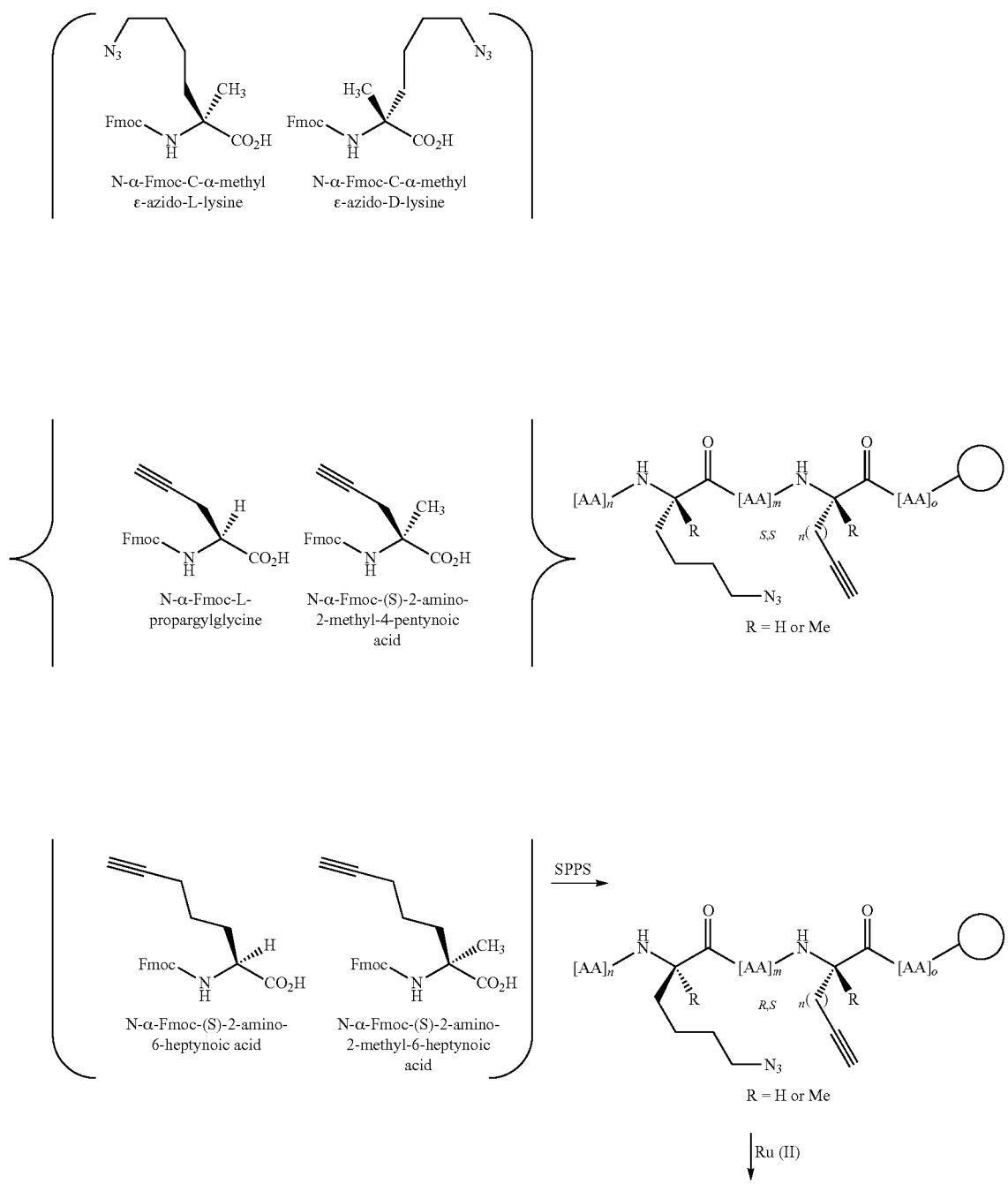

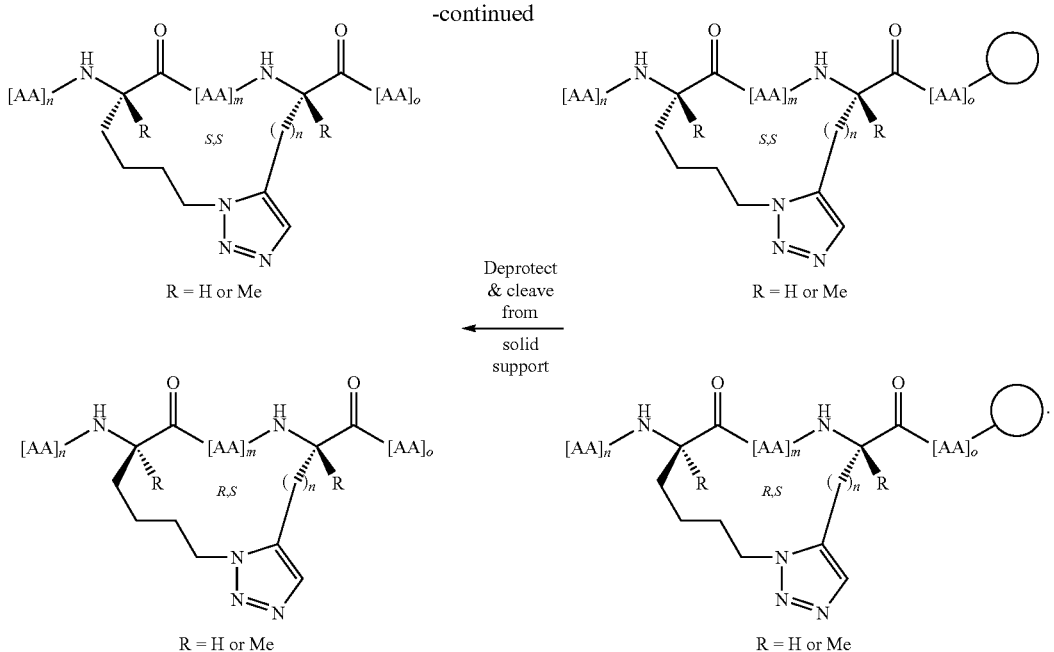

In the general method for the synthesis of crosslinked polypeptides shown in Synthetic Scheme 5, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization reagent such as a Ru(II) reagent on the resin as a crude mixture. For example, the reagent can be Cp*RuCl(PPh$_3$)$_2$ or [Cp*RuCl]$_4$ (Rasmussen et al. (2007), Org. Lett. 9:5337-5339; Zhang et al. (2005), J. Am. Chem. Soc. 127:15998-15999). In some embodiments, the macrocyclization step is performed in a solvent chosen from the group consisting of CH$_2$Cl$_2$, ClCH$_2$CH$_2$Cl, CH$_3$CN, DMF, and THF.

Several exemplary crosslinked polypeptides are shown in Table 5 (SEQ ID NOS 89-100, respectively, in order of appearance). "Nle" represents norleucine and replaces a methionine residue. It is envisioned that similar linkers are used to synthesize crosslinked polypeptides based on the polypeptide sequences disclosed in Table 1 through Table 4.

TABLE 5

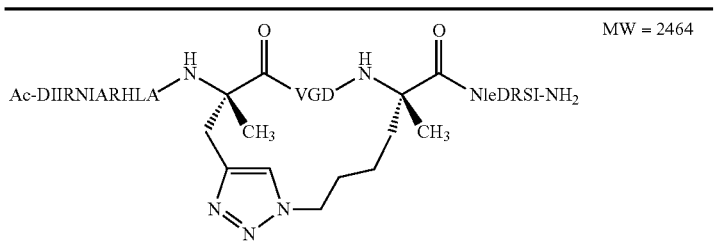

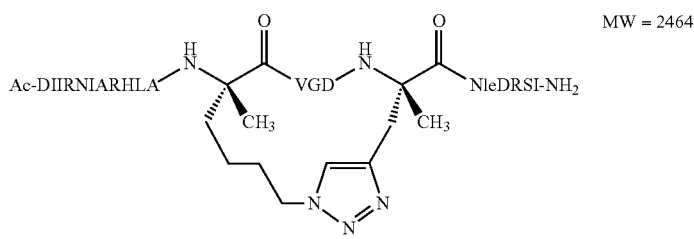

TABLE 5-continued
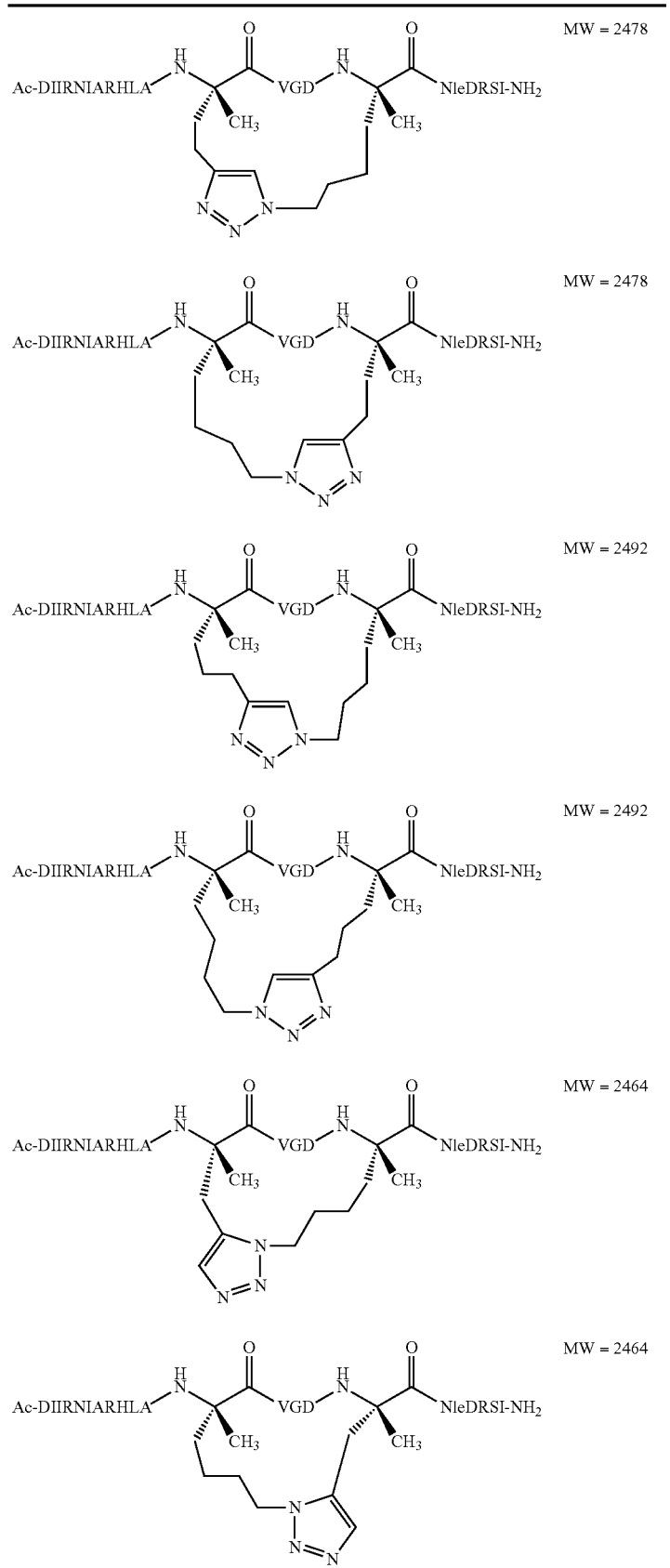

TABLE 5-continued

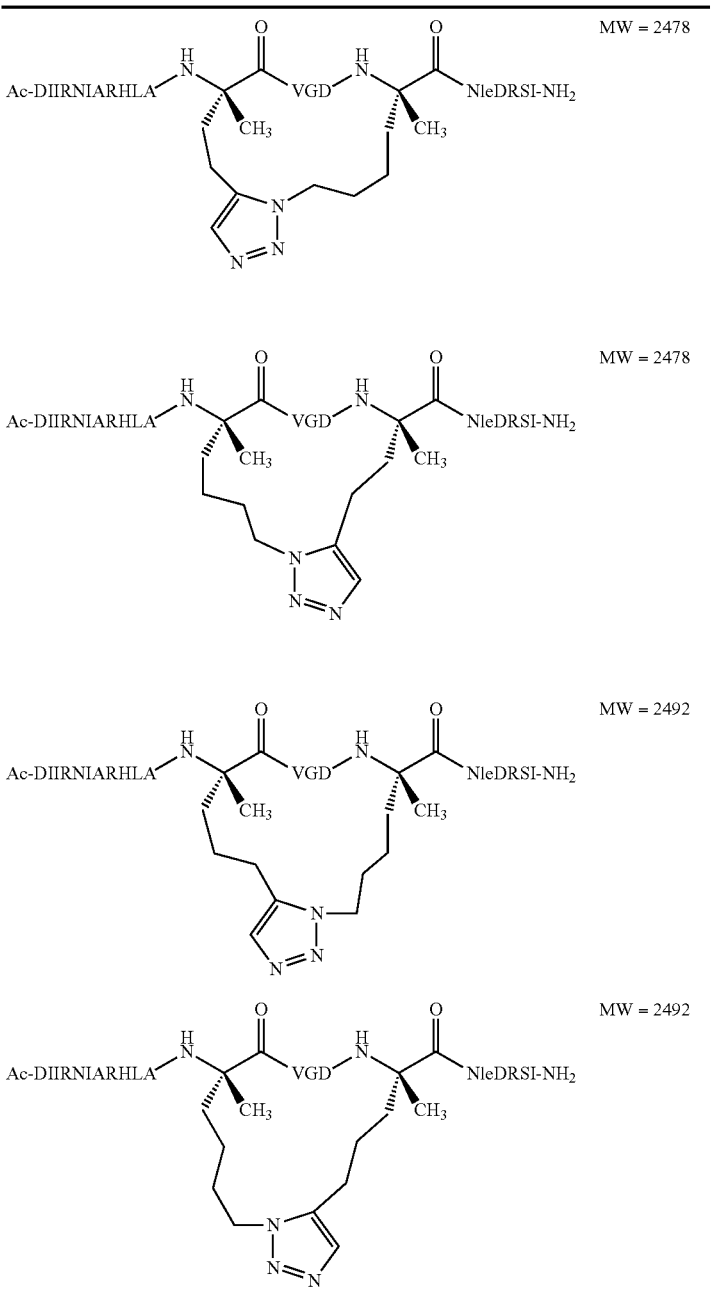

Table 5 shows exemplary peptidommimetic macrocycles of the invention. "Nle" represents norleucine.

The present invention contemplates the use of non-naturally-occurring amino acids and amino acid analogs in the synthesis of the crosslinked polypeptides described herein. Any amino acid or amino acid analog amenable to the synthetic methods employed for the synthesis of stable triazole containing crosslinked polypeptides can be used in the present invention. For example, L-propargylglycine is contemplated as a useful amino acid in the present invention. However, other alkyne-containing amino acids that contain a different amino acid side chain are also useful in the invention. For example, L-propargylglycine contains one methylene unit between the α-carbon of the amino acid and the alkyne of the amino acid side chain. The invention also contemplates the use of amino acids with multiple methylene units between the α-carbon and the alkyne. Also, the azido-analogs of amino acids L-lysine, D-lysine, alpha-methyl-L-lysine, and alpha-methyl-D-lysine are contemplated as useful amino acids in the present invention. However, other terminal azide amino acids that contain a different amino acid side chain are also useful in the invention. For example, the azido-analog of L-lysine contains four methylene units between the α-carbon of the amino acid and the terminal azide of the amino acid side chain. The invention also contemplates the use of amino acids with fewer than or greater than four methylene units between the α-carbon and the terminal azide. Table 6 shows some amino acids useful in the preparation of crosslinked polypeptides of the invention.

TABLE 6

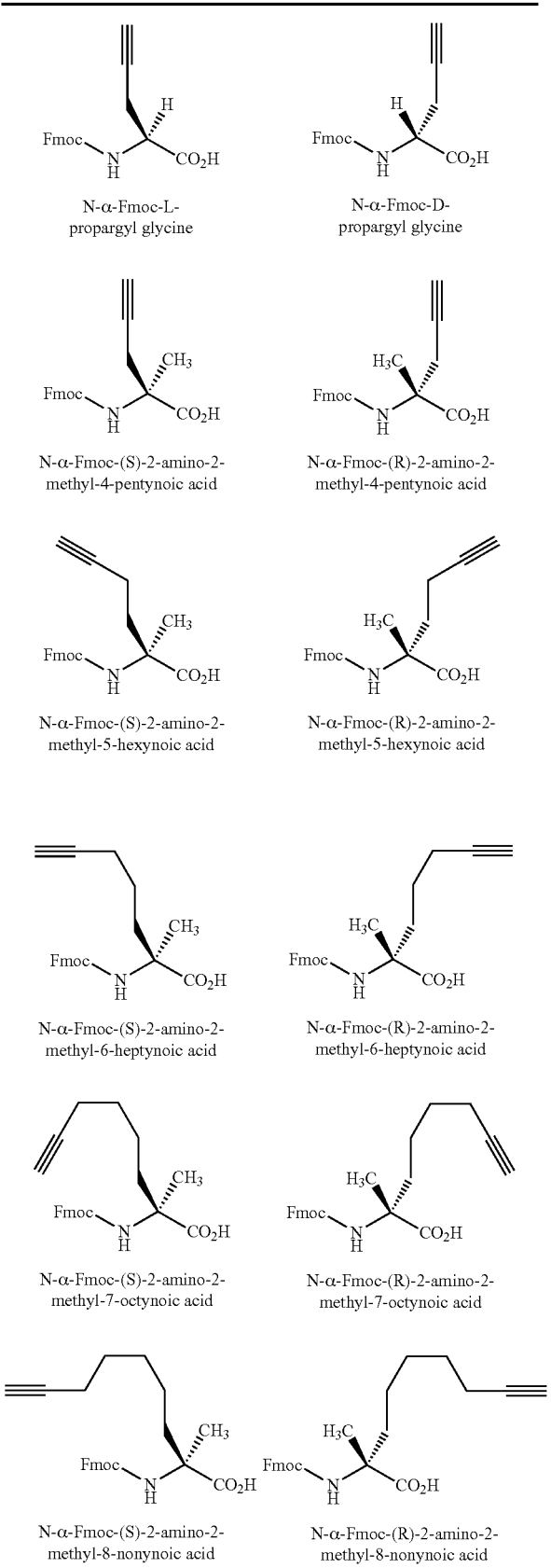

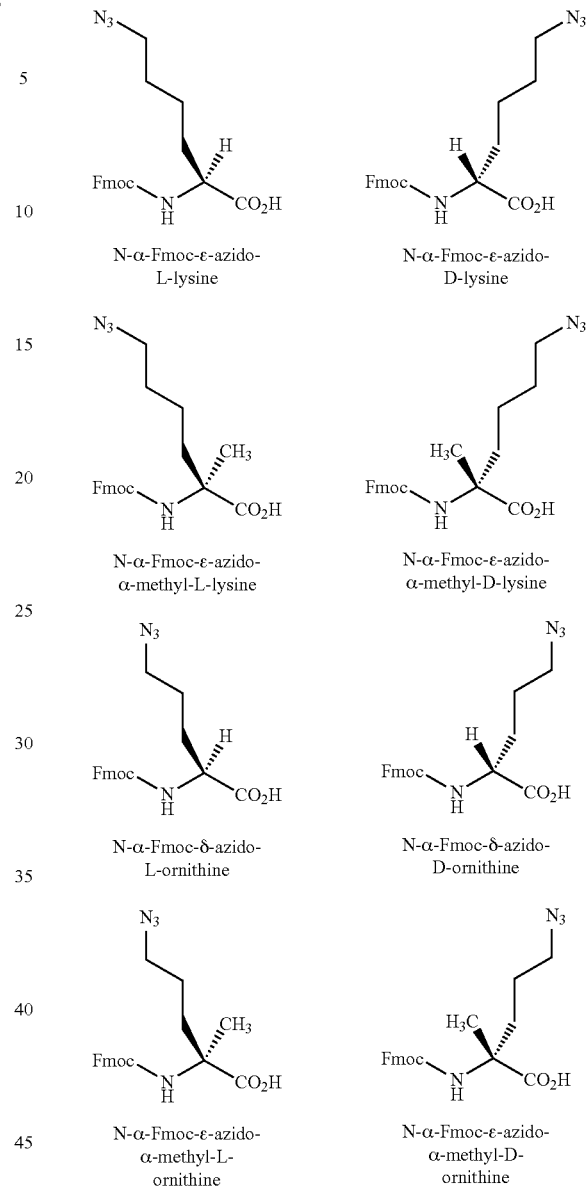

Table 6 shows exemplary amino acids useful in the preparation of crosslinked polypeptides of the invention.

In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-propargylglycine, α-methyl-D-propargylglycine, e-azido-alpha-methyl-L-lysine, and e-azido-alpha-methyl-D-lysine. In some embodiments the amino acid analogs are N-alkylated, e.g., N-methyl-L-propargylglycine, N-methyl-D-propargylglycine, N-methyl-e-azido-L-lysine, and N-methyl-e-azido-D-lysine.

In some embodiments, the —NH moiety of the amino acid is protected using a protecting group, including without limitation-Fmoc and -Boc. In other embodiments, the amino acid is not protected prior to synthesis of the crosslinked polypeptide.

In other embodiments, crosslinked polypeptides of Formula III are synthesized. The following synthetic schemes describe the preparation of such compounds. To simplify the drawings, the illustrative schemes depict amino acid analogs derived from L-or D-cysteine, in which $L_1$ and $L_3$ are both —$(CH_2)$—. However, as noted throughout the detailed description above, many other amino acid analogs can be employed in which $L_1$ and $L_3$ can be independently selected from the various structures disclosed herein. The symbols "$[AA]_m$", "$[AA]_n$", "$[AA]_o$" represent a sequence of amide bond-linked moieties such as natural or unnatural amino acids. As described previously, each occurrence of "AA" is independent of any other occurrence of "AA", and a formula such as "$[AA]_m$" encompasses, for example, sequences of non-identical amino acids as well as sequences of identical amino acids.

Synthetic Scheme 6:

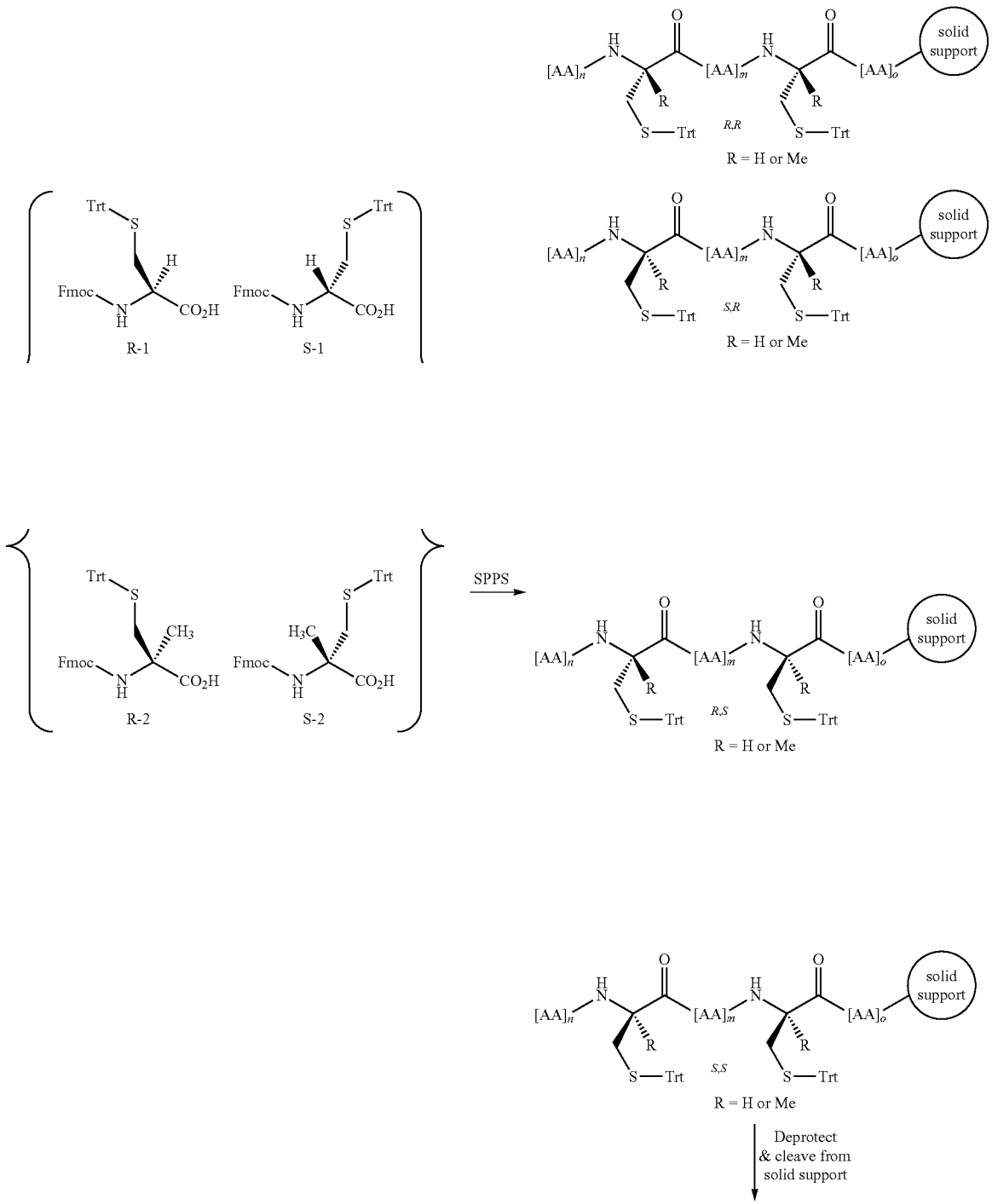

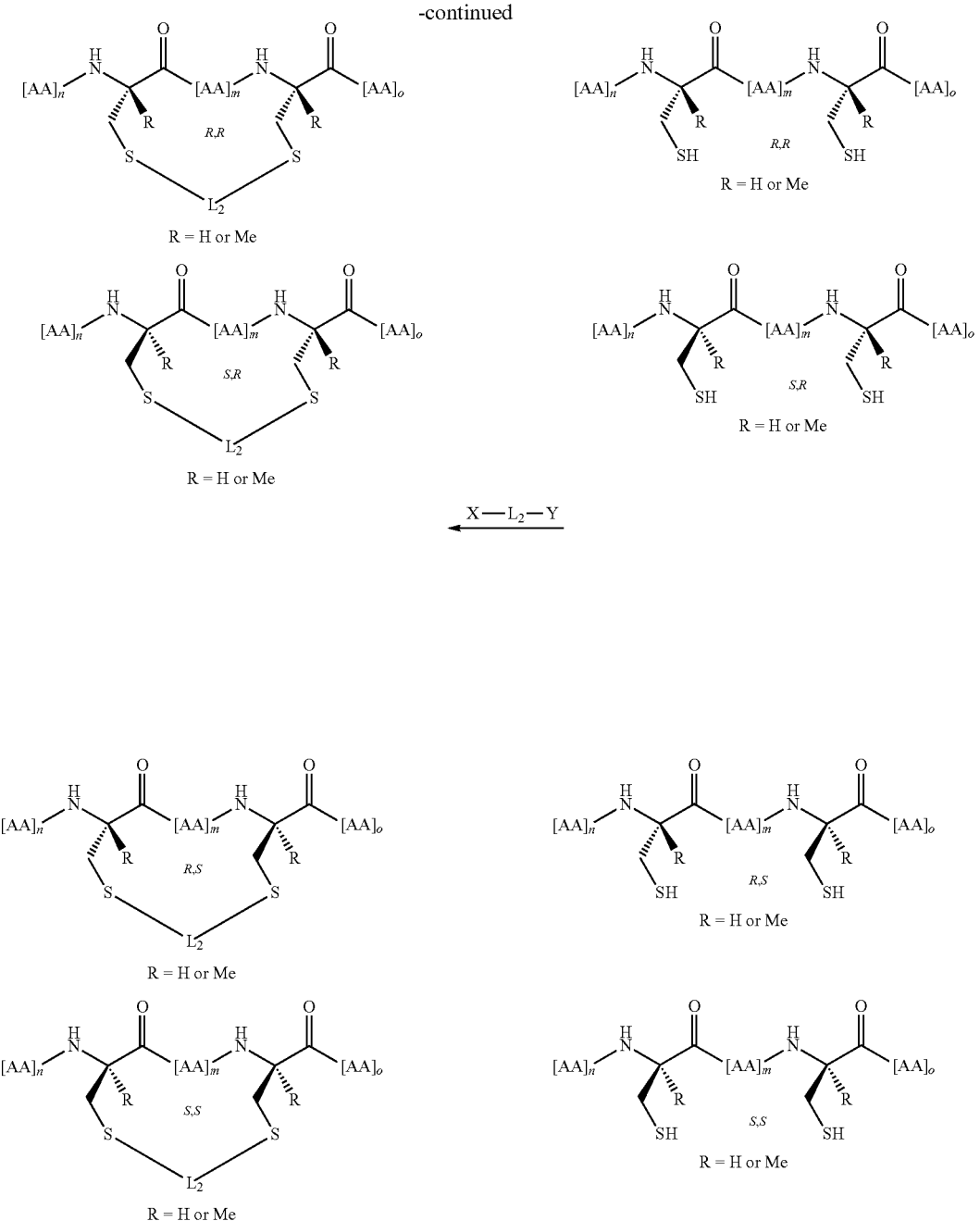

In Scheme 6, the peptidomimetic precursor contains two —SH moieties and is synthesized by solid-phase peptide synthesis (SPPS) using commercially available N-α-Fmoc amino acids such as N-α-Fmoc-S-trityl-L-cysteine or N-α-Fmoc-S-trityl-D-cysteine. Alpha-methylated versions of D-cysteine or L-cysteine are generated by known methods (Seebach et al. (1996), Angew. Chem. Int. Ed. Engl. 35:2708-2748, and references therein) and then converted to the appropriately protected N-α-Fmoc-S-trityl monomers by known methods ("Bioorganic Chemistry: Peptides and Proteins", Oxford University Press, New York: 1998, the entire contents of which are incorporated herein by reference). The precursor peptidomimetic is then deprotected and cleaved from the solid-phase resin by standard conditions (e.g., strong acid such as 95% TFA). The precursor peptidomimetic is reacted as a crude mixture or is purified prior to reaction with X-L$_2$-Y in organic or aqueous solutions. In some embodiments the alkylation reaction is performed under dilute conditions (i.e. 0.15 mmol/L) to favor macrocyclization and to avoid polymerization. In some embodiments, the alkylation reaction is performed in organic solutions such as liquid NH$_3$ (Mosberg et al. (1985), J. Am. Chem. Soc. 107:2986-2987; Szewczuk et al. (1992), Int. J. Peptide Protein Res. 40: 233-242), NH$_3$/MeOH, or NH$_3$/DMF (Or et al. (1991), J. Org. Chem. 56:3146-3149). In other embodiments, the alkylation is performed in an aqueous solution such as 6M guanidinium HCL, pH 8 (Brunel et al. (2005), Chem. Commun. (20):2552-2554). In other embodiments, the solvent used for the alkylation reaction is DMF or dichloroethane.

Synthetic Scheme 7:
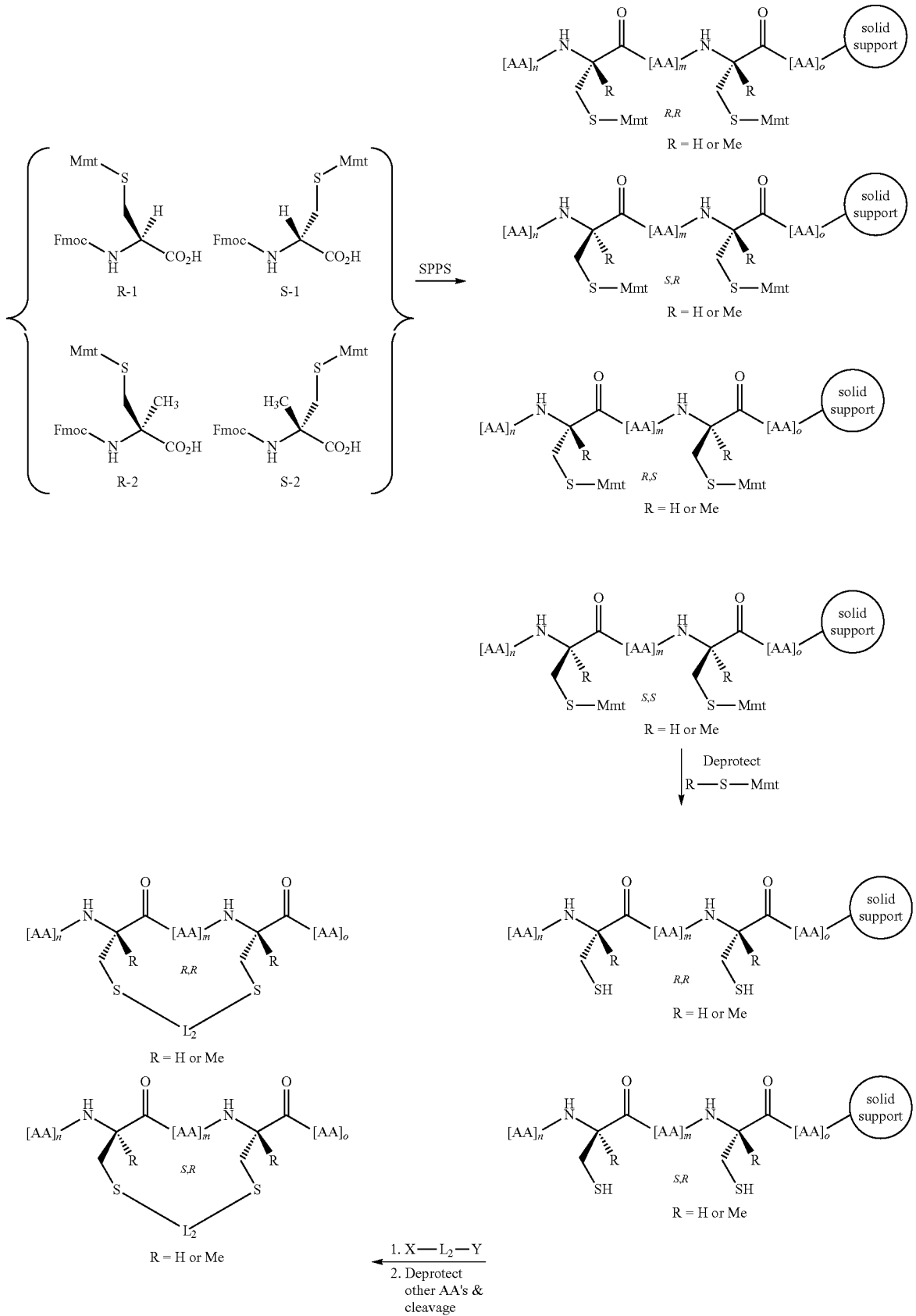

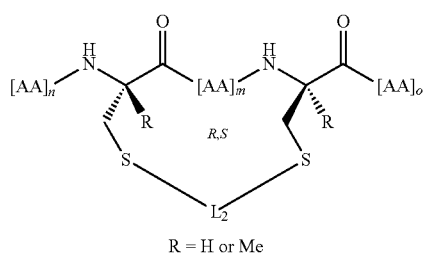

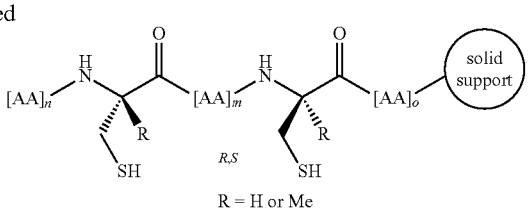

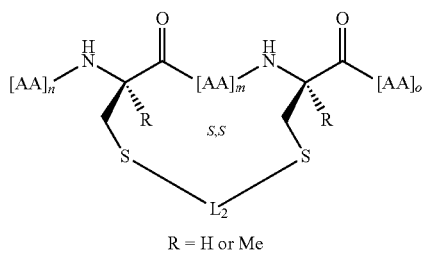

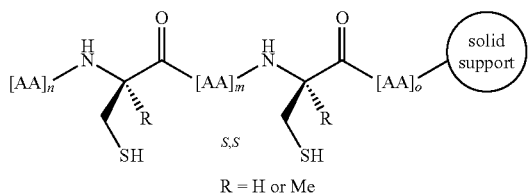

In Scheme 7, the precursor peptidomimetic contains two or more —SH moieties, of which two are specially protected to allow their selective deprotection and subsequent alkylation for macrocycle formation. The precursor peptidomimetic is synthesized by solid-phase peptide synthesis (SPPS) using commercially available N-α-Fmoc amino acids such as N-α-Fmoc-S-p-methoxytrityl-L-cysteine or N-α-Fmoc-S-p-methoxytrityl-D-cysteine. Alpha-methylated versions of D-cysteine or L-cysteine are generated by known methods (Seebach et al. (1996), *Angew. Chem. Int. Ed. Engl.* 35:2708-2748, and references therein) and then converted to the appropriately protected N-α-Fmoc-S-p-methoxytrityl monomers by known methods (*Bioorganic Chemistry: Peptides and Proteins*, Oxford University Press, New York: 1998, the entire contents of which are incorporated herein by reference). The Mmt protecting groups of the peptidomimetic precursor are then selectively cleaved by standard conditions (e.g., mild acid such as 1% TFA in DCM). The precursor peptidomimetic is then reacted on the resin with X-L$_2$-Y in an organic solution. For example, the reaction takes place in the presence of a hindered base such as diisopropylethylamine. In some embodiments, the alkylation reaction is performed in organic solutions such as liquid NH$_3$ (Mosberg et al. (1985), *J. Am. Chem. Soc.* 107:2986-2987; Szewczuk et al. (1992), *Int. J. Peptide Protein Res.* 40: 233-242), NH$_3$/MeOH or NH$_3$/DMF (Or et al. (1991), *J. Org. Chem.* 56:3146-3149). In other embodiments, the alkylation reaction is performed in DMF or dichloroethane. The crosslinked polypeptide is then deprotected and cleaved from the solid-phase resin by standard conditions (e.g., strong acid such as 95% TFA).

Synthetic Scheme 8:

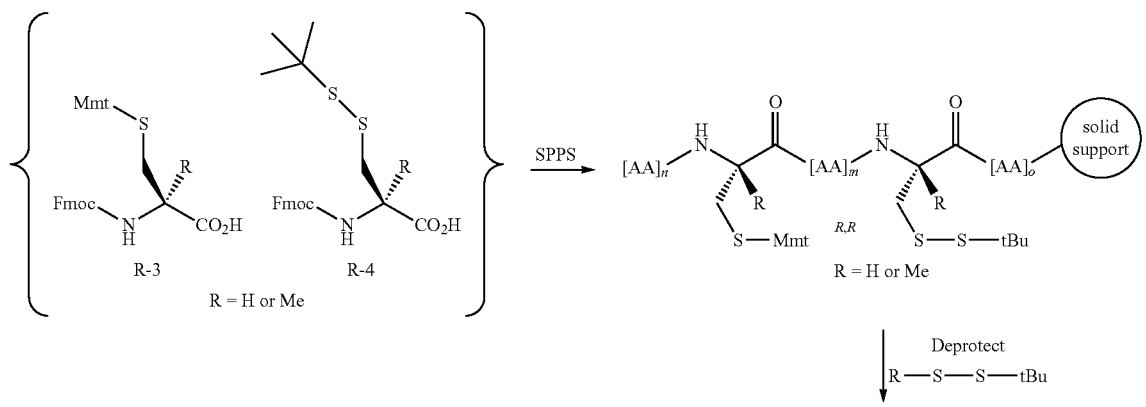

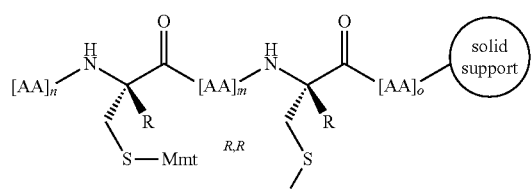
-continued
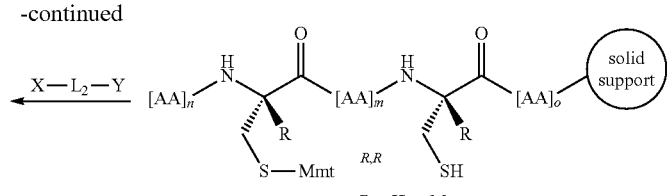

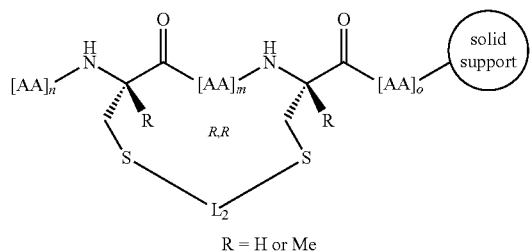
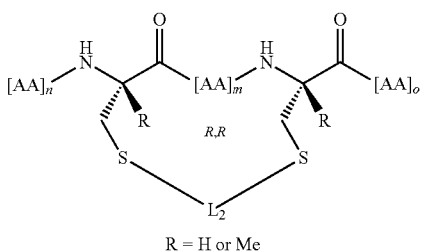

In Scheme 8, the peptidomimetic precursor contains two or more —SH moieties, of which two are specially protected to allow their selective deprotection and subsequent alkylation for macrocycle formation. The peptidomimetic precursor is synthesized by solid-phase peptide synthesis (SPPS) using commercially available N-α-Fmoc amino acids such as N-α-Fmoc-S-p-methoxytrityl-L-cysteine, N-α-Fmoc-S-p-methoxytrityl-D-cysteine, N-α-Fmoc-S—S-t-butyl-L-cysteine, and N-α-Fmoc-S—S-t-butyl-D-cysteine. Alpha-methylated versions of D-cysteine or L-cysteine are generated by known methods (Seebach et al. (1996), *Angew. Chem. Int. Ed. Engl.* 35:2708-2748, and references therein) and then converted to the appropriately protected N-α-Fmoc-S-p-methoxytrityl or N-α-Fmoc-S—S-t-butyl monomers by known methods (*Bioorganic Chemistry: Peptides and Proteins*, Oxford University Press, New York: 1998, the entire contents of which are incorporated herein by reference). The S—S-tButyl protecting group of the peptidomimetic precursor is selectively cleaved by known conditions (e.g., 20% 2-mercaptoethanol in DMF, reference: Galande et al. (2005), *J. Comb. Chem.* 7:174-177). The precursor peptidomimetic is then reacted on the resin with a molar excess of X-L$_2$-Y in an organic solution. For example, the reaction takes place in the presence of a hindered base such as diisopropylethylamine. The Mmt protecting group of the peptidomimetic precursor is then selectively cleaved by standard conditions (e.g., mild acid such as 1% TFA in DCM). The peptidomimetic precursor is then cyclized on the resin by treatment with a hindered base in organic solutions. In some embodiments, the alkylation reaction is performed in organic solutions such as NH$_3$/MeOH or NH$_3$/DMF (Or et al. (1991), *J. Org. Chem.* 56:3146-3149). The crosslinked polypeptide is then deprotected and cleaved from the solid-phase resin by standard conditions (e.g., strong acid such as 95% TFA).

Synthetic Scheme 9:

1. Biological synthesis of peptide
2. Purification of peptide

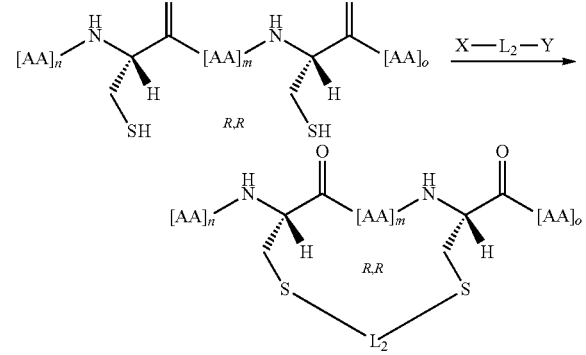

In Scheme 9, the peptidomimetic precursor contains two L-cysteine moieties. The peptidomimetic precursor is synthesized by known biological expression systems in living cells or by known in vitro, cell-free, expression methods. The precursor peptidomimetic is reacted as a crude mixture or is purified prior to reaction with X-L2-Y in organic or aqueous solutions. In some embodiments the alkylation reaction is performed under dilute conditions (i.e. 0.15 mmol/L) to favor macrocyclization and to avoid polymerization. In some embodiments, the alkylation reaction is performed in organic solutions such as liquid NH$_3$ (Mosberg et al. (1985), J. Am. Chem. Soc. 107:2986-2987; Szewczuk et al. (1992), Int. J. Peptide Protein Res. 40: 233-242), NH$_3$/MeOH, or NH$_3$/

DMF (Or et al. (1991), J. Org. Chem. 56:3146-3149). In other embodiments, the alkylation is performed in an aqueous solution such as 6M guanidinium HCL, pH 8 (Brunel et al. (2005), Chem. Commun. (20):2552-2554). In other embodiments, the alkylation is performed in DMF or dichloroethane. In another embodiment, the alkylation is performed in non-denaturing aqueous solutions, and in yet another embodiment the alkylation is performed under conditions that favor α-helical structure formation. In yet another embodiment, the alkylation is performed under conditions that favor the binding of the precursor peptidomimetic to another protein, so as to induce the formation of the bound α-helical conformation during the alkylation.

Various embodiments for X and Y are envisioned which are suitable for reacting with thiol groups. In general, each X or Y is independently be selected from the general category shown in Table 7. For example, X and Y are halides such as —Cl, —Br or —I. Any of the macrocycle-forming linkers described herein may be used in any combination with any of the sequences shown in Tables 1-4 and also with any of the R— substituents indicated herein.

TABLE 7

Examples of Reactive Groups Capable of Reacting with Thiol Groups and Resulting Linkages

| X or Y | Resulting Covalent Linkage |
|---|---|
| acrylamide | Thioether |
| halide (e.g. alkyl or aryl halide) | Thioether |
| sulfonate | Thioether |
| aziridine | Thioether |
| epoxide | Thioether |
| haloacetamide | Thioether |
| maleimide | Thioether |
| sulfonate ester | Thioether |

Table 8 shows exemplary macrocycles of the invention (SEQ ID NOS 101-106, respectively, in order of appearance). "$N_L$" represents norleucine and replaces a methionine residue. It is envisioned that similar linkers are used to synthesize crosslinked polypeptides based on the polypeptide sequences disclosed in Table 1 through Table 4.

TABLE 8

Examples of Crosslinked polypeptides of the Invention

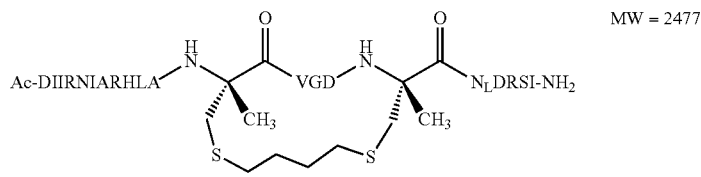

MW = 2477

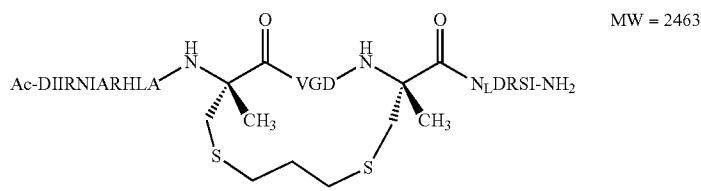

MW = 2463

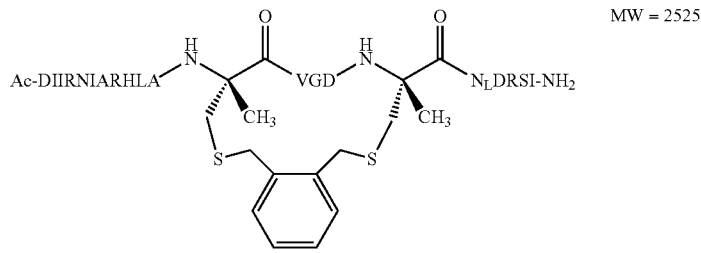

MW = 2525

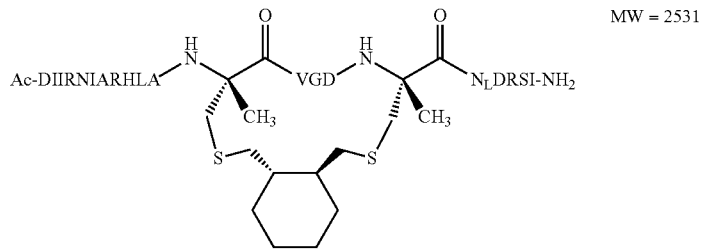

MW = 2531

TABLE 8-continued

Examples of Crosslinked polypeptides of the Invention

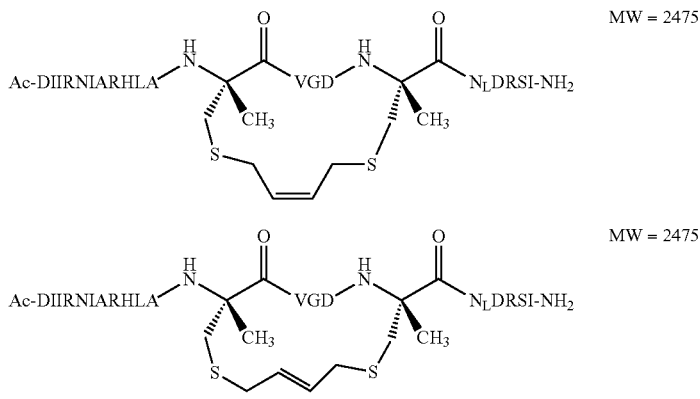

MW = 2475

MW = 2475

For the examples shown in this table, "$N_L$" represents norleucine.

The present invention contemplates the use of both naturally-occurring and non-naturally-occurring amino acids and amino acid analogs in the synthesis of the crosslinked polypeptides of Formula (III). Any amino acid or amino acid analog amenable to the synthetic methods employed for the synthesis of stable bis-sulfhydryl containing crosslinked polypeptides can be used in the present invention. For example, cysteine is contemplated as a useful amino acid in the present invention. However, sulfur containing amino acids other than cysteine that contain a different amino acid side chain are also useful. For example, cysteine contains one methylene unit between the α-carbon of the amino acid and the terminal —SH of the amino acid side chain. The invention also contemplates the use of amino acids with multiple methylene units between the α-carbon and the terminal —SH. Non-limiting examples include α-methyl-L-homocysteine and α-methyl-D-homocysteine. In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-cysteine and α-methyl-D-cysteine.

The invention includes macrocycles in which macrocycle-forming linkers are used to link two or more —SH moieties in the peptidomimetic precursors to form the crosslinked polypeptides of the invention. As described above, the macrocycle-forming linkers impart conformational rigidity, increased metabolic stability and/or increased cell penetrability. Furthermore, in some embodiments, the macrocycle-forming linkages stabilize the α-helical secondary structure of the peptidomimetic macrocycles. The macrocycle-forming linkers are of the formula X-$L_2$-Y, wherein both X and Y are the same or different moieties, as defined above. Both X and Y have the chemical characteristics that allow one macrocycle-forming linker -$L_2$- to bis alkylate the bis-sulfhydryl containing peptidomimetic precursor. As defined above, the linker -$L_2$-includes alkylene, alkenylene, alkynylene, heteroalkylene, cycloalkylene, heterocycloalkylene, cycloarylene, or heterocycloarylene, or —$R_4$—K—$R_4$—, all of which can be optionally substituted with an $R_5$ group, as defined above. Furthermore, one to three carbon atoms within the macrocycle-forming linkers -$L_2$-, other than the carbons attached to the —SH of the sulfhydryl containing amino acid, are optionally substituted with a heteroatom such as N, S or O.

The $L_2$ component of the macrocycle-forming linker X-$L_2$-Y may be varied in length depending on, among other things, the distance between the positions of the two amino acid analogs used to form the crosslinked polypeptide. Furthermore, as the lengths of $L_1$ and/or $L_3$ components of the macrocycle-forming linker are varied, the length of $L_2$ can also be varied in order to create a linker of appropriate overall length for forming a stable crosslinked polypeptide. For example, if the amino acid analogs used are varied by adding an additional methylene unit to each of $L_1$ and $L_3$, the length of $L_2$ are decreased in length by the equivalent of approximately two methylene units to compensate for the increased lengths of $L_1$ and $L_3$.

In some embodiments, $L_2$ is an alkylene group of the formula —$(CH_2)_n$—, where n is an integer between about 1 and about 15. For example, n is 1, 2, 3, 4, 5, 6, 7, 8, 9 or 10. In other embodiments, $L_2$ is an alkenylene group. In still other embodiments, $L_2$ is an aryl group.

Table 9 shows additional embodiments of X-$L_2$-Y groups.

TABLE 9

Exemplary X—$L_2$—Y groups of the invention.

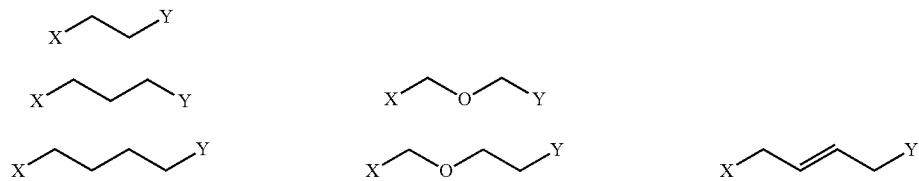

TABLE 9-continued

Exemplary X—L₂—Y groups of the invention.

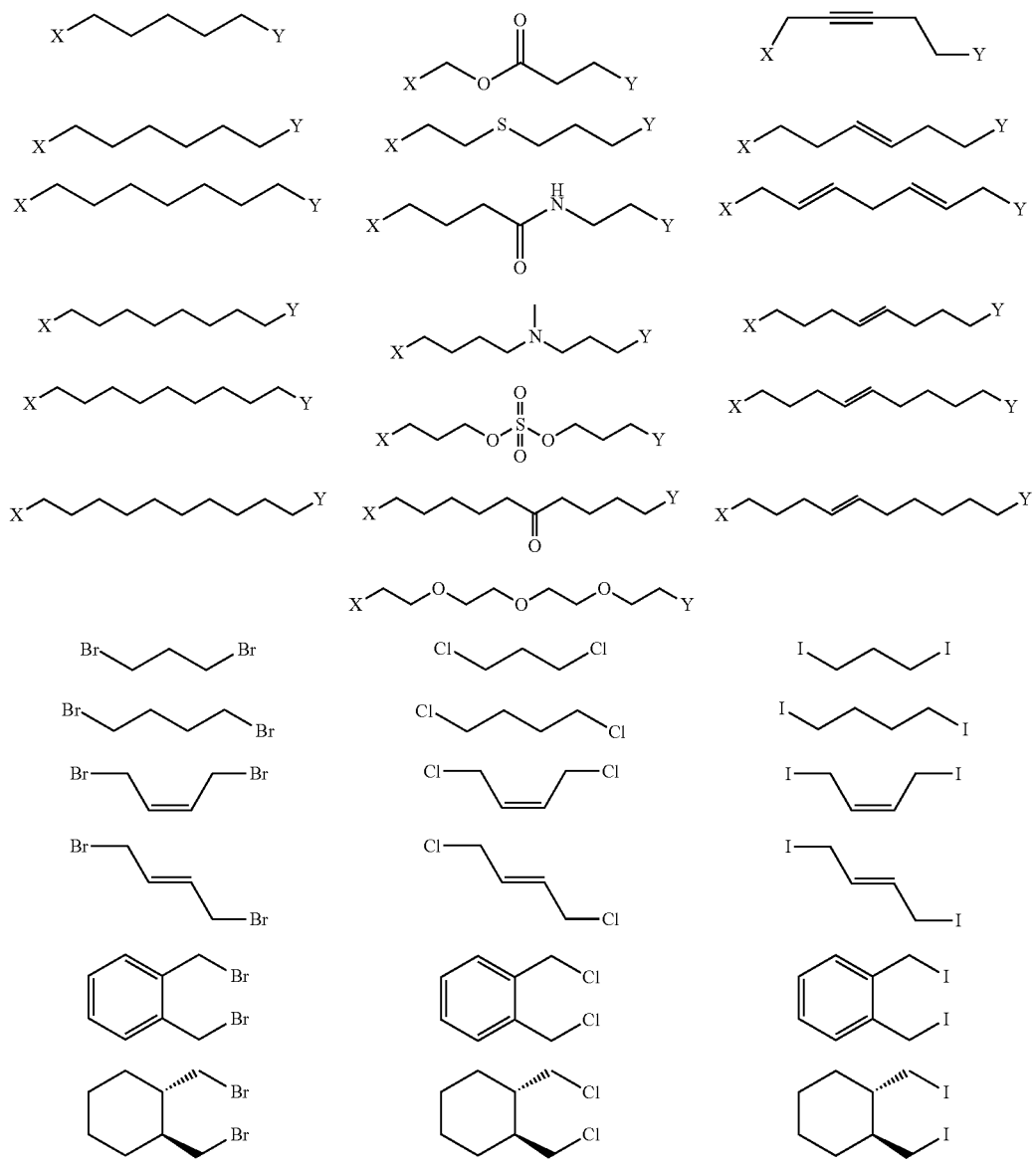

Each X and Y in this table, is, for example, independently Cl—, Br— or I—.

Additional methods of forming crosslinked polypeptides which are envisioned as suitable to perform the present invention include those disclosed by Mustapa, M. Firouz Mohd et al., J. Org. Chem (2003), 68, pp. 8193-8198; Yang, Bin et al. Bioorg Med. Chem. Lett. (2004), 14, pp. 1403-1406; U.S. Pat. Nos. 5,364,851; 5,446,128; 5,824,483; 6,713,280; and 7,202,332. In such embodiments, aminoacid precursors are used containing an additional substituent R— at the alpha position. Such aminoacids are incorporated into the macrocycle precursor at the desired positions, which may be at the positions where the crosslinker is substituted or, alternatively, elsewhere in the sequence of the macrocycle precursor. Cyclization of the precursor is then effected according to the indicated method.

Assays

The properties of the crosslinked polypeptides of the invention are assayed, for example, by using the methods described below.

Assay to Determine α-helicity.

In solution, the secondary structure of polypeptides with α-helical domains will reach a dynamic equilibrium between random coil structures and α-helical structures, often expressed as a "percent helicity". Thus, for example, unmodified pro-apoptotic BH3 domains are predominantly random coils in solution, with α-helical content usually under 25%. Peptidomimetic macrocycles with optimized linkers, on the other hand, possess, for example, an alpha-helicity that is at least two-fold greater than that of a corresponding uncrosslinked polypeptide. In some embodiments, macrocycles of the invention will possess an alpha-helicity of greater than 50%. To assay the helicity of peptidomimetic macrocycles of the invention, such as BH3 domain-based macrocycles, the compounds are dissolved in an aqueous solution (e.g. 50 mM potassium phosphate solution at pH 7, or distilled $H_2O$, to concentrations of 25-50 µM). Circular dichroism (CD) spectra are obtained on a spectropolarimeter (e.g., Jasco J-710) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity (e.g. [Φ]222obs) by the reported value for a model helical decapeptide (Yang et al. (1986), *Methods Enzymol.* 130:208)).

Assay to Determine Melting Temperature I.

A peptidomimetic macrocycle of the invention comprising a secondary structure such as an α-helix exhibits, for example, a higher melting temperature than a corresponding uncrosslinked polypeptide. Typically peptidomimetic macrocycles of the invention exhibit Tm of >60° C. representing a highly stable structure in aqueous solutions. To assay the effect of macrocycle formation on meltine temperature, peptidomimetic macrocycles or unmodified peptides are dissolved in distilled $H_2O$ (e.g. at a final concentration of 50 µM) and the Tm is determined by measuring the change in ellipticity over a temperature range (e.g. 4 to 95° C.) on a spectropolarimeter (e.g., Jasco J-710) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

Protease Resistance Assay.

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention may be subjected to in vitro trypsin proteolysis to assess for any change in degradation rate compared to a corresponding uncrosslinked polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time (k=−1×slope).

Ex Vivo Stability Assay.

Peptidomimetic macrocycles with optimized linkers possess, for example, an ex vivo half-life that is at least two-fold greater than that of a corresponding uncrosslinked polypeptide, and possess an ex vivo half-life of 12 hours or more. For ex vivo serum stability studies, a variety of assays may be used. For example, a peptidomimetic macrocycle and/or a corresponding uncrosslinked polypeptide (2 mcg) are each incubated with fresh mouse, rat and/or human serum (e.g. 1-2 mL) at 37° C. for 0, 1, 2, 4, 8, and 24 hours. Samples of differing macrocycle concentration may be prepared by serial dilution with serum. To determine the level of intact compound, the following procedure may be used: The samples are extracted by transferring 100 µl of sera to 2 ml centrifuge tubes followed by the addition of 10 µL of 50% formic acid and 500 µL acetonitrile and centrifugation at 14,000 RPM for 10 min at 4±2° C. The supernatants are then transferred to fresh 2 ml tubes and evaporated on Turbovap under $N_2$<10 psi, 37° C. The samples are reconstituted in 1004 of 50:50 acetonitrile:water and submitted to LC-MS/MS analysis. Equivalent or similar procedures for testing ex vivo stability are known and may be used to determine stability of macrocycles in serum.

In Vitro Binding Assays.

To assess the binding and affinity of peptidomimetic macrocycles and peptidomimetic precursors to acceptor proteins, a fluorescence polarization assay (FPA) is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

For example, fluoresceinated peptidomimetic macrocycles (25 nM) are incubated with the acceptor protein (25-1000nM) in binding buffer (140 mM NaCl, 50 mM Tris-HCL, pH 7.4) for 30 minutes at room temperature. Binding activity is measured, for example, by fluorescence polarization on a luminescence spectrophotometer (e.g. Perkin-Elmer LS50B). Kd values may be determined by nonlinear regression analysis using, for example, Graphpad Prism software (GraphPad Software, Inc., San Diego, Calif.). A peptidomimetic macrocycle of the invention shows, in some instances, similar or lower Kd than a corresponding uncrosslinked polypeptide.

Acceptor proteins for BH3-peptides such as BCL-2, BCL-$X_L$, BAX or MCL1 may, for example, be used in this assay. Acceptor proteins for p53 peptides such as MDM2 or MDMX may also be used in this assay.

In Vitro Displacement Assays to Characterize Antagonists of Peptide-Protein Interactions.

To assess the binding and affinity of compounds that antagonize the interaction between a peptide (e.g. a BH3 peptide or a p53 peptide) and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

For example, putative antagonist compounds (1 nM to 1 mM) and a fluoresceinated peptidomimetic macrocycle (25 nM) are incubated with the acceptor protein (50 nM) in binding buffer (140 mM NaCl, 50 mM Tris-HCL, pH 7.4) for 30 minutes at room temperature. Antagonist binding activity is measured, for example, by fluorescence polarization on a luminescence spectrophotometer (e.g. Perkin-Elmer LS50B). Kd values may be determined by nonlinear regression analysis using, for example, Graphpad Prism software (GraphPad Software, Inc., San Diego, Calif.).

Any class of molecule, such as small organic molecules, peptides, oligonucleotides or proteins can be examined as putative antagonists in this assay. Acceptor proteins for BH3-peptides such as BCL2, BCL-XL, BAX or MCL1 can be used in this assay. Acceptor proteins for p53 peptides such as MDM2 or MDMX can be used in this assay.

Binding Assays in Intact Cells.

It is possible to measure binding of peptides or crosslinked polypeptides to their natural acceptors in intact cells by immunoprecipitation experiments. For example, intact cells are incubated with fluoresceinated (FITC-labeled) compounds for 4-24 hrs in the absence or presence of serum. Cells are then pelleted and incubated in lysis buffer (50 mM Tris [pH 7.6], 150 mM NaCl, 1% CHAPS and protease inhibitor cocktail) for 10 minutes at 4° C. Extracts are centrifuged at 14,000 rpm for 15 minutes and supernatants collected and incubated with 10 µl goat anti-FITC antibody for 2 hrs, rotating at 4° C. followed by further 2 hrs incubation at 4° C. with protein A/G Sepharose (50 µl of 50% bead slurry). After quick centrifugation, the pellets are washed in lysis buffer containing increasing salt concentration (e.g., 150, 300, 500 mM). The beads are then re-equilibrated at 150 mM NaCl before addition of SDS-containing sample buffer and boiling. After centrifugation, the supernatants are optionally electrophoresed using 4%-12% gradient Bis-Tris gels followed by transfer into Immobilon-P membranes. After blocking, blots are optionally incubated with an antibody that detects FITC and also with one or more antibodies that detect proteins that bind to the crosslinked polypeptide, including BCL2, MCL1, BCL-XL, A1, BAX, BAK, MDM2 or MDMX.

Cellular Penetrability Assays.

To measure the cell penetrability of peptides or crosslinked polypeptides, intact cells are incubated with fluoresceinated crosslinked polypeptides (10 µM) for 4 hrs in serum-free media or in media supplemented with human serum at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KINETICSCAN® HCS Reader (An automated device for analysis of cellular and intracellular spatial parameters, over time, in populations of living cells).

Cellular Efficacy Assays.

The efficacy of certain crosslinked polypeptides is determined, for example, in cell-based killing assays using a variety of tumorigenic and non-tumorigenic cell lines and primary cells derived from human or mouse cell populations. Cell viability is monitored, for example, over 24-96 hrs of incubation with crosslinked polypeptides (0.5 to 50 µM) to identify those that kill at EC50<10 µM. Several standard assays that measure cell viability are commercially available and are optionally used to assess the efficacy of the crosslinked polypeptides. In addition, assays that measure Annexin V and caspase activation are optionally used to assess whether the crosslinked polypeptides kill cells by activating the apoptotic machinery. For example, the Cell Titer-glo assay is used which determines cell viability as a function of intracellular ATP concentration.

In Vivo Stability Assay.

To investigate the in vivo stability of crosslinked polypeptides, the compounds are, for example,administered to mice and/or rats by IV, IP, PO or inhalation routes at concentrations ranging from 0.1 to 50 mg/kg and blood specimens withdrawn at 0', 5', 15', 30', 1 hr, 4 hrs, 8 hrs and 24 hours post-injection. Levels of intact compound in 25 µL of fresh serum are then measured by LC-MS/MS as above.

In Vivo Efficacy in Animal Models.

To determine the anti-oncogenic activity of crosslinked polypeptides of the invention in vivo, the compounds are, for example, given alone (IP, IV, PO, by inhalation or nasal routes) or in combination with sub-optimal doses of relevant chemotherapy (e.g., cyclophosphamide, doxorubicin, etoposide). In one example, $5 \times 10^6$ RS4;11 cells (established from the bone marrow of a patient with acute lymphoblastic leukemia) that stably express luciferase are injected by tail vein in NOD-SCID mice 3 hrs after they have been subjected to total body irradiation. If left untreated, this form of leukemia is fatal in 3 weeks in this model. The leukemia is readily monitored, for example, by injecting the mice with D-luciferin (60 mg/kg) and imaging the anesthetized animals (e.g., Xenogen In Vivo Imaging System, Caliper Life Sciences, Hopkinton, Mass.). Total body bioluminescence is quantified by integration of photonic flux (photons/sec) by Living Image Software (Caliper Life Sciences, Hopkinton, Mass.). Peptidomimetic macrocycles alone or in combination with sub-optimal doses of relevant chemotherapeutics agents are, for example, administered to leukemic mice (10 days after injection/day 1 of experiment, in bioluminescence range of 14-16) by tail vein or IP routes at doses ranging from 0.1 mg/kg to 50 mg/kg for 7 to 21 days. Optionally, the mice are imaged throughout the experiment every other day and survival monitored daily for the duration of the experiment. Expired mice are optionally subjected to necropsy at the end of the experiment. Another animal model is implantation into NOD-SCID mice of DoHH2, a cell line derived from human follicular lymphoma, that stably expresses luciferase. These in vivo tests optionally generate preliminary pharmacokinetic, pharmacodynamic and toxicology data.

Clinical Trials.

To determine the suitability of the crosslinked polypeptides of the invention for treatment of humans, clinical trials are performed. For example, patients diagnosed with cancer and in need of treatment are selected and separated in treatment and one or more control groups, wherein the treatment group is administered a crosslinked polypeptide of the invention, while the control groups receive a placebo or a known anti-cancer drug. The treatment safety and efficacy of the crosslinked polypeptides of the invention can thus be evaluated by performing comparisons of the patient groups with respect to factors such as survival and quality-of-life. In this example, the patient group treated with a crosslinked polypeptide show improved long-term survival compared to a patient control group treated with a placebo.

Pharmaceutical Compositions and Routes of Administration

The crosslinked polypeptides of the invention also include pharmaceutically acceptable derivatives or prodrugs thereof. A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention. Particularly favored pharmaceutically acceptable derivatives are those that increase the bioavailability of the compounds of the invention when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa.

In some embodiments, the crosslinked polypeptides of the invention are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton, Pa.

In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including ranul and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution. The term "parenteral" as used herein typically refers to modes of administration including intravenous, intraarterial, intramuscular, intraperitoneal, intrasternal, and subcutaneous.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

When the compositions of this invention comprise a combination of a crosslinked polypeptide and one or more additional therapeutic or prophylactic agents, both the compound and the additional agent should be present at dosage levels of between about 1 to 100%, and more preferably between about 5 to 95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

Methods of administration that can be used in the present invention include but are not limited to intradermal, intramuscular, intraperitoneal, intravenous, subcutaneous, intranasal, epidural, oral, sublingual, intracerebral, intravaginal, transdermal, rectal, by inhalation, or topical by application to ears, nose, eyes, or skin.

Methods of Use

In one aspect, the present invention provides novel crosslinked polypeptides that are useful in competitive binding assays to identify agents which bind to the natural ligand(s) of the proteins or peptides upon which the crosslinked polypeptides are modeled. For example, in the p53 MDM2 system, labeled stabilized crosslinked polypeptides based on the p53 is used in an MDM2 binding assay along with small molecules that competitively bind to MDM2. Competitive binding studies allow for rapid in vitro evaluation and determination of drug candidates specific for the p53/MDM2 system. Likewise in the BH3/BCL-$X_L$ anti-apoptotic system labeled crosslinked polypeptides based on BH3 can be used in a BCL-$X_L$ binding assay along with small molecules that competitively bind to BCL-$X_L$. Competitive binding studies allow for rapid in vitro evaluation and determination of drug candidates specific for the BH3/BCL-$X_L$ system. The invention further provides for the generation of antibodies against the crosslinked polypeptides. In some embodiments, these antibodies specifically bind both the crosslinked polypeptides and the p53 or BH3 crosslinked polypeptide precursors upon which the crosslinked polypeptides are derived. Such antibodies, for example, disrupt the p53/MDM2 or BH3/BCL-XL systems, respectively.

In another aspect, the present invention provides for both prophylactic and therapeutic methods of treating a subject at risk of (or susceptible to) a disorder or having a disorder associated with aberrant (e.g., insufficient or excessive) BCL-2 family member expression or activity (e.g., extrinsic or intrinsic apoptotic pathway abnormalities). It is believed that some BCL-2 type disorders are caused, at least in part, by an abnormal level of one or more BCL-2 family members (e.g., over or under expression), or by the presence of one or more BCL-2 family members exhibiting abnormal activity. As such, the reduction in the level and/or activity of the BCL-2 family member or the enhancement of the level and/or activity of the BCL-2 family member, is used, for example, to ameliorate or reduce the adverse symptoms of the disorder.

In another aspect, the present invention provides methods for treating or preventing hyperproliferative disease by interfering with the interaction or binding between p53 and MDM2 in tumor cells. These methods comprise administering an effective amount of a compound of the invention to a warm blooded animal, including a human, or to tumor cells containing wild type p53. In some embodiments, the administration of the compounds of the present invention induces cell growth arrest or apoptosis. In other or further embodiments, the present invention is used to treat disease and/or tumor cells comprising elevated MDM2 levels. Elevated levels of MDM2 as used herein refers to MDM2 levels greater than those found in cells containing more than the normal copy number (2) of mdm2 or above about 10,000 molecules of MDM2 per cell as measured by ELISA and similar assays (Picksley et al. (1994), *Oncogene* 9, 2523 2529).

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In some embodiments, the crosslinked polypeptides of the invention are used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth. Examples of non-pathologic hyperproliferative cells include proliferation of cells associated with wound repair. Examples of cellular proliferative and/or differentiative disorders include cancer, e.g., carcinoma, sarcoma, or metastatic disorders. In some embodiments, the peptidomimetics macrocycles are novel therapeutic agents for controlling breast cancer, ovarian cancer, colon cancer, lung cancer, metastasis of such cancers and the like.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991), *Crit Rev. Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, ranulose-theca cell tumors, thecomafibromas, androblastomas, hill cell tumors, and gonadoblastoma; and metastatic tumors such as Krukenberg tumors.

In other or further embodiments, the peptidomimetics macrocycles described herein are used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, myelodysplasia In other or further embodiments, the crosslinked polypeptides of the invention that act to decrease apoptosis are used to treat disorders associated with an undesirable level of cell death. Thus, in some embodiments, the anti-apoptotic crosslinked polypeptides of the invention are used to treat disorders such as those that lead to cell death associated with viral infection, e.g., infection associated with infection with human immunodeficiency virus (HIV). A wide variety of neurological diseases are characterized by the gradual loss of specific sets of neurons, and the anti-apoptotic crosslinked polypeptides of the invention are used, in some embodiments, in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. In other or further embodiments, the anti-apoptotic crosslinked polypeptides of the invention are used to treat all such disorders associated with undesirable cell death.

Some examples of immunologic disorders that are treated with the crosslinked polypeptides described herein include but are not limited to organ transplant rejection, arthritis, lupus, IBD, Crohn's disease, asthma, multiple sclerosis, diabetes, etc.

Some examples of neurologic disorders that are treated with the crosslinked polypeptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a prion-mediated disease, and Huntington's Disease.

Some examples of endocrinologic disorders that are treated with the crosslinked polypeptides described herein include but are not limited to diabetes, hypothyroidism, hypopituitarism, hypoparathyroidism, hypogonadism, etc.

Examples of cardiovascular disorders (e.g., inflammatory disorders) that are treated or prevented with the crosslinked polypeptides of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

EXAMPLES

The following section provides illustrative examples of the present invention.

Example 1

Synthesis of Crosslinked polypeptides of Formula (I)

α-helical crosslinked polypeptides are synthesized, purified and analyzed as previously described (Schafmeister et al. (2000), J. Am. Chem. Soc. 122:5891-5892; Walensky et al (2004) Science 305:1466-70; Walensky et al (2006) Mol Cell 24:199-210) and as indicated below. The following macrocycles derived from the human BID BH3 (SEQ ID NOS 107-115, respectively, in order of appearance), human BIM BH3 (SEQ ID NOS 116-122, respectively, in order of appearance) and human MAML peptide sequences (SEQ ID NOS 123-125, respectively, in order of appearance) are used in this study:

TABLE 10

| Compound Number | Parent Peptide | Sequence | Calculated m/z (M + H) | Calculated m/z (M + 3H) | Found m/z (M + 3H) |
|---|---|---|---|---|---|
| 1 | BID | Ac-DIIRNIARHLA$VGD$NleDRSI-NH2 | 2438.40 | 813.47 | 813.7 |
| 2 | BID | Ac-DAARNIARHLA$VAibD$NleARSI-NH2 | 2338.35 | 780.12 | 780.17 |
| 3 | BID | Ac-DIARNIARHLA$VAibD$NleARSI-NH2 | 2380.39 | 794.14 | 794.15 |
| 4 | BID | Ac-DAIRNIARHLA$VAibD$NleARSI-NH2 | 2380.39 | 794.14 | 794.09 |
| 5 | BID | Pr-RNIARHLA$VAibD$NleDRSI-NH2 | 2139.25 | 713.76 | 713.79 |
| 6 | BID | Pr-RNIARHLAib$VAibD$NleDRSI-NH2 | 2153.27 | 718.43 | 718.5 |

TABLE 10-continued

| Compound Number | Parent Peptide | Sequence | Calculated m/z (M + H) | Calculated m/z (M + 3H) | Found m/z (M + 3H) |
|---|---|---|---|---|---|
| 7 | BID | Pr-RNIARHLA$VAibD$FARSI-NH2 | 2129.25 | 710.42 | 710.3 |
| 8 | BID | Pr-RNIARHLA$VGD$NleAibRSI-NH2 | 2081.25 | 694.42 | 694.42 |
| 9 | BID | Pr-RNIAibRHLAib$VAibD$AARSI-NH2 | 2081.25 | 694.42 | 694.49 |
| 10 | BIM | Ac-IWIAQELR$IGD$FNAYYARR-NH2 | 2646.43 | 882.82 | 883.15 |
| 11 | BIM | Ac-IWIAQQLR$IGD$FNAYYARR-NH2 | 2645.45 | 882.49 | 882.62 |
| 12 | BIM | Ac-IWIAQALR$IGD$FNAYYARR-NH2 | 2588.43 | 863.48 | 863.85 |
| 13 | BIM | Ac-RWIAQQLR$IGD$FNAYYARR-NH2 | 2688.46 | 896.83 | 896.84 |
| 14 | BIM | Ac-RWIAQALR$IGD$FNAFYARR-NH2 | 2615.45 | 872.49 | 872.64 |
| 15 | BIM | Ac-RWIAQALR$IGN$FNAYYARR-NH2 | 2630.45 | 877.48 | 877.36 |
| 16 | BIM | Ac-IWIAQALR$IGN$FNAYYARR-NH2 | 2587.43 | 863.14 | 863.00 |
| 17 | hMAML | Ac-ERLRRRI$LCR$HHST-NH2 | 2124.21 | 709.08 | 708.72 |
| 18 | hMAML | Ac-ERLRRRI$LAR$HHST-NH2 | 2092.24 | 698.42 | 698.09 |
| 19 | hMAML | Ac-ALRRRI$LCA$HHST-NH2 | 1825.04 | 609.35 | 609.06 |

In the sequences above, compound 1, 10 and 17 are reference compounds having high efficacy in serum-free media, which is substantially reduced in the presence of serum. Variants of this compound (2-9, 11-16, 18-19) are then made and tested using the methods of the invention. Nle represents norleucine, Aib represents 2-aminoisobutyric acid, Chg represents cyclohexylglycine, Ac represents N-terminal acetyl, Pr represents N-terminal proprionyl and $NH_2$ represents C-terminal amide. Amino acids represented as $ connect an all-carbon crosslinker comprising eight carbon atoms between the alpha carbons of each amino acid with a double bond between the fourth and fifth carbon atoms and wherein each α-carbon atom to which the crosslinker is attached is additionally substituted with a methyl group. Predicted and measured m/z spectra are provided.

Alpha,alpha-disubstituted non-natural amino acids containing olefinic side chains are synthesized according to Williams et al. (1991) J. Am. Chem. Soc. 113:9276; and Schafmeister et al. (2000) J. Am. Chem Soc. 122:5891. Crosslinked polypeptides are designed by replacing two naturally occurring amino acids (see Table 10 and FIG. 5) with the corresponding synthetic amino acids. Substitutions are made at i and i+4 positions or at i and i+7 positions. Crosslinked polypeptides are generated by solid phase peptide synthesis followed by olefin metathesis-based crosslinking of the synthetic amino acids via their olefin-containing side chains.

The non-natural amino acids (R and S enantiomers of the 5-carbon olefinic amino acid and the S enantiomer of the 8-carbon olefinic amino acid) are characterized by nuclear magnetic resonance (NMR) spectroscopy (Varian Mercury 400) and mass spectrometry (Micromass LCT). Peptide synthesis is performed either manually or on an automated peptide synthesizer (Applied Biosystems, model 433A), using solid phase conditions, rink amide AM resin (Novabiochem), and Fmoc main-chain protecting group chemistry. For the coupling of natural Fmoc-protected amino acids (Novabiochem), 10 equivalents of amino acid and a 1:1:2 molar ratio of coupling reagents HBTU/HOBt (Novabiochem)/DIEA are employed. Non-natural amino acids (4 equiv) are coupled with a 1:1:2 molar ratio of HATU (Applied Biosystems)/HOBt/DIEA. Olefin metathesis is performed in the solid phase using 10 mM Grubbs catalyst (Blackewell et al. 1994 supra) (Materia) dissolved in degassed dichloromethane and reacted for 2 hours at room temperature. Isolation of metathesized compounds is achieved by trifluoroacetic acid-mediated deprotection and cleavage, ether precipitation to yield the crude product, and high performance liquid chromatography (HPLC) (Varian ProStar) on a reverse phase C18 column (Varian) to yield the pure compounds. Chemical composition of the pure products is confirmed by LC/MS mass spectrometry (Micromass LCT interfaced with Agilent 1100 HPLC system) and amino acid analysis (Applied Biosystems, model 420A).

Example 2

Cell Viability Assays of Tumor Cell Lines Treated with Crosslinked Polypeptides of the Invention Jurkat cell line (Clone E6-1, ATCC catalog #TIB-152) is grown in specific serum-supplemented media (RPMI-1640, Invitrogen catalog #22400) as recommended by ATCC. A day prior to the initiation of the study, cells are split at optimal cell density ($2\times10^5$-$5\times10^5$ cells/ml) to assure actively dividing cells. The next day, cells are washed twice in serum-free Opti-MEM media (Invitrogen, Catalog #51985) and cells are then plated at optimal cell density (10,000 cells/well) in 50 µl Opti-MEM media or Opti-MEM supplemented with 2% or 10% human serum (Bioreclamation, catalog #HMSRM) in 96-well white tissue culture plate (Nunc, catalog #136102).

For serum free experiment, crosslinked polypeptides are diluted from 2 mM stocks (100% DMSO) in sterile water to prepare 400 µM working solutions. The crosslinked polypeptides and controls are diluted 10-fold first and then serially two-fold diluted in Opti-MEM in dosing plates to provide concentrations of between 1.2 and 40 µM. 50 µL of each dilution is then added to the appropriate wells of the test plate to achieve final concentrations of the polypeptides equal to between 0.6 to 20 μM. For studies using Opti-MEM supplemented with human serum (Bioreclamation, catalog #HMSRM), crosslinked polypeptides are diluted from 10 mM stocks (100% DMSO) in sterile water to prepare 2 mM working solutions. The crosslinked polypeptides and controls are diluted 10-fold first and then serially two-fold diluted in Opti-MEM in the presence of 2% or 10% of human serum to provide concentrations of the polypeptides equal to between 6.25 to 200 μM in dosing plates. 50 μL of each dilution is then added to the appropriate wells of the test plate to achieve final concentrations of the polypeptides equal to between 3.125 to 100 μM. Controls included wells without polypeptides containing the same concentration of DMSO as the wells containing the macrocycles, wells containing 0.1% Triton X-100 and wells containing no cells. Plates are incubated for 24 hours at 37° C. in humidified 5% $CO_2$ atmosphere.

At the end of the incubation period, CellTiter-Glo assay is performed according to manufacturer's instructions (Promega, catalog #G7573) and luminescence is measured using Synergy HT Plate reader (BioTek). Luminescence correlates with viability. A reduction in viability reflects the ability of the test compounds to induce programmed cell death via BAX and BAK. A representative dose-response curve at increasing concentrations of human serum is shown in FIG. 1.

Example 3

Determination of Apparent Affinity to Human Serum Proteins ($K_d^*$)

The measurement of apparent $K_d$ values for serum protein by EC50 shift analysis provides a simple and rapid means of quantifying the propensity of experimental compounds to bind HSA and other serum proteins. A linear relationship exists between the apparent $EC_{50}$ in the presence of serum protein ($EC'_{50}$) and the amount of serum protein added to an in vitro assay. This relationship is defined by the binding affinity of the compound for serum proteins, expressed as $K_d^*$. This term is an experimentally determined, apparent dissociation constant that may result from the cumulative effects of multiple, experimentally indistinguishable, binding events. The form of this relationship is presented here in Eq. 0.3, and its derivation can be found in Copeland et al, *Biorg. Med Chem Lett.* 2004, 14:2309-2312.

$$EC'_{50} = EC_{50} + P\left(\frac{n}{1 + \frac{K_d^*}{EC_{50}}}\right) \quad (0.3)$$

A significant proportion of serum protein binding can be ascribed to drug interactions with HSA, due to the very high concentration of this protein in serum (35-50 g/L or 530-758 μM). To calculate the $K_d$ value for these compounds we have assumed that the shift in $EC_{50}$ upon protein addition can be ascribed fully to the HSA present in the added serum, where P is 700 μM for 100% serum, P is 70 μM for 10% serum, etc. We further made the simplifying assumption that all of the compounds bind HSA with a 1:1 stoichiometry, so that the term n in Eq. (0.3) is fixed at unity. With these parameters in place we calculated the $K_d^*$ value for each stapled peptide from the changes in $EC_{50}$ values with increasing serum (and serum protein) concentrations by nonlinear regression analysis of Eq. 0.3 using Mathematica 4.1 (Wolfram Research, Inc., www.wolfram.com). $EC'_{50}$ values in whole blood are estimated by setting P in Eq. 0.3 to 700 μM [HSA].

The free fraction in blood is estimated per the following equation, as derived by Trainor, *Expert Opin. Drug Disc.*, 2007, 2(1):51-64, where [HSA]$_{total}$ is set at 700 μM.

$$FreeFraction = \frac{K_d^*}{K_d^* + [HSA]_{total}} \quad (0.4)$$

Figure 2:
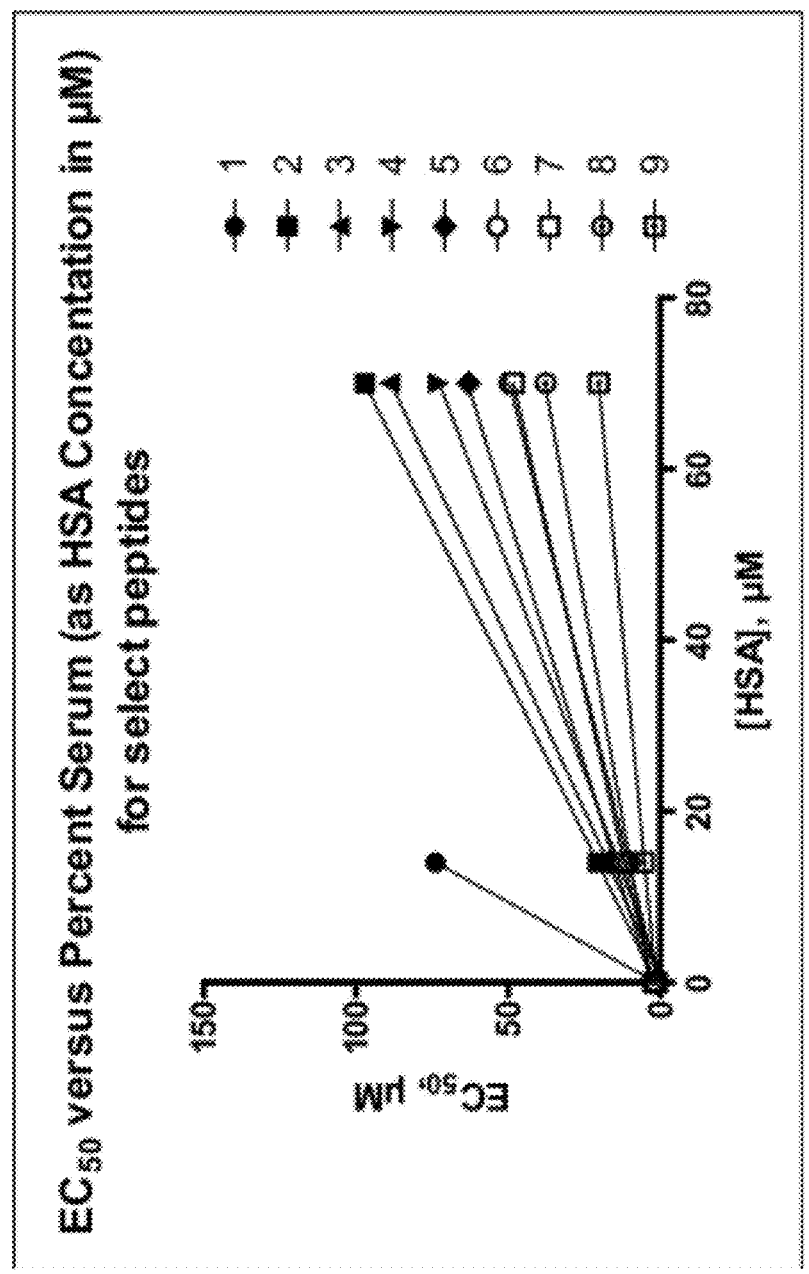
FIG. 2 shows a plot of cellular $EC_{50}$ vs human serum concentrations for peptidomimetic macrocycle analogs with improved properties.

FIG. 2 shows representative plots of EC50 vs human serum concentration for compound 1 and related analogs. FIG. 3 shows representative plots of EC50 vs human serum concentration for compound 10 and related analogs.

Table 11 shows that by selection and optimization in accordance with the invention, compounds can be made with substantially less serum shift than the initial lead (for example, compound 1 or compound 10) while still retaining good activity in the assay of Example 2.

TABLE 11

| Compound Number | No serum EC50, μM | 2% serum EC50, μM | 10% serum EC50, μM | Serum Kd* | Free Fraction est. in blood, μM | EC50 est. in blood, μM |
| --- | --- | --- | --- | --- | --- | --- |
| 1 | 1.2 | 73.9 | >100 | <0.1 | <0.1% | 3636.2 |
| 2 | 1.6 | 20.5 | 97.1 | <0.1 | <0.1% | 957.2 |
| 3 | 1.2 | 14.9 | 88.9 | <0.1 | <0.1% | 890.1 |
| 4 | 1.0 | 11.3 | 73.1 | <0.1 | <0.1% | 734.8 |
| 5 | 1.6 | 16.7 | 63.0 | 0.2 | 0.04% | 606.9 |
| 6 | 1.0 | 10.1 | 49.7 | 0.4 | 0.07% | 490.0 |
| 7 | 2.2 | 12.4 | 48.2 | 1.1 | 0.19% | 459.1 |
| 8 | 2.4 | 10.5 | 37.7 | 2.3 | 0.39% | 352.2 |
| 9 | 1.1 | 5.6 | 20.2 | 2.9 | 0.48% | 190.0 |
| 10 | 1.3 | 36.9 | >100 | <0.1 | <0.1% | 1781.3 |
| 11 | 1.2 | 7.9 | 37.6 | 1.1 | 0.18% | 367.0 |
| 12 | 1.3 | 8.6 | 26.5 | 2.3 | 0.38% | 246.3 |
| 13 | 1.5 | 5.4 | 21.5 | 3.8 | 0.63% | 201.8 |
| 14 | 0.4 | 2.8 | 10.8 | 2.3 | 0.38% | 103.4 |
| 15 | 0.9 | 2.6 | 11.5 | 5.1 | 0.84% | 108.2 |
| 16 | 0.5 | 2.3 | 9.3 | 3.5 | 0.58% | 88.4 |
| 17 | 12.0 | 55.1 | >100 | <0.1 | <0.1% | 2167.0 |
| 18 | >20 | >100 | >100 | <0.1 | <0.1% | >4000 |
| 19 | 2.4 | 14.7 | 57.5 | 0.6 | 0.10% | 549.4 |

Example 4

Structure-Activity Relationship of the Apparent Affinity to Human Serum Proteins ($K_d^*$)

Figure 4:
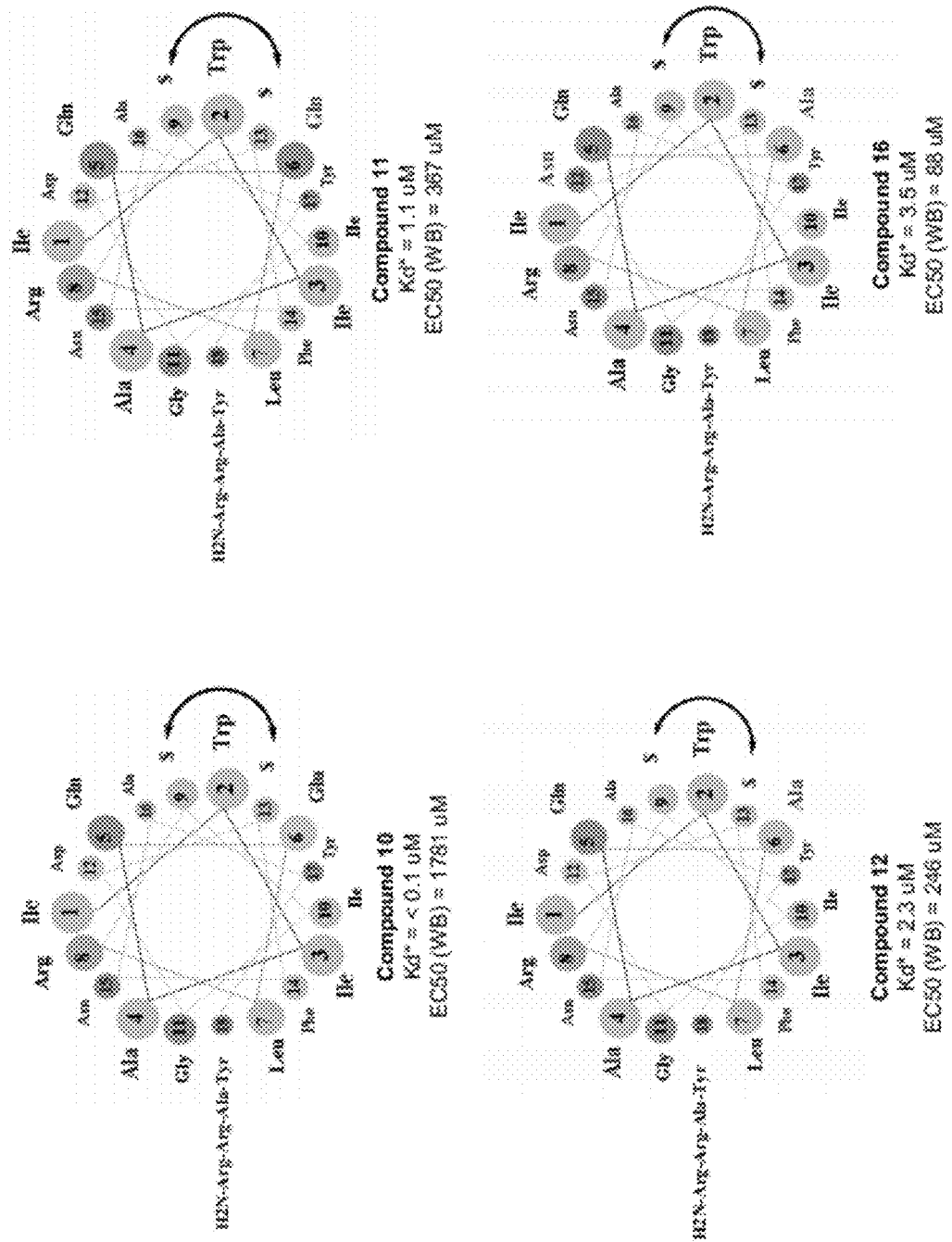
FIG. 4 shows helical wheel representations of improved peptidomimetic macrocycle analogs (SEQ ID NOS 116-118 and 122, respectively, in order of appearance).

FIG. 4 shows helical wheel representations of crosslinked peptide pairs of the invention in which one or more amino acids is altered to provide a crosslinked peptide analog with improved efficacy towards intracellular target(s) in whole cell assays. Across a number of sequences it is observed that a dipeptide motif consisting of an acidic (negatively charged) side chain adjacent to a large hydrophobic side chain yields higher affinity binding to human serum proteins such as albumin relative to an analog in which the acidic side chain has been replaced with a neutral side chain. In some cases replacement of both the acidic and large hydrophobic side chains with neutral and less hydrophobic side chains, respectively, provides lower affinity to human serum proteins. This structure activity relationship is consistent with the understanding that human serum proteins, and in particular human serum albumin, bind fatty acids under physiological conditions, and these fatty acids are recognized by a combined acidic/hydrophobic binding motif. It is also known that the membranes of human and animal cells consist of phospholipids and that the phosphate head groups of the lipid bilayer present a negatively charged surface at the outer membrane that will electrostatically repulse acidic (negatively charged) side chains of a peptide, and thus the replacement of an acidic side chain with a neutral side chain should increase the association of a crosslinked peptide with the cell membrane. This association with the outer membrane is the proposed required first step in the endocytosis of the crosslinked peptides of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of screening for an enhanced alpha-helical polypeptide with enhanced cellular efficacy in human whole blood, the enhanced alpha-helical polypeptide comprising a cross-linker connecting a first amino acid and a second amino acid of the polypeptide, the method comprising:

(a) providing a sequence of a parent alpha-helical polypeptide comprising a cross-linker connecting a first amino acid and a second amino acid of the parent polypeptide sequence, (b) producing a modified alpha-helical polypeptide having the same sequence as the parent polypeptide sequence except that at least one amino acid side chain that is not essential for target binding is different in comparison to the alpha-helical parent polypeptide sequence, wherein the modified alpha-helical polypeptide comprises a cross-linker connecting a first amino acid and a second amino acid of the modified alpha-helical polypeptide;

(c) measuring an in vitro activity ($EC_{50}$) of the modified alpha-helical polypeptide mediated by binding the alpha-helical polypeptide to an intracellular target, in the presence and/or absence of human serum;

(d) determining an apparent affinity ($K_d^*$) of the modified alpha-helical polypeptide for human serum proteins; and (e) selecting the modified alpha-helical polypeptide as an enhanced alpha-helical polypeptide if the alpha-helical polypeptide has a higher $K_d^*$ and an equal or lower $EC_{50}$ than the parent alpha-helical polypeptide.

2. The method of claim 1, further comprising selecting the modified alpha-helical polypeptide as an enhanced alpha-helical polypeptide, if the modified alpha-helical polypeptide has a $K_d^*$ from 1 to 700 micromolar.

3. The method of claim 1, wherein the enhanced alpha-helical polypeptide has a $K_d^*$ of less than 70 micromolar.

4. The method of claim 1, wherein the enhanced alpha-helical polypeptide has a $K_d^*$ of about 1-10 micromolar.

5. The method of claim 1, wherein the enhanced alpha-helical polypeptide possesses an estimated free fraction in human blood of about 0.1-50%, wherein the estimated free fraction is defined by the equation $$FreeFraction = \frac{K_d^*}{K_d^* + [HSA]_{total}}$$

and $[HSA]_{total}$ is 700 micromolar.

6. The method of claim 5, wherein the enhanced alpha-helical polypeptide possesses an estimated free fraction in human blood of about 0.5-10%.

7. The method of claim 1, further comprising determining if the enhanced alpha-helical polypeptide penetrates cell membranes.

8. The method of claim 1, wherein at least one of the first and second amino acids is an α,α-disubstituted amino acid.

9. The method of claim 1, wherein both the first and second amino acids are α,α-disubstituted.

10. The method of claim 1, wherein the first amino acid and the second amino acid are separated by two, three or six amino acids.

11. The method of claim 1, wherein the cross-linker spans 1 or 2 turns of the alpha helix.

12. The method of claim 1, wherein the length of the cross-linker is about 5 Å to about 9 Å per turn of the alpha-helix.

13. The method of claim 1, wherein the enhanced alpha-helical polypeptide carries a net positive charge at pH 7.4.

14. The method of claim 1, further comprising selecting the modified alpha-helical polypeptide as the enhanced alpha-helical polypeptide if the modified alpha-helical polypeptide provides a therapeutic effect.

15. The method of claim 1, further comprising selecting the modified alpha-helical polypeptide as the enhanced alpha-helical polypeptide if the modified alpha-helical polypeptide possesses an apparent affinity to human serum proteins of about 3 micromolar or weaker.

16. The method of claim 1, further comprising selecting the modified alpha-helical polypeptide as the enhanced alpha-helical polypeptide if the modified alpha-helical polypeptide possesses an apparent affinity to human serum proteins of about 10 micromolar or weaker.

17. The method of claim 1, further comprising selecting the modified alpha-helical polypeptide as the enhanced alpha-helical polypeptide if the modified alpha-helical polypeptide possesses an improved ability to penetrate cell membranes by an energy-dependent process relative to a corresponding uncrosslinked alpha-helical polypeptide.

18. The method of claim 1, wherein the parent polypeptide sequence comprises a dipeptide motif consisting of an acidic side chain adjacent to a large hydrophobic side chain.

19. The method of claim 1, wherein $K_d^*$ is defined by the equation $$EC'_{50} = EC_{50} + P\left(\frac{n}{1 + \frac{K_d^*}{EC_{50}}}\right)$$

where n is 1, and $EC_{50}$ is an in vitro efficacy measured in a whole cell assay in the absence of any human serum, and $EC'_{50}$ is an in vitro efficacy measured in a whole cell assay in N % human serum wherein P equals (N/100)×(700) micromolar.

20. The method of claim 1, wherein the amino acid side chain that is not essential for target binding in the parent alpha-helical polypeptide sequence is an acidic side chain, and the acidic side chain is replaced with a neutral side chain in the modified alpha-helical polypeptide.

21. The method of claim 1, wherein the parent alpha-helical polypeptide has Formula (I):

Formula I

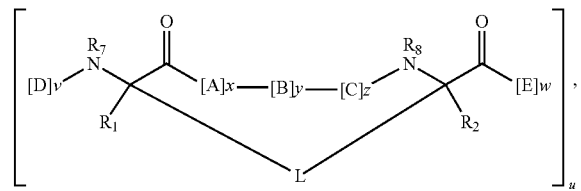

wherein:

each A, C, D, and E is independently a natural or non-natural amino acid;

B is a natural or non-natural amino acid, amino acid analog,

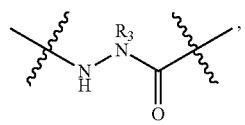

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, each of which except hydrogen is optionally substituted with $R_5$;

L is a macrocycle-forming linker of the formula -$L_1$-$L_2$-;

$L_1$ and $L_2$ and $L_3$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, $-OR_6$, $-N(R_6)_2$, $-SR_6$, $-SOR_6$, $-SO_2R_6$, $-CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, each of which except —H is optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, each of which except —H is optionally substituted with $R_5$, or part of a cyclic structure with an E residue;

u is an integer from 1 to 10;
v is an integer from 1-1000;
w is an integer from 1-1000;
x is an integer from 0-10;
y is an integer from 0-10;
z is an integer from 0-10; and
n is an integer from 1-5.

22. The method of claim 18, wherein producing a modified alpha-helical polypeptide comprises replacing the acidic side chain in the dipeptide motif with a neutral side chain.

23. The method of claim 18, wherein producing a modified alpha-helical polypeptide comprises replacing the large hydrophobic side chain in the dipeptide motif with a less hydrophobic side chain.

24. The method of claim 7, further comprising determining if the enhanced alpha-helical polypeptide penetrates cell membranes by an energy dependent process.

25. The method of claim 1, wherein measuring an in vitro activity ($EC_{50}$) of the modified alpha-helical polypeptide comprises using a cellular assay.

26. An enhanced alpha-helical polypeptide comprising a cross-linker connecting a first amino acid and a second amino acid of the enhanced alpha-helical polypeptide, wherein the enhanced alpha-helical polypeptide penetrates cell membranes by an energy-dependent process and binds to an intracellular target, wherein the enhanced alpha-helical polypeptide is selected according to the method of claim 1.

27. The enhanced alpha-helical polypeptide of claim 26, wherein penetration of cell membranes by the enhanced alpha-helical polypeptide is measured by incubating cells with a fluorescently labeled cross-linked polypeptide and measuring cellular fluorescence.

28. The enhanced alpha-helical polypeptide of claim 26, wherein the enhanced alpha-helical polypeptide has Formula (I):

Formula I

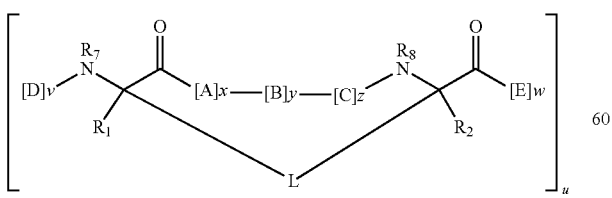

wherein:

each A, C, D, and E is independently a natural or non-natural amino acid;

B is a natural or non-natural amino acid, amino acid analog,

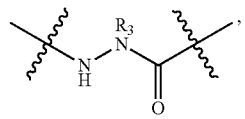

$[-NH-L_3-CO-]$, $[-NH-L_3-SO_2-]$, or $[-NH-L_3-]$;

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, each of which except hydrogen is optionally substituted with $R_5$;

L is a macrocycle-forming linker of the formula $-L_1-L_2-$;

$L_1$ and $L_2$, and $L_3$ are independently alkylene, alkenylene, alkynylene, heteroalkylene, cycloalkylene, heterocycloalkylene, cycloarylene, heterocycloarylene, or $[-R_4-K-R_4-]_n$, each being optionally substituted with $R_5$.

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, $-OR_6$, $-N(R_6)_2$, $-SR_6$, $-SOR_6$, $-SO_2R_6$, $-CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, each of which except —H is optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, each of which except —H is optionally substituted with $R_5$, or part of a cyclic structure with an E residue;

u is an integer from 1 to 10
v is an integer from 1-1000;
w is an integer from 1-1000;
x is an integer from 0-10;
y is an integer from 0-10;
z is an integer from 0-10; and
n is an integer from 1-5.

\* \* \* \* \*

UNITED STATES PATENT AND TRADEMARK OFFICE
CERTIFICATE OF CORRECTION

PATENT NO. : 8,399,405 B2
APPLICATION NO. : 13/366113
DATED : March 19, 2013
INVENTOR(S) : Huw M. Nash et al.

It is certified that error appears in the above-identified patent and that said Letters Patent is hereby corrected as shown below:

In the claims at column 178, line 66, please replace "in vitro" with -- *in vitro* --;
In the claims at column 179, lines 3, 9, 14, 16, and 18, please replace "$K_d$*" with -- $K_d$* --;
In the claims at column 179, line 29, please replace "*total*" with -- total --;
In the claims at column 180, line 6, please replace "$K_d$*" with -- $K_d$* --;
In the claims at column 180, line 11, please replace "$K$*$_d$" with -- $K_d$* --;
In the claims at column 180, line 18, please replace "N %" with -- N% --;
In the claims at column 182, line 54, please replace "1 to 10" with -- 1 to 10; --.

Signed and Sealed this
Twenty-ninth Day of October, 2013

Teresa Stanek Rea
*Deputy Director of the United States Patent and Trademark Office*

SEQUENCE LISTING

```
<160> NUMBER OF SEQ ID NOS: 125

<210> SEQ ID NO 1
<211> LENGTH: 19
<212> TYPE: PRT
<213> ORGANISM: Homo sapiens

<400> SEQUENCE: 1

Pro Leu Ser Gln Glu Thr Phe Ser Asp Leu Trp Lys Leu Leu Pro Glu
1               5                   10                  15

Asn Asn Val

<210> SEQ ID NO 2
<211> LENGTH: 25
<212> TYPE: PRT
<213> ORGANISM: Homo sapiens

<400> SEQUENCE: 2

Gln Glu Asp Ile Ile Arg Asn Ile Ala Arg His Leu Ala Gln Val Gly
1               5                   10                  15

Asp Ser Met Asp Arg Ser Ile Pro Pro
            20                  25

<210> SEQ ID NO 3
<211> LENGTH: 25
<212> TYPE: PRT
<213> ORGANISM: Homo sapiens

<400> SEQUENCE: 3

Asp Asn Arg Pro Glu Ile Trp Ile Ala Gln Glu Leu Arg Arg Ile Gly
1               5                   10                  15

Asp Glu Phe Asn Ala Tyr Tyr Ala Arg
            20                  25

<210> SEQ ID NO 4
<211> LENGTH: 25
<212> TYPE: PRT
<213> ORGANISM: Homo sapiens
```

-continued

<400> SEQUENCE: 4

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 5
<211> LENGTH: 25
<212> TYPE: PRT
<213> ORGANISM: Homo sapiens

<400> SEQUENCE: 5

Glu Glu Gln Trp Ala Arg Glu Ile Gly Ala Gln Leu Arg Arg Met Ala
1               5                   10                  15

Asp Asp Leu Asn Ala Gln Tyr Glu Arg
            20                  25

<210> SEQ ID NO 6
<211> LENGTH: 24
<212> TYPE: PRT
<213> ORGANISM: Homo sapiens

<400> SEQUENCE: 6

Arg Ser Ser Ala Ala Gln Leu Thr Ala Ala Arg Leu Lys Ala Leu Gly
1               5                   10                  15

Asp Glu Leu His Gln Arg Thr Met
            20

<210> SEQ ID NO 7
<211> LENGTH: 22
<212> TYPE: PRT
<213> ORGANISM: Homo sapiens

<400> SEQUENCE: 7

Ala Glu Leu Pro Pro Glu Phe Ala Ala Gln Leu Arg Lys Ile Gly Asp
1               5                   10                  15

Lys Val Tyr Cys Thr Trp
            20

<210> SEQ ID NO 8
<211> LENGTH: 25
<212> TYPE: PRT
<213> ORGANISM: Homo sapiens

<400> SEQUENCE: 8

Val Pro Ala Asp Leu Lys Asp Glu Cys Ala Gln Leu Arg Arg Ile Gly
1               5                   10                  15

Asp Lys Val Asn Leu Arg Gln Lys Leu
            20                  25

<210> SEQ ID NO 9
<211> LENGTH: 24
<212> TYPE: PRT
<213> ORGANISM: Homo sapiens

<400> SEQUENCE: 9

Gln His Arg Ala Glu Val Gln Ile Ala Arg Lys Leu Gln Cys Ile Ala
1               5                   10                  15

Asp Gln Phe His Arg Leu His Thr
            20

<210> SEQ ID NO 10

```
<211> LENGTH: 22
<212> TYPE: PRT
<213> ORGANISM: Homo sapiens

<400> SEQUENCE: 10

Ser Ser Ala Ala Gln Leu Thr Ala Ala Arg Leu Lys Ala Leu Gly Asp
1               5                   10                  15

Glu Leu His Gln Arg Thr
            20

<210> SEQ ID NO 11
<211> LENGTH: 25
<212> TYPE: PRT
<213> ORGANISM: Homo sapiens

<400> SEQUENCE: 11

Cys Met Glu Gly Ser Asp Ala Leu Ala Leu Arg Leu Ala Cys Ile Gly
1               5                   10                  15

Asp Glu Met Asp Val Ser Leu Arg Ala
            20                  25

<210> SEQ ID NO 12
<211> LENGTH: 24
<212> TYPE: PRT
<213> ORGANISM: Homo sapiens

<400> SEQUENCE: 12

Asp Ile Glu Arg Arg Lys Glu Val Glu Ser Ile Leu Lys Lys Asn Ser
1               5                   10                  15

Asp Trp Ile Trp Asp Trp Ser Ser
            20

<210> SEQ ID NO 13
<211> LENGTH: 22
<212> TYPE: PRT
<213> ORGANISM: Homo sapiens

<400> SEQUENCE: 13

Gly Arg Leu Ala Glu Val Cys Ala Val Leu Leu Arg Leu Gly Asp Glu
1               5                   10                  15

Leu Glu Met Ile Arg Pro
            20

<210> SEQ ID NO 14
<211> LENGTH: 25
<212> TYPE: PRT
<213> ORGANISM: Homo sapiens

<400> SEQUENCE: 14

Pro Gln Asp Ala Ser Thr Lys Lys Ser Glu Cys Leu Lys Arg Ile Gly
1               5                   10                  15

Asp Glu Leu Asp Ser Asn Met Glu Leu
            20                  25

<210> SEQ ID NO 15
<211> LENGTH: 22
<212> TYPE: PRT
<213> ORGANISM: Homo sapiens

<400> SEQUENCE: 15

Pro Ser Ser Thr Met Gly Gln Val Gly Arg Gln Leu Ala Ile Ile Gly
1               5                   10                  15

Asp Asp Ile Asn Arg Arg
```

```
                        20

<210> SEQ ID NO 16
<211> LENGTH: 14
<212> TYPE: PRT
<213> ORGANISM: Homo sapiens

<400> SEQUENCE: 16

Lys Gln Ala Leu Arg Glu Ala Gly Asp Glu Phe Glu Leu Arg
1               5                   10

<210> SEQ ID NO 17
<211> LENGTH: 22
<212> TYPE: PRT
<213> ORGANISM: Homo sapiens

<400> SEQUENCE: 17

Leu Ser Pro Pro Val Val His Leu Ala Leu Ala Leu Arg Gln Ala Gly
1               5                   10                  15

Asp Asp Phe Ser Arg Arg
            20

<210> SEQ ID NO 18
<211> LENGTH: 23
<212> TYPE: PRT
<213> ORGANISM: Homo sapiens

<400> SEQUENCE: 18

Glu Val Ile Pro Met Ala Ala Val Lys Gln Ala Leu Arg Glu Ala Gly
1               5                   10                  15

Asp Glu Phe Glu Leu Arg Tyr
            20

<210> SEQ ID NO 19
<211> LENGTH: 20
<212> TYPE: PRT
<213> ORGANISM: Homo sapiens

<400> SEQUENCE: 19

Pro Ala Asp Pro Leu His Gln Ala Met Arg Ala Ala Gly Asp Glu Phe
1               5                   10                  15

Glu Thr Arg Phe
            20

<210> SEQ ID NO 20
<211> LENGTH: 23
<212> TYPE: PRT
<213> ORGANISM: Homo sapiens

<400> SEQUENCE: 20

Ala Thr Ser Arg Lys Leu Glu Thr Leu Arg Arg Val Gly Asp Gly Val
1               5                   10                  15

Gln Arg Asn His Glu Thr Ala
            20

<210> SEQ ID NO 21
<211> LENGTH: 19
<212> TYPE: PRT
<213> ORGANISM: Homo sapiens

<400> SEQUENCE: 21

Leu Ala Glu Val Cys Thr Val Leu Leu Arg Leu Gly Asp Glu Leu Glu
1               5                   10                  15
```

```
Gln Ile Arg

<210> SEQ ID NO 22
<211> LENGTH: 19
<212> TYPE: PRT
<213> ORGANISM: Homo sapiens

<400> SEQUENCE: 22

Met Thr Val Gly Glu Leu Ser Arg Ala Leu Gly His Glu Asn Gly Ser
1               5                   10                  15

Leu Asp Pro

<210> SEQ ID NO 23
<211> LENGTH: 22
<212> TYPE: PRT
<213> ORGANISM: Homo sapiens

<400> SEQUENCE: 23

Val Val Glu Gly Glu Lys Glu Val Glu Ala Leu Lys Lys Ser Ala Asp
1               5                   10                  15

Trp Val Ser Asp Trp Ser
            20

<210> SEQ ID NO 24
<211> LENGTH: 20
<212> TYPE: PRT
<213> ORGANISM: Homo sapiens

<400> SEQUENCE: 24

Ser Met Ala Arg Asp Pro Gln Arg Tyr Leu Val Ile Gln Gly Asp Asp
1               5                   10                  15

Arg Met Lys Leu
            20

<210> SEQ ID NO 25
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 25

Gln Glu Asp Ile Ile Arg Asn Ile Ala Arg His Leu Ala Xaa Val Gly
1               5                   10                  15

Asp Xaa Met Asp Arg Ser Ile Pro Pro
            20                  25

<210> SEQ ID NO 26
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
```

```
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 26

Asp Asn Arg Pro Glu Ile Trp Ile Ala Gln Glu Leu Arg Xaa Ile Gly
1               5                   10                  15

Asp Xaa Phe Asn Ala Tyr Tyr Ala Arg
            20                  25

<210> SEQ ID NO 27
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 27

Asn Leu Trp Ala Ala Gln Arg Tyr Gly Arg Glu Leu Arg Xaa Met Ser
1               5                   10                  15

Asp Xaa Phe Val Asp Ser Phe Lys Lys
            20                  25

<210> SEQ ID NO 28
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 28

Glu Glu Gln Trp Ala Arg Glu Ile Gly Ala Gln Leu Arg Xaa Met Ala
1               5                   10                  15

Asp Xaa Leu Asn Ala Gln Tyr Glu Arg
            20                  25

<210> SEQ ID NO 29
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
```

```
<220> FEATURE:
<221> NAME/KEY: MOD_RES
<222> LOCATION: (18)..(18)
<223> OTHER INFORMATION: Any amino acid available for cross linking

<400> SEQUENCE: 29

Arg Ser Ser Ala Ala Gln Leu Thr Ala Ala Arg Leu Lys Xaa Leu Gly
1               5                   10                  15

Asp Xaa Leu His Gln Arg Thr Met
            20

<210> SEQ ID NO 30
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: misc_feature
<222> LOCATION: (13)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any amino acid available for cross linking

<400> SEQUENCE: 30

Ala Glu Leu Pro Pro Glu Phe Ala Ala Gln Leu Arg Xaa Ile Gly Asp
1               5                   10                  15

Xaa Val Tyr Cys Thr Trp
            20

<210> SEQ ID NO 31
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 31

Val Pro Ala Asp Leu Lys Asp Glu Cys Ala Gln Leu Arg Xaa Ile Gly
1               5                   10                  15

Asp Xaa Val Asn Leu Arg Gln Lys Leu
            20                  25

<210> SEQ ID NO 32
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
```

```
<222> LOCATION: (18)..(18)
<223> OTHER INFORMATION: Any amino acid available for cross linking

<400> SEQUENCE: 32

Gln His Arg Ala Glu Val Gln Ile Ala Arg Lys Leu Gln Xaa Ile Ala
1               5                   10                  15

Asp Xaa Phe His Arg Leu His Thr
            20

<210> SEQ ID NO 33
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: misc_feature
<222> LOCATION: (13)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any amino acid available for cross linking

<400> SEQUENCE: 33

Ser Ser Ala Ala Gln Leu Thr Ala Ala Arg Leu Lys Xaa Leu Gly Asp
1               5                   10                  15

Xaa Leu His Gln Arg Thr
            20

<210> SEQ ID NO 34
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 34

Cys Met Glu Gly Ser Asp Ala Leu Ala Leu Arg Leu Ala Xaa Ile Gly
1               5                   10                  15

Asp Xaa Met Asp Val Ser Leu Arg Ala
            20                  25

<210> SEQ ID NO 35
<211> LENGTH: 24
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking
```

<400> SEQUENCE: 35

Asp Ile Glu Arg Arg Lys Glu Val Glu Ser Ile Leu Lys Xaa Asn Ser
1               5                   10                  15

Asp Xaa Ile Trp Asp Trp Ser Ser
            20

<210> SEQ ID NO 36
<211> LENGTH: 22
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking

<400> SEQUENCE: 36

Gly Arg Leu Ala Glu Val Cys Ala Val Leu Leu Xaa Leu Gly Asp Xaa
1               5                   10                  15

Leu Glu Met Ile Arg Pro
            20

<210> SEQ ID NO 37
<211> LENGTH: 25
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 37

Pro Gln Asp Ala Ser Thr Lys Lys Ser Glu Cys Leu Lys Xaa Ile Gly
1               5                   10                  15

Asp Xaa Leu Asp Ser Asn Met Glu Leu
            20                  25

<210> SEQ ID NO 38
<211> LENGTH: 22
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 38

```
Pro Ser Ser Thr Met Gly Gln Val Gly Arg Gln Leu Ala Xaa Ile Gly
1               5                   10                  15

Asp Xaa Ile Asn Arg Arg
            20

<210> SEQ ID NO 39
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid available for cross linking
<220> FEATURE:
<221> NAME/KEY: misc_feature
<222> LOCATION: (6)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid available for cross linking

<400> SEQUENCE: 39

Lys Gln Ala Leu Arg Xaa Ala Gly Asp Xaa Phe Glu Leu Arg
1               5                   10

<210> SEQ ID NO 40
<211> LENGTH: 22
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 40

Leu Ser Pro Pro Val Val His Leu Ala Leu Ala Leu Arg Xaa Ala Gly
1               5                   10                  15

Asp Xaa Phe Ser Arg Arg
            20

<210> SEQ ID NO 41
<211> LENGTH: 23
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Any amino acid available for cross linking
<220> FEATURE:
<221> NAME/KEY: misc_feature
<222> LOCATION: (14)..(18)
<223> OTHER INFORMATION: Crosslink between residues
<220> FEATURE:
<221> NAME/KEY: MOD_RES
<222> LOCATION: (18)..(18)
<223> OTHER INFORMATION: Any amino acid available for cross linking

<400> SEQUENCE: 41

Glu Val Ile Pro Met Ala Ala Val Lys Gln Ala Leu Arg Xaa Ala Gly
1               5                   10                  15

Asp Xaa Phe Glu Leu Arg Tyr
```

```
<210> SEQ ID NO 42
<211> LENGTH: 20
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Any amino acid available for cross linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross linking

<400> SEQUENCE: 42

Pro Ala Asp Pro Leu His Gln Ala Met Arg Xaa Ala Gly Asp Xaa Phe
1               5                   10                  15

Glu Thr Arg Phe
            20

<210> SEQ ID NO 43
<211> LENGTH: 23
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Any amino acid available for cross linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross linking

<400> SEQUENCE: 43

Ala Thr Ser Arg Lys Leu Glu Thr Leu Arg Xaa Val Gly Asp Xaa Val
1               5                   10                  15

Gln Arg Asn His Glu Thr Ala
            20

<210> SEQ ID NO 44
<211> LENGTH: 19
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Any amino acid available for cross linking
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any amino acid available for cross linking

<400> SEQUENCE: 44

Leu Ala Glu Val Cys Thr Val Leu Leu Xaa Leu Gly Asp Xaa Leu Glu
1               5                   10                  15

Gln Ile Arg
```

-continued

```
<210> SEQ ID NO 45
<211> LENGTH: 19
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking

<400> SEQUENCE: 45

Met Thr Val Gly Glu Leu Ser Arg Ala Leu Gly Xaa Glu Asn Gly Xaa
1               5                   10                  15

Leu Asp Pro

<210> SEQ ID NO 46
<211> LENGTH: 22
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: misc_feature
<222> LOCATION: (13)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any amino acid available for cross linking

<400> SEQUENCE: 46

Val Val Glu Gly Glu Lys Glu Val Glu Ala Leu Lys Xaa Ser Ala Asp
1               5                   10                  15

Xaa Val Ser Asp Trp Ser
            20

<210> SEQ ID NO 47
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking

<400> SEQUENCE: 47

Ser Met Ala Arg Asp Pro Gln Arg Tyr Leu Val Xaa Gln Gly Asp Xaa
1               5                   10                  15

Arg Met Lys Leu
            20

<210> SEQ ID NO 48
<211> LENGTH: 25
<212> TYPE: PRT
```

```
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 48

Gln Glu Asp Ile Ile Arg Asn Ile Xaa Arg His Leu Xaa Gln Val Gly
1               5                   10                  15

Asp Ser Met Asp Arg Ser Ile Pro Pro
            20                  25

<210> SEQ ID NO 49
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 49

Asp Asn Arg Pro Glu Ile Trp Ile Xaa Gln Glu Leu Xaa Arg Ile Gly
1               5                   10                  15

Asp Glu Phe Asn Ala Tyr Tyr Ala Arg
            20                  25

<210> SEQ ID NO 50
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 50

Asn Leu Trp Ala Ala Gln Arg Tyr Xaa Arg Glu Leu Xaa Arg Met Ser
1               5                   10                  15

Asp Glu Phe Val Asp Ser Phe Lys Lys
            20                  25

<210> SEQ ID NO 51
<211> LENGTH: 25
<212> TYPE: PRT
<213> ORGANISM: Homo sapiens
<220> FEATURE:
```

```
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 51

Glu Glu Gln Trp Ala Arg Glu Ile Xaa Ala Gln Leu Xaa Arg Met Ala
1               5                  10                  15

Asp Asp Leu Asn Ala Gln Tyr Glu Arg
            20                  25

<210> SEQ ID NO 52
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 52

Arg Ser Ser Ala Ala Gln Leu Thr Xaa Ala Arg Leu Xaa Ala Leu Gly
1               5                  10                  15

Asp Glu Leu His Gln Arg Thr Met
            20

<210> SEQ ID NO 53
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Any amino acid available for cross linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking

<400> SEQUENCE: 53

Ala Glu Leu Pro Pro Glu Phe Xaa Ala Gln Leu Xaa Lys Ile Gly Asp
1               5                  10                  15

Lys Val Tyr Cys Thr Trp
            20

<210> SEQ ID NO 54
<211> LENGTH: 25
<212> TYPE: PRT
<213> ORGANISM: Homo sapiens
<220> FEATURE:
<221> NAME/KEY: MOD_RES
<222> LOCATION: (9)..(9)
```

-continued

```
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 54

Val Pro Ala Asp Leu Lys Asp Glu Xaa Ala Gln Leu Xaa Arg Ile Gly
1               5                   10                  15

Asp Lys Val Asn Leu Arg Gln Lys Leu
            20                  25

<210> SEQ ID NO 55
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 55

Gln His Arg Ala Glu Val Gln Ile Xaa Arg Lys Leu Xaa Cys Ile Ala
1               5                   10                  15

Asp Gln Phe His Arg Leu His Thr
            20

<210> SEQ ID NO 56
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Any amino acid available for cross linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking

<400> SEQUENCE: 56

Ser Ser Ala Ala Gln Leu Thr Xaa Ala Arg Leu Xaa Ala Leu Gly Asp
1               5                   10                  15

Glu Leu His Gln Arg Thr
            20

<210> SEQ ID NO 57
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
```

```
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 57

Cys Met Glu Gly Ser Asp Ala Leu Xaa Leu Arg Leu Xaa Cys Ile Gly
1               5                   10                  15

Asp Glu Met Asp Val Ser Leu Arg Ala
            20                  25

<210> SEQ ID NO 58
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 58

Asp Ile Glu Arg Arg Lys Glu Val Xaa Ser Ile Leu Xaa Lys Asn Ser
1               5                   10                  15

Asp Trp Ile Trp Asp Trp Ser Ser
            20

<210> SEQ ID NO 59
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 59

Gly Arg Leu Ala Glu Val Xaa Ala Val Leu Xaa Arg Leu Gly Asp Glu
1               5                   10                  15

Leu Glu Met Ile Arg Pro
            20

<210> SEQ ID NO 60
<211> LENGTH: 25
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
```

```
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 60

Pro Gln Asp Ala Ser Thr Lys Lys Xaa Glu Cys Leu Xaa Arg Ile Gly
1               5                   10                  15

Asp Glu Leu Asp Ser Asn Met Glu Leu
            20                  25

<210> SEQ ID NO 61
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 61

Pro Ser Ser Thr Met Gly Gln Val Xaa Arg Gln Leu Xaa Ile Ile Gly
1               5                   10                  15

Asp Asp Ile Asn Arg Arg
            20

<210> SEQ ID NO 62
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid available for cross linking
<220> FEATURE:
<221> NAME/KEY: misc_feature
<222> LOCATION: (1)..(5)
<223> OTHER INFORMATION: Crosslink between residues
<220> FEATURE:
<221> NAME/KEY: MOD_RES
<222> LOCATION: (5)..(5)
<223> OTHER INFORMATION: Any amino acid available for cross linking

<400> SEQUENCE: 62

Xaa Gln Ala Leu Xaa Glu Ala Gly Asp Glu Phe Glu Leu Arg
1               5                   10

<210> SEQ ID NO 63
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
```

<400> SEQUENCE: 63

Leu Ser Pro Pro Val Val His Leu Xaa Leu Ala Leu Xaa Gln Ala Gly
1               5                   10                  15

Asp Asp Phe Ser Arg Arg
            20

<210> SEQ ID NO 64
<211> LENGTH: 23
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking

<400> SEQUENCE: 64

Glu Val Ile Pro Met Ala Ala Val Xaa Gln Ala Leu Xaa Glu Ala Gly
1               5                   10                  15

Asp Glu Phe Glu Leu Arg Tyr
            20

<210> SEQ ID NO 65
<211> LENGTH: 20
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid available for cross linking
<220> FEATURE:
<221> NAME/KEY: misc_feature
<222> LOCATION: (6)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid available for cross linking

<400> SEQUENCE: 65

Pro Ala Asp Pro Leu Xaa Gln Ala Met Xaa Ala Ala Gly Asp Glu Phe
1               5                   10                  15

Glu Thr Arg Phe
            20

<210> SEQ ID NO 66
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid available for cross linking
<220> FEATURE:
<221> NAME/KEY: misc_feature
<222> LOCATION: (6)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid available for cross linking

<400> SEQUENCE: 66

Ala Thr Ser Arg Lys Xaa Glu Thr Leu Xaa Arg Val Gly Asp Gly Val
1               5                   10                  15

Gln Arg Asn His Glu Thr Ala
            20

<210> SEQ ID NO 67
<211> LENGTH: 19
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Any amino acid available for cross linking
<220> FEATURE:
<221> NAME/KEY: misc_feature
<222> LOCATION: (5)..(9)
<223> OTHER INFORMATION: Crosslink between residues
<220> FEATURE:
<221> NAME/KEY: MOD_RES
<222> LOCATION: (9)..(9)
<223> OTHER INFORMATION: Any amino acid available for cross linking

<400> SEQUENCE: 67

Leu Ala Glu Val Xaa Thr Val Leu Xaa Arg Leu Gly Asp Glu Leu Glu
1               5                   10                  15

Gln Ile Arg

<210> SEQ ID NO 68
<211> LENGTH: 19
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 68

Met Thr Val Gly Glu Leu Xaa Arg Ala Leu Xaa His Glu Asn Gly Ser
1               5                   10                  15

Leu Asp Pro

<210> SEQ ID NO 69
<211> LENGTH: 22
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Any amino acid available for cross linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking

<400> SEQUENCE: 69

Val Val Glu Gly Glu Lys Glu Xaa Glu Ala Leu Xaa Lys Ser Ala Asp
1               5                   10                  15

Trp Val Ser Asp Trp Ser
            20

<210> SEQ ID NO 70
<211> LENGTH: 20
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 70

Ser Met Ala Arg Asp Pro Xaa Arg Tyr Leu Xaa Ile Gln Gly Asp Asp
1               5                   10                  15

Arg Met Lys Leu
            20

<210> SEQ ID NO 71
<211> LENGTH: 16
<212> TYPE: PRT
<213> ORGANISM: Homo sapiens

<400> SEQUENCE: 71

Leu Ser Gln Glu Thr Phe Ser Asp Leu Trp Lys Leu Leu Pro Glu Asn
1               5                   10                  15

<210> SEQ ID NO 72
<211> LENGTH: 16
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking

<400> SEQUENCE: 72

Leu Ser Gln Glu Thr Phe Ser Asp Xaa Trp Lys Leu Leu Pro Glu Xaa
1               5                   10                  15

<210> SEQ ID NO 73
<211> LENGTH: 16
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Any amino acid available for cross linking
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking

```
<400> SEQUENCE: 73

Leu Ser Gln Glu Xaa Phe Ser Asp Leu Trp Lys Xaa Leu Pro Glu Asn
1               5                   10                  15

<210> SEQ ID NO 74
<211> LENGTH: 16
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Any amino acid available for cross linking
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 74

Leu Ser Gln Xaa Thr Phe Ser Asp Leu Trp Xaa Leu Leu Pro Glu Asn
1               5                   10                  15

<210> SEQ ID NO 75
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any amino acid available for cross linking

<400> SEQUENCE: 75

Leu Ser Gln Glu Thr Phe Xaa Asp Leu Trp Lys Leu Leu Xaa Glu Asn
1               5                   10                  15

<210> SEQ ID NO 76
<211> LENGTH: 16
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any amino acid available for cross linking

<400> SEQUENCE: 76

Gln Ser Gln Gln Thr Phe Xaa Asn Leu Trp Arg Leu Leu Xaa Gln Asn
1               5                   10                  15

<210> SEQ ID NO 77
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 77

Asp Arg Val Tyr Ile His Pro Phe
1               5

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Gln Arg Leu Gly Asn Gln Trp Ala Val Gly His Leu Met
1               5                   10

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Pro Pro Gly Phe Ser Pro Phe Arg
1               5

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Ser His Lys Asp Met Gln Leu Gly Arg
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Arg Ala Ser His Leu Gly Leu Ala Arg
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Tyr Ser Met Glu His Phe Arg Trp Gly Lys Pro Val
1               5                   10
```

```
<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid available for cross linking
<220> FEATURE:
<221> NAME/KEY: misc_feature
<222> LOCATION: (3)..(5)
<223> OTHER INFORMATION: Crosslink between residues
<220> FEATURE:
<221> NAME/KEY: MOD_RES
<222> LOCATION: (5)..(5)
<223> OTHER INFORMATION: Any amino acid available for cross linking

<400> SEQUENCE: 83

Asp Arg Xaa Tyr Xaa His Pro Phe
1               5

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any amino acid available for cross linking

<400> SEQUENCE: 84

Glu Gln Arg Leu Gly Asn Xaa Trp Ala Val Gly His Leu Xaa
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid available for cross linking
<220> FEATURE:
<221> NAME/KEY: misc_feature
<222> LOCATION: (4)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid available for cross linking

<400> SEQUENCE: 85

Arg Pro Pro Xaa Phe Ser Pro Phe Arg Xaa
1               5                   10

<210> SEQ ID NO 86
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 86

Ile Ser His Lys Asp Met Xaa Leu Gly Arg Xaa
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking

<400> SEQUENCE: 87

Ala Arg Ala Ser His Leu Xaa Leu Ala Arg Xaa
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid available for cross linking
<220> FEATURE:
<221> NAME/KEY: misc_feature
<222> LOCATION: (5)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any amino acid available for cross linking

<400> SEQUENCE: 88

Ser Tyr Ser Met Xaa His Phe Arg Trp Xaa Lys Pro Val
1               5                   10

<210> SEQ ID NO 89
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 89

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 90

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
```

```
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 91

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 92

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
```

```
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 93

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 94

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
```

```
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 95

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 96

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated
```

```
<400> SEQUENCE: 97

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 98

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 99

Asp Ile Ile Arg Asn Ile Ala Arg His Leu Ala Xaa Val Gly Asp Xaa
1               5                   10                  15

Xaa Asp Arg Ser Ile
```

20

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 100

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 101

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 102
<211> LENGTH: 21
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 102

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 103
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 103

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
```

```
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 104

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 105

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
```

```
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 106

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 107
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 107

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 108
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: MOD_RES
<222> LOCATION: (14)..(14)
<223> OTHER INFORMATION: Aib
<220> FEATURE:
<221> NAME/KEY: misc_feature
<222> LOCATION: (12)..(16)
<223> OTHER INFORMATION: Crosslink between residues
```

-continued

```
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 108

Asp Ala Ala Arg Asn Ile Ala Arg His Leu Ala Xaa Val Xaa Asp Xaa
1               5                   10                  15

Xaa Ala Arg Ser Ile
            20

<210> SEQ ID NO 109
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: MOD_RES
<222> LOCATION: (14)..(14)
<223> OTHER INFORMATION: Aib
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 109

Asp Ile Ala Arg Asn Ile Ala Arg His Leu Ala Xaa Val Xaa Asp Xaa
1               5                   10                  15

Xaa Ala Arg Ser Ile
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)..(12)
<223> OTHER INFORMATION: Any amino acid available for cross linking
<220> FEATURE:
<221> NAME/KEY: MOD_RES
<222> LOCATION: (14)..(14)
<223> OTHER INFORMATION: Aib
<220> FEATURE:
<221> NAME/KEY: misc_feature
```

```
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any amino acid available for cross linking
<220> FEATURE:
<221> NAME/KEY: MOD_RES
<222> LOCATION: (17)..(17)
<223> OTHER INFORMATION: Nle
<220> FEATURE:
<223> OTHER INFORMATION: C-term amidated

<400> SEQUENCE: 110

Asp Ala Ile Arg Asn Ile Ala Arg His Leu Ala Xaa Val Xaa Asp Xaa
1               5                   10                  15

Xaa Ala Arg Ser Ile
            20

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term proprionyl
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: MOD_RES
<222> LOCATION: (11)..(11)
<223> OTHER INFORMATION: Aib
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term amidated

<400> SEQUENCE: 111

Arg Asn Ile Ala Arg His Leu Ala Xaa Val Xaa Asp Xaa Xaa Asp Arg
1               5                   10                  15

Ser Ile

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term proprionyl
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (9)..(9)
<223> OTHER INFORMATION: Any amino acid available for cross linking
<220> FEATURE:
```

```
<221> NAME/KEY: MOD_RES
<222> LOCATION: (11)..(11)
<223> OTHER INFORMATION: Aib
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term amidated

<400> SEQUENCE: 112

Arg Asn Ile Ala Arg His Leu Xaa Xaa Val Xaa Asp Xaa Xaa Asp Arg
1               5                   10                  15

Ser Ile

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term proprionyl
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: MOD_RES
<222> LOCATION: (11)..(11)
<223> OTHER INFORMATION: Aib
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 113

Arg Asn Ile Ala Arg His Leu Ala Xaa Val Xaa Asp Xaa Phe Ala Arg
1               5                   10                  15

Ser Ile

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term proprionyl
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
```

```
<221> NAME/KEY: MOD_RES
<222> LOCATION: (13)..(13)
<223> OTHER INFORMATION: Any amino acid available for cross linking
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (15)..(15)
<223> OTHER INFORMATION: Aib
<220> FEATURE:
<223> OTHER INFORMATION: C-term amidated

<400> SEQUENCE: 114

Arg Asn Ile Ala Arg His Leu Ala Xaa Val Gly Asp Xaa Xaa Xaa Arg
1               5                   10                  15

Ser Ile

<210> SEQ ID NO 115
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term proprionyl
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: MOD_RES
<222> LOCATION: (11)..(11)
<223> OTHER INFORMATION: Aib
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 115

Arg Asn Ile Xaa Arg His Leu Xaa Xaa Val Xaa Asp Xaa Ala Ala Arg
1               5                   10                  15

Ser Ile

<210> SEQ ID NO 116
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
```

```
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 116

Ile Trp Ile Ala Gln Glu Leu Arg Xaa Ile Gly Asp Xaa Phe Asn Ala
1               5                   10                  15

Tyr Tyr Ala Arg Arg
            20

<210> SEQ ID NO 117
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 117

Ile Trp Ile Ala Gln Gln Leu Arg Xaa Ile Gly Asp Xaa Phe Asn Ala
1               5                   10                  15

Tyr Tyr Ala Arg Arg
            20

<210> SEQ ID NO 118
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 118

Ile Trp Ile Ala Gln Ala Leu Arg Xaa Ile Gly Asp Xaa Phe Asn Ala
1               5                   10                  15
```

Tyr Tyr Ala Arg Arg
            20

<210> SEQ ID NO 119
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 119

Arg Trp Ile Ala Gln Gln Leu Arg Xaa Ile Gly Asp Xaa Phe Asn Ala
1               5                   10                  15

Tyr Tyr Ala Arg Arg
            20

<210> SEQ ID NO 120
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 120

Arg Trp Ile Ala Gln Ala Leu Arg Xaa Ile Gly Asp Xaa Phe Asn Ala
1               5                   10                  15

Phe Tyr Ala Arg Arg
            20

<210> SEQ ID NO 121
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

```
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 121

Arg Trp Ile Ala Gln Ala Leu Arg Xaa Ile Gly Asn Xaa Phe Asn Ala
1               5                   10                  15

Tyr Tyr Ala Arg Arg
            20

<210> SEQ ID NO 122
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (9)..(9)
<223> OTHER INFORMATION: Any amino acid available for cross linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross linking
<220> FEATURE:
<223> OTHER INFORMATION: C-term amidated

<400> SEQUENCE: 122

Ile Trp Ile Ala Gln Ala Leu Arg Xaa Ile Gly Asn Xaa Phe Asn Ala
1               5                   10                  15

Tyr Tyr Ala Arg Arg
            20

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (8)..(8)
<223> OTHER INFORMATION: Any amino acid available for cross linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking
<220> FEATURE:
<223> OTHER INFORMATION: C-term amidated
```

```
<400> SEQUENCE: 123

Glu Arg Leu Arg Arg Arg Ile Xaa Leu Cys Arg Xaa His His Ser Thr
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (8)..(8)
<223> OTHER INFORMATION: Any amino acid available for cross linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross linking
<220> FEATURE:
<223> OTHER INFORMATION: C-term amidated

<400> SEQUENCE: 124

Glu Arg Leu Arg Arg Arg Ile Xaa Leu Ala Arg Xaa His His Ser Thr
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (7)..(7)
<223> OTHER INFORMATION: Any amino acid available for cross linking
<220> FEATURE:
<221> NAME/KEY: misc_feature
<222> LOCATION: (7)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any amino acid available for cross linking
<220> FEATURE:
<223> OTHER INFORMATION: C-term amidated

<400> SEQUENCE: 125

Ala Leu Arg Arg Arg Ile Xaa Leu Cys Ala Xaa His His Ser Thr
1               5                   10                  15
```